(12) United States Patent
Tuval et al.

(10) Patent No.: US 9,445,898 B2
(45) Date of Patent: Sep. 20, 2016

(54) MITRAL VALVE REPAIR

(75) Inventors: Yosi Tuval, Even Yehuda (IL); Ilia Hariton, Zichron Yaackov (IL)

(73) Assignee: Medtronic Ventor Technologies LTD., Minneapolis, MN (US)

( * ) Notice: Subject to any disclaimer, the term of this patent is extended or adjusted under 35 U.S.C. 154(b) by 610 days.

(21) Appl. No.: 13/038,097

(22) Filed: Mar. 1, 2011

(65) Prior Publication Data

US 2012/0226349 A1    Sep. 6, 2012

(51) Int. Cl.
| | | |
|---|---|---|
| *A61F 2/24* | (2006.01) | |
| *A61B 17/04* | (2006.01) | |
| *A61B 17/00* | (2006.01) | |
| *A61B 17/06* | (2006.01) | |
| *A61B 17/064* | (2006.01) | |
| *A61B 17/22* | (2006.01) | |

(52) U.S. Cl.
CPC ......... *A61F 2/2457* (2013.01); *A61B 17/0401* (2013.01); *A61F 2/2445* (2013.01); *A61B 2017/00243* (2013.01); *A61B 2017/00292* (2013.01); *A61B 2017/00783* (2013.01); *A61B 2017/0409* (2013.01); *A61B 2017/0417* (2013.01); *A61B 2017/0441* (2013.01); *A61B 2017/0443* (2013.01); *A61B 2017/0649* (2013.01); *A61B 2017/06095* (2013.01); *A61B 2017/22038* (2013.01)

(58) Field of Classification Search
CPC ....................................................... A61F 2/24
USPC ....................................................... 623/2.37
See application file for complete search history.

(56) References Cited

U.S. PATENT DOCUMENTS

| | | |
|---|---|---|
| 6,210,432 B1 | 4/2001 | Solem et al. |
| 6,332,893 B1 | 12/2001 | Mortier et al. |
| 6,602,288 B1 | 8/2003 | Cosgrove et al. |
| 6,702,835 B2 | 3/2004 | Ginn |
| 6,723,038 B1 | 4/2004 | Schroeder et al. |
| 6,776,784 B2 | 8/2004 | Ginn |
| 6,962,605 B2 | 11/2005 | Cosgrove et al. |
| 6,986,775 B2 | 1/2006 | Morales et al. |
| 6,989,028 B2 | 1/2006 | Lashinski et al. |
| 6,997,950 B2 | 2/2006 | Chawla |
| 6,997,951 B2 | 2/2006 | Solem et al. |
| 7,011,682 B2 | 3/2006 | Lashinski et al. |
| 7,037,334 B1 | 5/2006 | Hlavka et al. |
| 7,044,967 B1 | 5/2006 | Solem et al. |
| 7,056,325 B1 | 6/2006 | Makower et al. |
| 7,090,695 B2 | 8/2006 | Solem et al. |
| 7,166,127 B2 | 1/2007 | Spence et al. |
| 7,211,110 B2 | 5/2007 | Rowe et al. |
| 7,220,265 B2 | 5/2007 | Chanduszko et al. |

(Continued)

FOREIGN PATENT DOCUMENTS

| | | |
|---|---|---|
| EP | 1943982 | 7/2008 |
| WO | WO95/27442 | 10/1995 |
| WO | 2008/129405 | 10/2008 |

*Primary Examiner* — Matthew Schall

(57) ABSTRACT

Apparatus and methods are provided for use with a mitral valve of a heart of a subject. The apparatus includes a P1-anchor, a P2-anchor, and a P3-anchor, that are anchored to tissue in a vicinity of, respectively, P1, P2 and P3 segments of a posterior leaflet of the mitral valve, a tether being fixedly coupled to the P2-anchor, and slidably coupled to the P1 and P3 anchors. A cardiac-site anchor anchors the tether to an anchoring location that is at a cardiac site that is anterior and inferior to the posterior leaflet. Other embodiments are also described.

15 Claims, 49 Drawing Sheets

(56) References Cited

U.S. PATENT DOCUMENTS

| | | |
|---|---|---|
| 7,296,577 B2 | 11/2007 | Lashinski et al. |
| 7,311,728 B2 | 12/2007 | Solem et al. |
| 7,431,692 B2 | 10/2008 | Zollinger et al. |
| 7,431,726 B2 | 10/2008 | Spence et al. |
| 7,588,582 B2 | 9/2009 | Starksen et al. |
| 7,635,386 B1 | 12/2009 | Gammie |
| 7,637,945 B2 | 12/2009 | Solem et al. |
| 7,666,193 B2 | 2/2010 | Starksen et al. |
| 7,699,892 B2 | 4/2010 | Rafiee et al. |
| 7,717,954 B2 | 5/2010 | Solem et al. |
| 7,758,637 B2 | 7/2010 | Starksen et al. |
| 2003/0105519 A1 | 6/2003 | Fasol et al. |
| 2004/0193191 A1 | 9/2004 | Starksen et al. |
| 2004/0220596 A1 | 11/2004 | Frazier et al. |
| 2004/0243227 A1 | 12/2004 | Starksen et al. |
| 2004/0260393 A1 | 12/2004 | Rahdert et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0125011 A1 | 6/2005 | Spence et al. |
| 2005/0177180 A1 | 8/2005 | Kaganov et al. |
| 2005/0187568 A1 | 8/2005 | Klenk et al. |
| 2005/0197696 A1 | 9/2005 | Duran |
| 2005/0267495 A1 | 12/2005 | Ginn et al. |
| 2005/0273138 A1 | 12/2005 | To et al. |
| 2006/0025787 A1 | 2/2006 | Morales et al. |
| 2006/0052821 A1 | 3/2006 | Abbott et al. |
| 2006/0095025 A1 | 5/2006 | Levine et al. |
| 2007/0010857 A1 | 1/2007 | Sugimoto et al. |
| 2007/0055206 A1 | 3/2007 | To et al. |
| 2007/0073315 A1 | 3/2007 | Ginn et al. |
| 2007/0112424 A1 | 5/2007 | Spence et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2008/0228032 A1 | 9/2008 | Starksen et al. |
| 2008/0228165 A1 | 9/2008 | Spence et al. |
| 2008/0228265 A1 | 9/2008 | Spence et al. |
| 2008/0228266 A1 | 9/2008 | McNamara et al. |
| 2008/0228267 A1 | 9/2008 | Spence et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0234728 A1 | 9/2008 | Starksen et al. |
| 2008/0234815 A1 | 9/2008 | Starksen |
| 2008/0243150 A1 | 10/2008 | Starksen et al. |
| 2008/0275503 A1 | 11/2008 | Spence et al. |
| 2008/0294177 A1* | 11/2008 | To et al. ............... 606/139 |
| 2009/0076547 A1 | 3/2009 | Sugimoto et al. |
| 2009/0209950 A1 | 8/2009 | Starksen |
| 2009/0222083 A1 | 9/2009 | Nguyen et al. |
| 2009/0234318 A1 | 9/2009 | Loulmet et al. |
| 2009/0276038 A1 | 11/2009 | Tremolis et al. |
| 2009/0276040 A1* | 11/2009 | Rowe et al. ............. 623/2.18 |
| 2010/0010538 A1* | 1/2010 | Juravic et al. ........... 606/228 |
| 2010/0023056 A1 | 1/2010 | Johansson et al. |
| 2010/0030328 A1 | 2/2010 | Seguin et al. |
| 2010/0070028 A1 | 3/2010 | Sugimoto |
| 2010/0094248 A1 | 4/2010 | Nguyen et al. |
| 2010/0161042 A1 | 6/2010 | Maisano et al. |

* cited by examiner

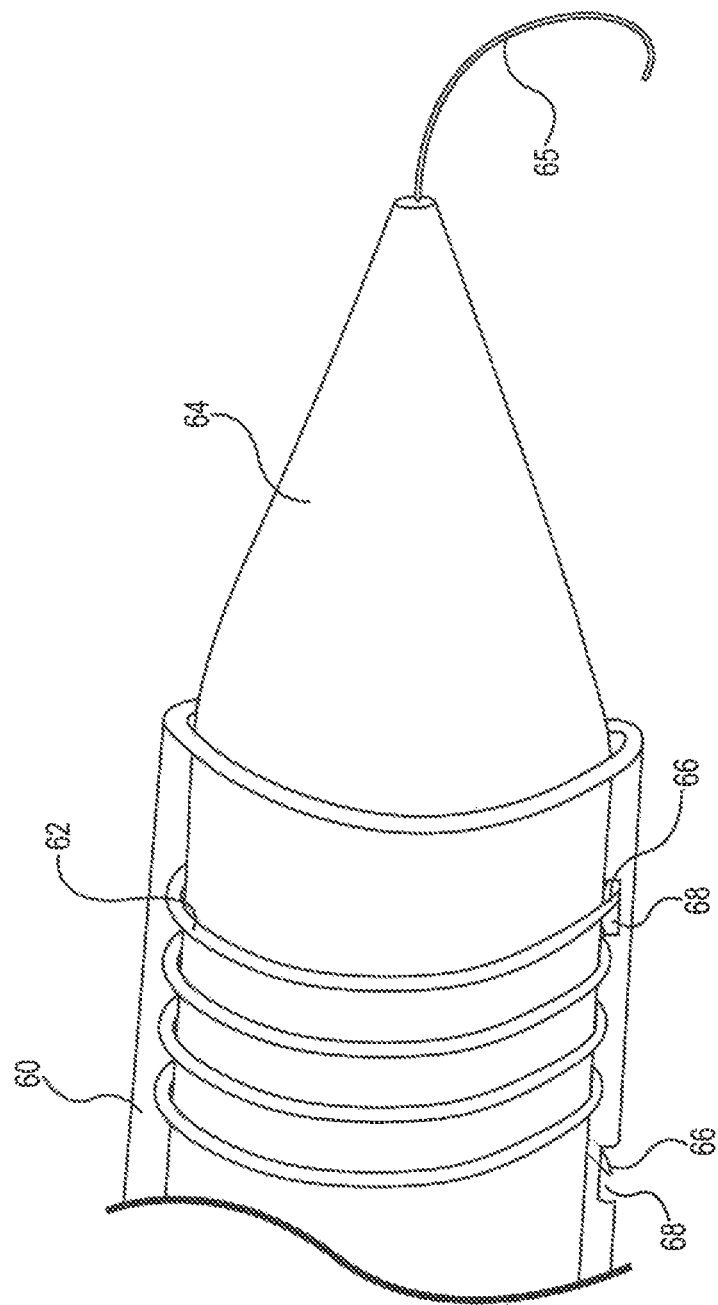

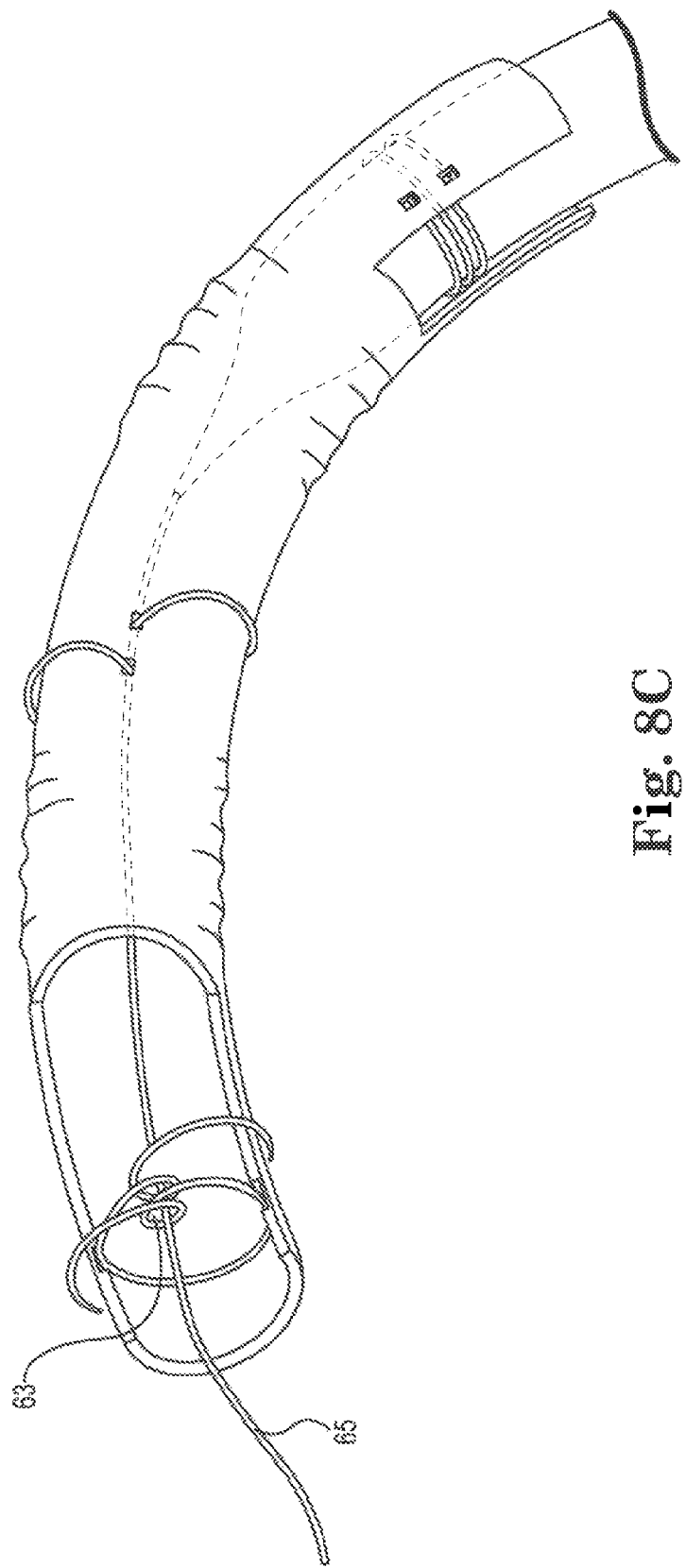

MITRAL VALVE REPAIR

FIELD OF EMBODIMENTS OF THE INVENTION

Some applications of the present invention generally relate to implanted medical apparatus. Specifically, some applications of the present invention relate to apparatus and methods for repairing a mitral valve.

BACKGROUND

The mitral valve is located at the junction between the left atrium and the left ventricle of the heart. During diastole, the valve opens, in order to allow the flow of blood from the left atrium to the left ventricle. During systole, when the left ventricle pumps blood into the body via the aorta, the valve closes to prevent the backflow of blood into the left atrium. The mitral valve is composed of two leaflets (the posterior leaflet and the anterior leaflet), which are located at the mitral annulus, the annulus being a ring that forms the junction between the left atrium and the left ventricle. The mitral valve leaflets are tethered to papillary muscles of the left ventricle via chordae tendineae. The chordae tendineae prevent the mitral valve leaflets from averting into the left atrium during systole.

Mitral valve regurgitation is a condition in which the mitral valve does not close completely, resulting in the backflow of blood from the left ventricle to the left atrium. In some cases, regurgitation is caused by dilation of the mitral annulus, and, in particular, by an increase in the anteroposterior diameter of the mitral annulus. Alternatively or additionally, mitral regurgitation is causes by dilation of the left ventricle that, for example, may result from an infarction. The dilation of the left ventricle results in the papillary muscles consistently tethering the mitral valve leaflets into an open configuration, via the chordae tendineae.

SUMMARY OF EMBODIMENTS

For some applications of the present invention, the mitral annulus and the left ventricle of a subject are reshaped in order to treat mitral regurgitation. Typically, a P1-anchor, a P2-anchor, and a P3-anchor, are anchored to tissue in the vicinity of, respectively, P1, P2 and P3 segments of the posterior leaflet of the mitral valve. A tether that passes through the anchors is pulled and anchored to an anchoring location that is at a cardiac site that is anterior and inferior to the posterior leaflet, e.g., in the vicinity of the apex of the heart. Typically, the pulling of the tether decreases the circumference of the mitral annulus. The anchoring of the tether to the cardiac site causes the anteroposterior diameter of the mitral annulus to decrease, and reshapes the left ventricle such that tethering of the mitral leaflets by the chordae tendineae is reduced.

Typically, a healthy mitral annulus has a saddle shape. The saddle shape of a healthy mitral annulus further reduces the circumference of the annulus (due to folding of the mitral leaflets), and reduces leaflet stress, relative to a flattened annulus. In some diseased mitral valves, the annulus dilates such that the saddle shape of the annulus is flattened. For some applications of the present invention, the tether that passes through the P1, P2, and P3 anchors is fixedly coupled to the P2 anchor, and is slidably coupled to the P1 and P3 anchors. For some applications, fixedly coupling the tether to the P2 anchor, and slidably coupling the anchor to the P1 and P3 anchors results in inferior motion of the P1 and P3 anchors relative to the P2 anchor, when the tether is pulled and anchored to the anchoring location, as described hereinabove. In turn, this results in the restoration of a saddle-shape to the annulus.

For some applications, a ring is implanted in the vicinity of (e.g., on or posterior to) the mitral annulus. Typically, the ring is implanted on the posterior mitral annulus, in order to reduce the circumference of the mitral annulus. A plurality (e.g., three) self-suturing anchors are disposed inside the ring. The anchors are shaped to define openings therethrough, and a mandrel is reversibly disposed through the openings. In response to the removal of the mandrel from the openings, the anchors automatically become coupled to a leaflet of the mitral valve. Typically, re-inserting the mandrel through the openings, results in each of the anchors exiting the tissue via an exit route that is the reverse of the entry route of the anchor.

There is therefore provided, in accordance with some applications of the present invention, apparatus for use with a mitral valve of a heart of a subject, the apparatus including:

a P1-anchor, a P2-anchor, and a P3-anchor, configured to become anchored to tissue in a vicinity of, respectively, P1, P2 and P3 segments of a posterior leaflet of the mitral valve, a tether being fixedly coupled to the P2-anchor, and slidably coupled to the P1 and P3 anchors; and a cardiac-site anchor configured to anchor the tether to an anchoring location that is at a cardiac site that is anterior and inferior to the posterior leaflet.

For some applications, the cardiac-site anchor includes a clip.

For some applications, the P1-anchor, the P2-anchor, and the P3-anchor include clips.

For some applications, the clips are shaped to define openings therethrough, the apparatus further includes a mandrel configured to be reversibly disposed through the openings, and, in response to removing the mandrel from the openings, the clips are configured to automatically become anchored to the tissue.

For some applications, the apparatus further includes a mitral ring configured to become coupled to the tissue by the anchors.

For some applications, the mitral ring includes compressible portion thereof, the compressible portions being disposed between adjacent anchors of the anchors.

There is further provided, in accordance with some applications of the present invention, a method of treating a mitral valve of a heart of a subject, the method comprising:

reducing a circumference of a mitral annulus and restoring a saddle-shape of the mitral annulus, by:

anchoring a P1-anchor, a P2-anchor, and a P3-anchor to tissue in a vicinity of, respectively, P1, P2 and P3 segments of a posterior leaflet of the mitral valve, a tether being fixedly coupled to the P2-anchor, and slidably coupled to the P1 and P3 anchors;

subsequently, pulling the tether; and anchoring the tether to an anchoring location that is at a cardiac site that is anterior and inferior to the posterior leaflet.

For some applications, anchoring the anchor to the anchoring location includes anchoring the anchor to an inner surface of the heart at a vicinity of an apex of the heart.

For some applications, anchoring the anchor to the anchoring location includes anchoring the anchor to an outer surface of the heart at a vicinity of an apex of the heart.

For some applications, anchoring the P1-anchor, the P2-anchor, and the P3-anchor includes inserting the anchors transmyocardially into a left atrium of the subject, and anchoring the anchors to a left atrial side of the posterior leaflet of the mitral valve.

For some applications, the P1-anchor, the P2-anchor, and the P3-anchor include a P1-clip, a P2-clip, and a P3-clip, and anchoring the P1-anchor, the P2-anchor, and the P3-anchor includes inserting the clips into a left ventricle of the subject and clipping the clips to a left ventricular side of the posterior leaflet of the mitral valve, such that the clips penetrate tissue of the posterior leaflet.

For some applications, anchoring the tether to the anchoring location includes decreasing a ratio of an anteroposterior diameter of the mitral annulus to a lateral diameter of the mitral annulus.

For some applications, anchoring the tether to the anchoring location includes reshaping a left ventricle of the subject.

For some applications, the anchors are shaped to define openings therethrough, and anchoring the anchors includes causing the anchors to become anchored automatically, by removing a mandrel from inside the openings defined by the anchors.

For some applications, the anchors are coupled to a ring, and anchoring the anchors to the tissue includes coupling the ring to the tissue.

There is additionally provided, in accordance with some applications of the present invention, a method of treating a mitral valve of a heart of a subject, the method comprising:
  reducing a circumference of a mitral annulus and reshaping a left ventricle, by:
    anchoring a P1-anchor, a P2-anchor, and a P3-anchor to tissue in a vicinity of, respectively, P1, P2 and P3 segments of a posterior leaflet of the mitral valve;
    subsequently, pulling a tether that passes through the anchors; and
    anchoring the tether to an anchoring location that is at a cardiac site that is anterior and inferior to the posterior leaflet.

For some applications, anchoring the anchor to the anchoring location includes anchoring the anchor to an inner surface of the heart at a vicinity of an apex of the heart.

For some applications, anchoring the anchor to the anchoring location includes anchoring the anchor to an outer surface of the heart at a vicinity of an apex of the heart.

For some applications, anchoring the P1-anchor, the P2-anchor, and the P3-anchor includes inserting the anchors transmyocardially into a left atrium of the subject, and anchoring the anchors to a left atrial side of the posterior leaflet of the mitral valve.

For some applications, the P1-anchor, the P2-anchor, and the P3-anchor include a P1-clip, a P2-clip, and a P3-clip, and anchoring the P1-anchor, the P2-anchor, and the P3-anchor includes inserting the clips into a left ventricle of the subject and clipping the clips to a left ventricular side of the posterior leaflet of the mitral valve, such that the clips penetrate tissue of the posterior leaflet.

For some applications, anchoring the tether to the anchoring location includes decreasing a ratio of an anteroposterior diameter of the mitral annulus to a lateral diameter of the mitral annulus.

For some applications, anchoring the tether to the anchoring location includes restoring a saddle-shape of the mitral annulus.

For some applications, anchoring the P1-anchor, the P2-anchor, and the P3-anchor includes anchoring the anchors to the tissue, the tether being fixedly coupled to the P2-anchor, and slidably coupled to the P1 and P3 anchors.

For some applications, the anchors are shaped to define openings therethrough, and anchoring the anchors includes causing the anchors to become anchored automatically, by removing a mandrel from inside the openings defined by the anchors.

For some applications, the anchors are coupled to a ring, and anchoring the anchors to the tissue includes coupling the ring to the tissue.

There is further provided, in accordance with some applications of the present invention, a method of treating a mitral valve of a heart of a subject, the method comprising:
  reducing a circumference of a mitral annulus and decreasing a ratio of an anteroposterior diameter of the mitral annulus to a lateral diameter of the mitral annulus, by:
    anchoring a P1-anchor, a P2-anchor, and a P3-anchor to tissue in a vicinity of, respectively, P1, P2 and P3 segments of a posterior leaflet of the mitral valve;
    subsequently, pulling a tether that passes through the anchors; and
    anchoring the tether to an anchoring location that is at a cardiac site that is anterior and inferior to the posterior leaflet.

For some applications, anchoring the anchor to the anchoring location includes anchoring the anchor to an inner surface of the heart at a vicinity of an apex of the heart.

For some applications, anchoring the anchor to the anchoring location includes anchoring the anchor to an outer surface of the heart at a vicinity of an apex of the heart.

For some applications, anchoring the P1-anchor, the P2-anchor, and the P3-anchor includes inserting the anchors transmyocardially into a left atrium of the subject, and anchoring the anchors to a left atrial side of the posterior leaflet of the mitral valve.

For some applications, the P1-anchor, the P2-anchor, and the P3-anchor include a P1-clip, a P2-clip, and a P3-clip, and anchoring the P1-anchor, the P2-anchor, and the P3-anchor includes inserting the clips into a left ventricle of the subject and clipping the clips to a left ventricular side of the posterior leaflet of the mitral valve, such that the clips penetrate tissue of the posterior leaflet.

For some applications, anchoring the tether to the anchoring location includes reshaping a left ventricle of the subject.

For some applications, anchoring the tether to the anchoring location includes restoring a saddle-shape of the mitral annulus.

For some applications, anchoring the P1-anchor, the P2-anchor, and the P3-anchor includes anchoring the anchors to the tissue, the tether being fixedly coupled to the P2-anchor, and slidably coupled to the P1 and P3 anchors.

For some applications, the anchors are shaped to define openings therethrough, and anchoring the anchors includes causing the anchors to become anchored automatically, by removing a mandrel from inside the openings defined by the anchors.

For some applications, the anchors are coupled to a ring, and anchoring the anchors to the tissue includes coupling the ring to the tissue.

There is further provided, in accordance with some applications of the present invention, apparatus, including:
  a plurality of anchoring elements, each of the anchoring elements being an elongate element that is curved to define an opening;
  a housing configured to hold each of the anchoring elements; and
  a mandrel that is reversibly disposable through the openings defined by the anchoring elements, the anchoring elements being configured such that, in response to removal of the mandrel from the openings, ends of the anchoring elements automatically move outwardly, and diameters of the openings decrease, due to elastic loading of the anchoring elements.

For some applications, ends of the anchoring elements are sharp.

For some applications, each of the anchoring elements is configured to automatically become anchored to tissue of a subject, by entering the tissue via an entry route, in response to removal of the mandrel from the opening defined by the anchoring element.

For some applications, each of the anchoring elements is configured to automatically exit the tissue via an exit route that is a reverse of the entry route, in response to reinsertion of the mandrel through the opening.

For some applications, the anchoring elements are configured to couple the housing to the tissue by becoming anchored to the tissue.

For some applications, the housing includes flexible portions thereof, the flexible portions being disposed between adjacent anchoring elements of the anchoring elements.

For some applications, the anchoring elements include a P1-anchor, a P2-anchor, and a P3-anchor configured to become coupled to tissue in a vicinity of, respectively, P1, P2 and P3 segments of a posterior leaflet of the mitral valve.

For some applications, the apparatus further includes a tether configured to pass through the anchors.

For some applications, the tether is fixedly coupled to the P2-anchor and is slidably coupled to the P1-anchor and the P3-anchor.

For some applications, the apparatus further includes a cardiac-site anchor configured to anchor ends of the tether to a cardiac site of a heart of a subject.

There is additionally provided, in accordance with some applications of the present invention, apparatus, including:
a plurality of anchoring elements;
a mandrel that is reversibly disposable through the anchoring elements,
each of the anchoring elements being configured to:
automatically become anchored to tissue of a subject, by entering the tissue via an entry route, in response to removal of the mandrel from the anchoring element; and
subsequently, automatically exit the tissue via an exit route that is a reverse of the entry route, in response to reinsertion of the mandrel through the anchoring element.

For some applications, ends of the anchoring elements are sharp.

For some applications, each of the anchoring elements includes an elongate element that is curved to define an opening, the mandrel is reversibly disposable through the openings, and ends of respective anchoring elements are configured to automatically become anchored to the respective locations of the tissue by moving outwardly, in response to removal of the mandrel from the openings.

For some applications, the anchoring elements are configured such that, in response to removal of the mandrel from the openings, ends of the anchoring elements automatically move outwardly, and diameters of the openings decrease, due to elastic loading of the anchoring elements.

For some applications, the anchoring elements are disposed in a housing, and the anchoring elements are configured to couple the housing to the tissue by becoming anchored to the tissue.

For some applications, the housing includes flexible portions thereof, the flexible portions being disposed between adjacent anchoring elements of the anchoring elements.

For some applications, the anchoring elements include a P1-anchor, a P2-anchor, and a P3-anchor configured to become coupled to tissue in a vicinity of, respectively, P1, P2 and P3 segments of a posterior leaflet of the mitral valve.

For some applications, the apparatus further includes a tether configured to pass through the anchors.

For some applications, the tether is fixedly coupled to the P2-anchor and is slidably coupled to the P1-anchor and the P3-anchor.

For some applications, the apparatus further includes a cardiac-site anchor configured to anchor ends of the tether to a cardiac site of a heart of a subject.

There is further provided, in accordance with some applications of the present invention, a method, including:
inserting a plurality of anchoring elements into tissue of a subject by removing a mandrel from the anchoring elements, each of the anchoring elements being configured to enter the tissue via an entry route; and
subsequently, causing each of the anchoring elements to automatically exit the tissue via an exit route in response to reinsertion of the mandrel through the anchoring elements, the exit route of each anchoring element being a reverse of the entry route of the anchoring element.

For some applications, the anchoring elements include anchoring elements that are elongate elements that are curved to define openings, and inserting the plurality of anchoring elements into the tissue includes causing ends of the anchoring elements to automatically become anchored to respective locations of the tissue by moving outwardly, by removing the mandrel from the openings.

For some applications, the tissue includes prosthetic tissue, and inserting the anchors into the tissue includes inserting the anchors into the prosthetic tissue.

For some applications, the tissue includes natural tissue, and inserting the anchors into the tissue includes inserting the anchors into the natural tissue.

For some applications, the tissue includes tissue at a site selected from the group consisting of a site of a gastrointestinal tract of the subject and a cardiac site of the subject, and inserting the anchors into the tissue includes inserting the anchors into the tissue at the selected site.

For some applications, inserting the plurality of anchoring elements into the tissue includes anchoring a P1-anchor, a P2-anchor, and a P3-anchor, to tissue in a vicinity of, respectively, P1, P2 and P3 segments of a posterior leaflet of the mitral valve.

For some applications, the method further includes pulling a tether that passes through the anchors, and anchoring the tether to an anchoring location that is at a cardiac site that is anterior and inferior to the posterior leaflet.

For some applications, anchoring the anchor to the anchoring location includes anchoring the anchor to an inner surface of the heart at a vicinity of an apex of the heart.

For some applications, anchoring the anchor to the anchoring location includes anchoring the anchor to an outer surface of the heart at a vicinity of an apex of the heart.

For some applications, anchoring the P1-anchor, the P2-anchor, and the P3-anchor includes inserting the anchors into a left atrium of the subject, and anchoring the anchors to a left atrial side of the posterior leaflet of the mitral valve.

For some applications, anchoring the P1-anchor, the P2-anchor, and the P3-anchor includes inserting the anchors into a left ventricle of the subject and inserting the anchors into a left ventricular side of the posterior leaflet of the mitral valve, such that the anchors penetrate tissue of the posterior leaflet.

For some applications, anchoring the tether to the anchoring location includes decreasing a ratio of an anteroposterior diameter of a mitral annulus of the subject to a lateral diameter of the mitral annulus.

For some applications, anchoring the tether to the anchoring location includes restoring a saddle-shape of a mitral annulus of the subject.

For some applications, anchoring the tether to the anchoring location includes decreasing a circumference of a mitral annulus of the subject.

For some applications, anchoring the tether to the anchoring location includes reshaping a left ventricle of the subject.

For some applications, anchoring the P1-anchor, the P2-anchor, and the P3-anchor includes anchoring the anchors to the tissue, a tether being fixedly coupled to the P2-anchor, and slidably coupled to the P1 and P3 anchors.

There is further provided, in accordance with some applications of the present invention, apparatus for use with tissue of a subject, including:

a plurality of anchoring elements configured to become anchored to respective locations of the tissue, each of the anchoring elements being an elongate element that is curved to define an opening;

a housing configured to hold each of the anchoring elements, during anchoring of the anchoring elements to the tissue; and a mandrel that is disposed through the openings defined by the anchoring elements, ends of the anchoring elements being configured to automatically become anchored to the respective locations of the tissue by moving outwardly, in response to removal of the mandrel from the openings.

For some applications, ends of the anchoring elements are sharp.

For some applications, the anchoring elements are configured such that, in response to removal of the mandrel from the openings, ends of the anchoring elements automatically move outwardly, and diameters of the openings decrease, due to elastic loading of the anchoring elements.

For some applications, each of the anchoring elements is configured to automatically become anchored to tissue of a subject, by entering the tissue via an entry route, in response to removal of the mandrel from the opening defined by the anchoring element.

For some applications, each of the anchoring elements is configured to automatically exit the tissue via an exit route that is a reverse of the entry route, in response to reinsertion of the mandrel through the opening.

For some applications, the anchoring elements are configured to couple the housing to the tissue by becoming anchored to the tissue.

For some applications, the housing includes flexible portions thereof, the flexible portions being disposed between adjacent anchoring elements of the anchoring elements.

For some applications, the anchoring elements include a P1-anchor, a P2-anchor, and a P3-anchor configured to become coupled to tissue in a vicinity of, respectively, P1, P2 and P3 segments of a posterior leaflet of the mitral valve.

For some applications, the apparatus further includes a tether configured to pass through the anchors.

For some applications, the tether is fixedly coupled to the P2-anchor and is slidably coupled to the P1-anchor and the P3-anchor.

For some applications, the apparatus further includes a cardiac-site anchor configured to anchor ends of the tether to a cardiac site of a heart of a subject.

There is additionally provided, in accordance with some applications of the present invention, a method for use with tissue of a subject, including:

providing a plurality of anchoring elements, each of the anchoring elements being an elongate element that is curved to define an opening, and a mandrel that is disposed through the openings defined by the anchoring elements; and causing ends of the anchoring elements to automatically become anchored to respective locations of the tissue by moving outwardly, by removing the mandrel from the openings.

For some applications, causing the ends of the anchoring elements to automatically become anchored to respective locations of the tissue includes causing each of the anchoring elements to enter tissue via an entry route, the method further including, subsequently, causing each of the anchoring elements to automatically exit the tissue via an exit route in response to reinsertion of the mandrel through the anchoring elements, the exit route of each anchoring element being a reverse of the entry route of the anchoring element.

For some applications, the tissue includes prosthetic tissue, and inserting the anchors into the tissue includes inserting the anchors into the prosthetic tissue.

For some applications, the tissue includes natural tissue, and inserting the anchors into the tissue includes inserting the anchors into the natural tissue.

For some applications, the tissue includes tissue at a site selected from the group consisting of a site of a gastrointestinal tract of the subject and a cardiac site of the subject, and inserting the anchors into the tissue includes inserting the anchors into the tissue at the selected site.

For some applications, inserting the plurality of anchoring elements into the tissue includes anchoring a P1-anchor, a P2-anchor, and a P3-anchor, to tissue in a vicinity of, respectively, P1, P2 and P3 segments of a posterior leaflet of the mitral valve.

For some applications, the method further includes pulling a tether that passes through the anchors, and anchoring the tether to an anchoring location that is at a cardiac site that is anterior and inferior to the posterior leaflet.

For some applications, anchoring the anchor to the anchoring location includes anchoring the anchor to an inner surface of the heart at a vicinity of an apex of the heart.

For some applications, anchoring the anchor to the anchoring location includes anchoring the anchor to an outer surface of the heart at a vicinity of an apex of the heart.

For some applications, anchoring the P1-anchor, the P2-anchor, and the P3-anchor includes inserting the anchors into a left atrium of the subject, and anchoring the anchors to a left atrial side of the posterior leaflet of the mitral valve.

For some applications, anchoring the P1-anchor, the P2-anchor, and the P3-anchor includes inserting the anchors into a left ventricle of the subject and inserting the anchors into a left ventricular side of the posterior leaflet of the mitral valve, such that the anchors penetrate tissue of the posterior leaflet.

For some applications, anchoring the tether to the anchoring location includes decreasing a ratio of an anteroposterior diameter of a mitral annulus of the subject to a lateral diameter of the mitral annulus.

For some applications, anchoring the tether to the anchoring location includes restoring a saddle-shape of a mitral annulus of the subject.

For some applications, anchoring the tether to the anchoring location includes decreasing a circumference of a mitral annulus of the subject.

For some applications, anchoring the tether to the anchoring location includes reshaping a left ventricle of the subject.

For some applications, anchoring the P1-anchor, the P2-anchor, and the P3-anchor includes anchoring the anchors to the tissue, a tether being fixedly coupled to the P2-anchor, and slidably coupled to the P1 and P3 anchors.

The present invention will be more fully understood from the following detailed description of embodiments thereof, taken together with the drawings, in which:

BRIEF DESCRIPTION OF THE DRAWINGS

FIGS. 8A-H are schematic illustrations of a mitral ring, self-suturing anchors being disposed inside the mitral ring, in accordance with some applications of the present invention;

DETAILED DESCRIPTION OF EMBODIMENTS

Figure 1A:
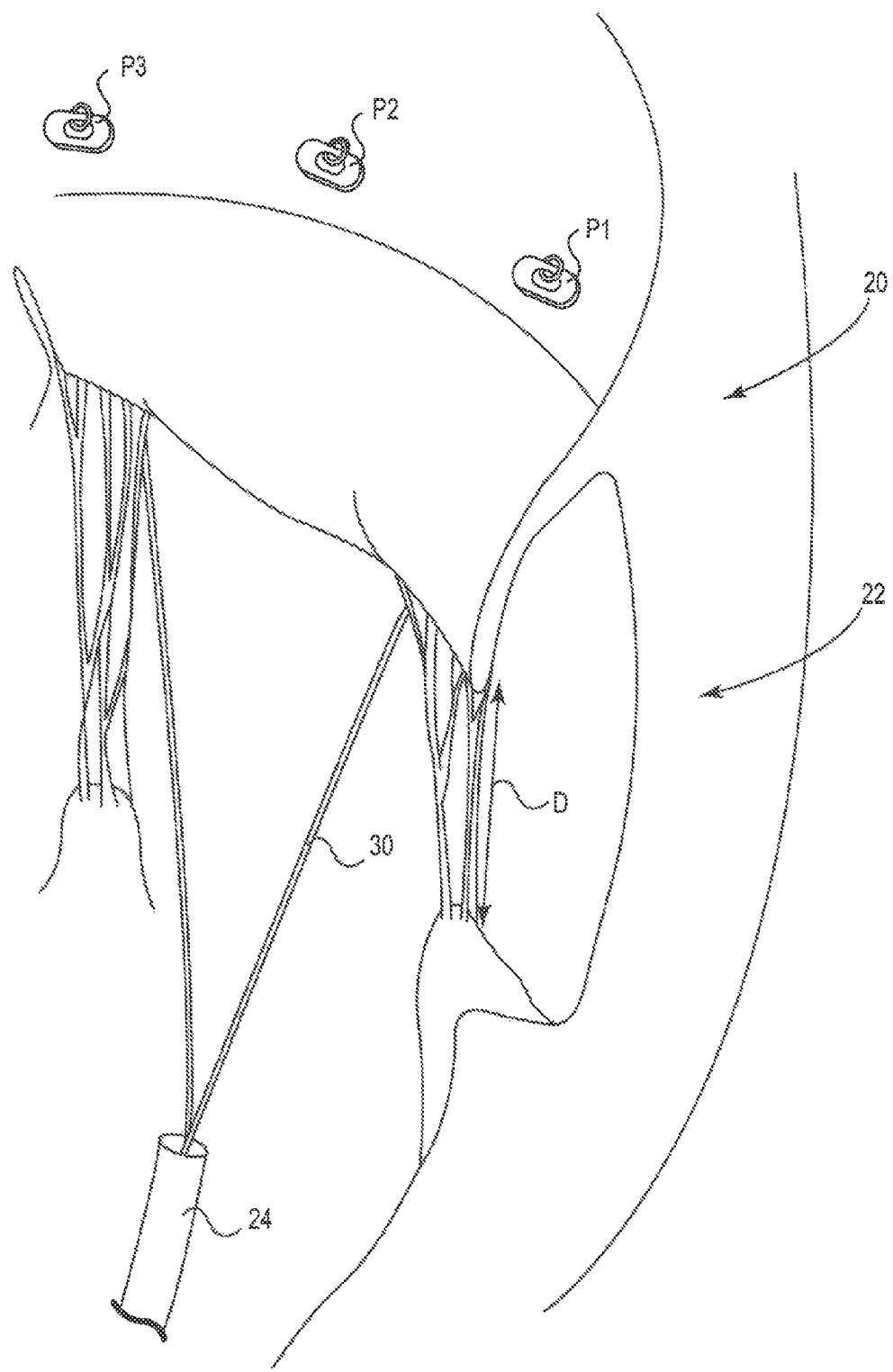
FIGS. 1A-E are schematic illustrations of a mitral valve and a left ventricle being reshaped via a transapical approach, in accordance with some applications of the present invention.

Reference is now made to FIGS. 1A-E, which are schematic illustrations of a mitral valve 20 and a left ventricle 22 being reshaped via a transapical approach, in accordance with some applications of the present invention. As shown in FIG. 1A, a P1-anchor P1, a P2-anchor P2, and a P3-anchor P3 are coupled to tissue in the vicinity of, respectively, the P1, P2 and P3 segments of the posterior mitral valve leaflet. For example, the clips may be coupled to tissue on, or posterior to the P!, P2, and P3 segments (e.g., to respective locations of the mitral annulus).

Anchors P1, P2 and P3 typically include any anchors, clips, and/or pledgets, as are known in the art. For example, the anchors may include clips that comprise a shape-memory alloy, such as nitinol. For some applications, anchors as described in U.S. Pat. No. 7,056,325 to Makower, which is incorporated herein by reference, are used. For some applications, clips (e.g., The U-Clip® manufactured by Medtronic (Minneapolis, Minn.)) are used as anchors, for example, as described hereinbelow with reference to FIGS. 3A-F. For some applications, a mitral ring that includes self-suturing clips, as described hereinbelow with reference to FIGS. 8-10, is used for anchors P1, P2 and P3. Typically, a tissue penetrating sheath penetrates the cardiac muscle behind the posterior leaflet, so as to place the anchors on the atrial side of the posterior leaflet, as described in further detail hereinbelow, with reference to FIGS. 4-7. The penetrating sheath is inserted via a delivery catheter 24, shown in FIG. 1A, for example.

Figure 1B:
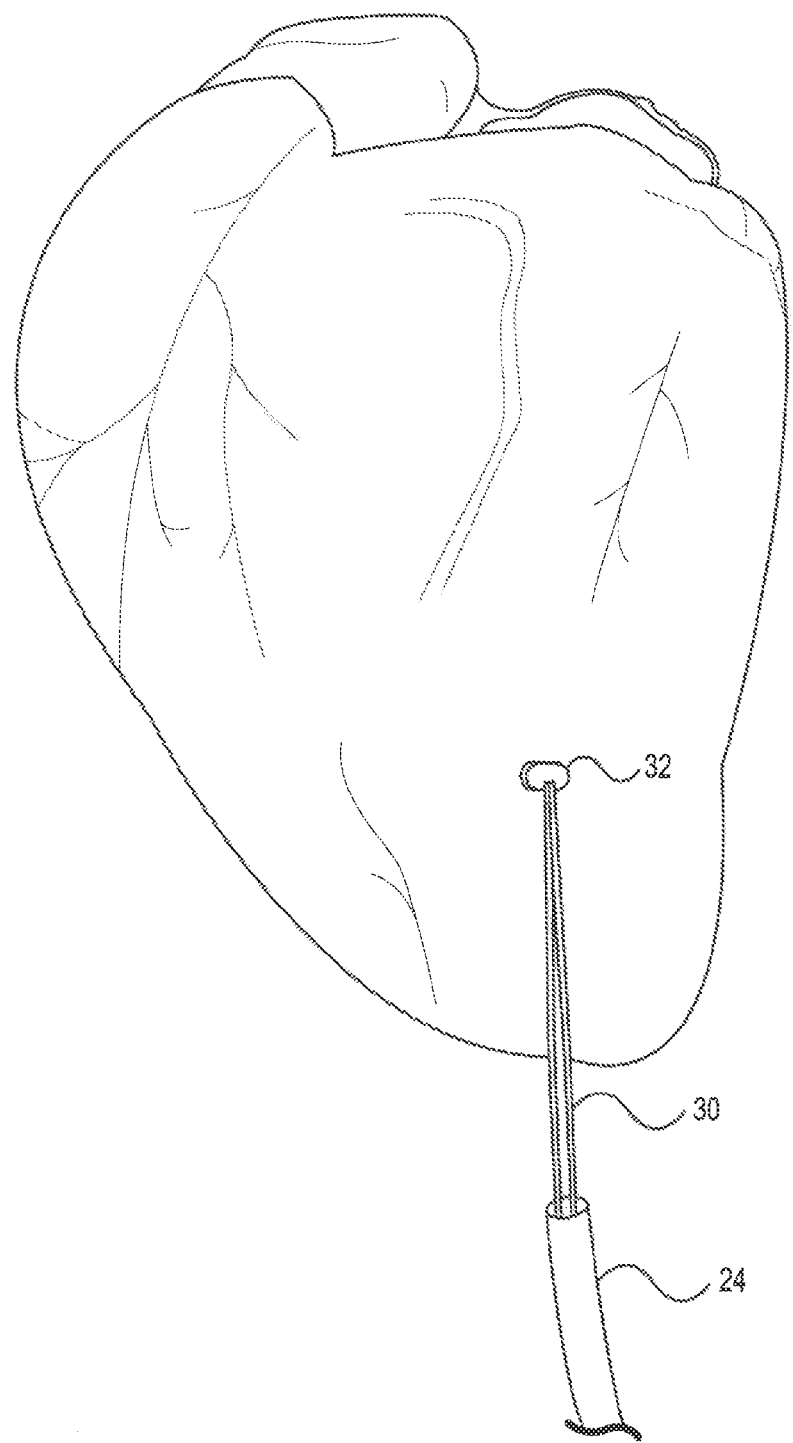
Figure 1C:
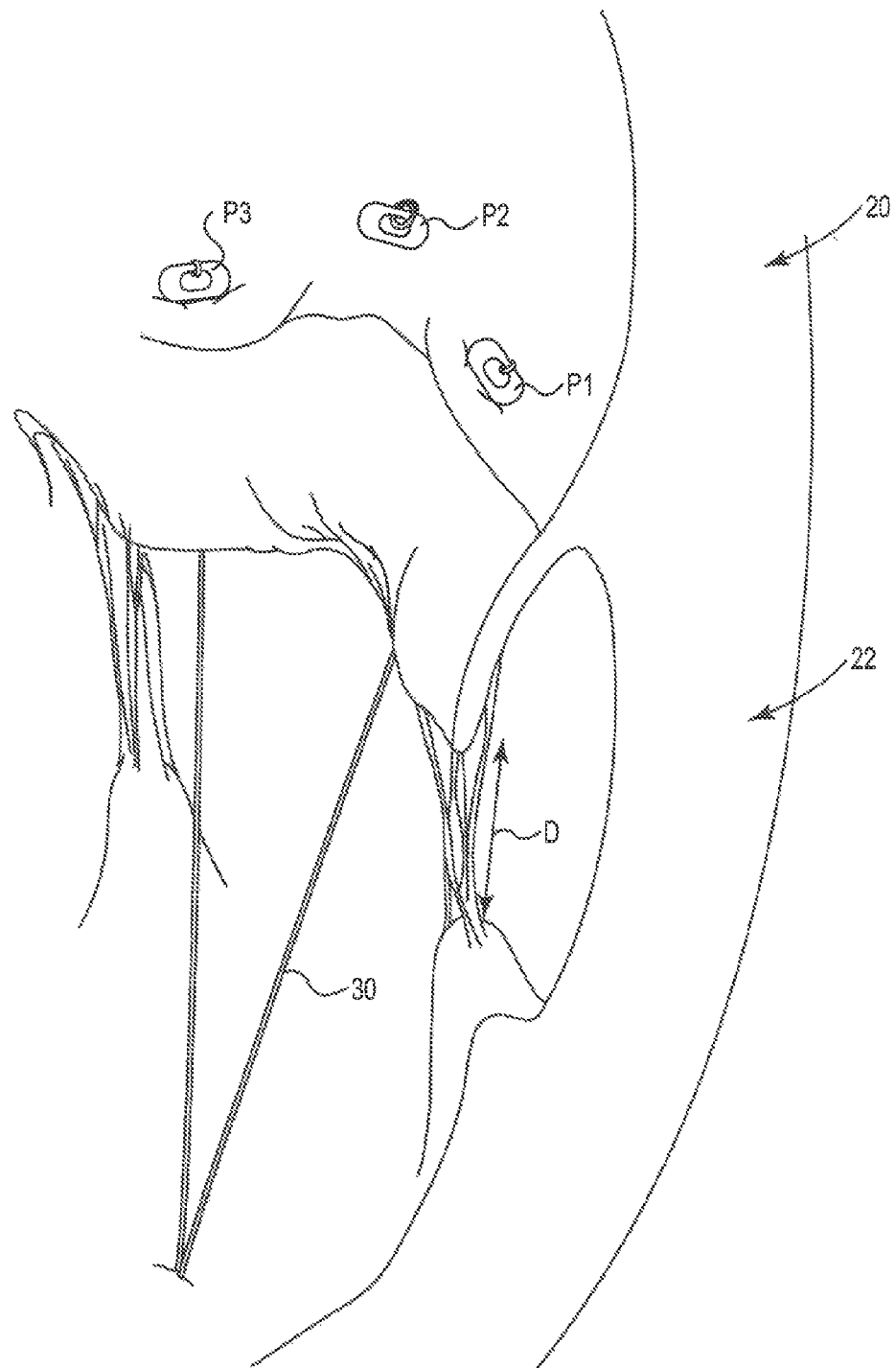

As shown in FIG. 1B, a tether 30, which passes through anchors P1, P2, and P3 is pulled and anchored to an anchoring location 32 that is at a cardiac site that is anterior and inferior to the posterior leaflet, e.g., the outside surface of the heart in the vicinity of the apex of the heart, as shown. Typically, the tether is pulled and anchored to location 32 such that:

the circumference of the mitral annulus decreases (due to the P1, P2, and P3 anchors being pulled anteriorly)

a ratio of the anteroposterior diameter of the annulus to the lateral diameter of the annulus decreases (due to the P1, P2, and P3 anchors being pulled anteriorly)

the distance D (shown in FIGS. 1A and 1C) from the papillary muscles to the posterior leaflet decreases (due to tension in tether 30 pulling the inferior wall of the left ventricle toward the posterior leaflet).

Figure 1D:
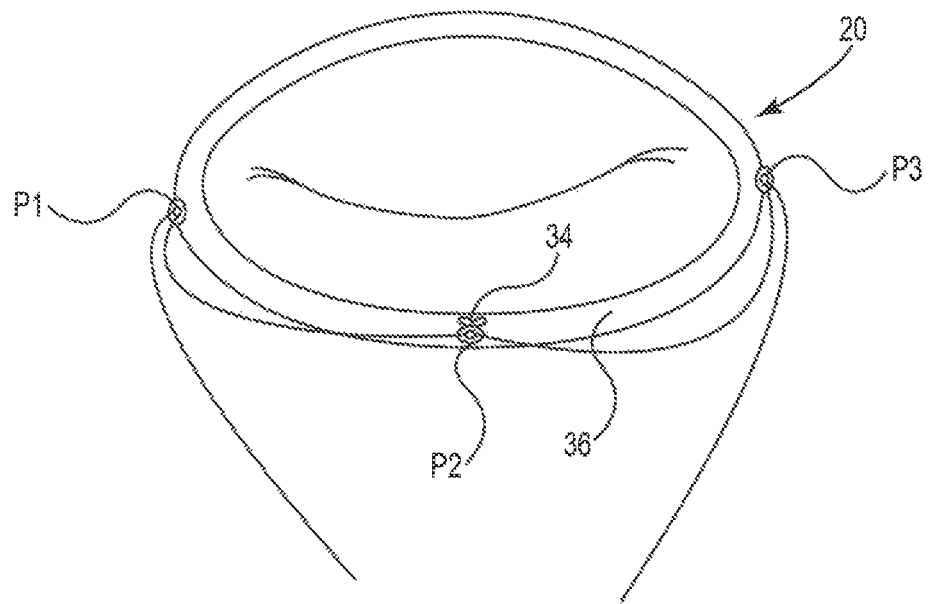
Figure 1E:
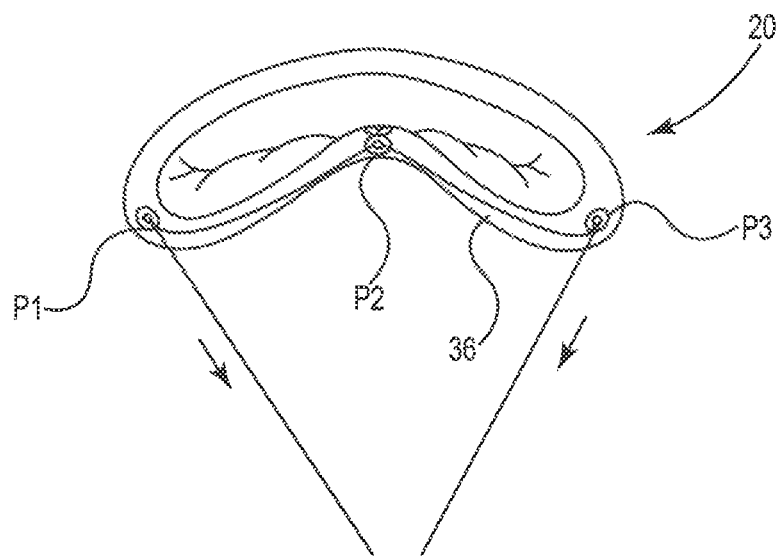

Typically, tether 30 is fixedly coupled to anchor P2, e.g., via a knot 34, as shown in FIG. 1D. The tether is slidably coupled to the P1 and P3 anchors. For some applications, this results in the P1 and P3 anchors being pulled inferiorly with respect to the P2 anchor, when tether 30 is pulled, as shown in FIG. 1E. Typically, this restores a saddle-shape to a mitral annulus 36 that has become misshapen due to dilation of the annulus. As described hereinabove, the saddle-shape of the annulus further reduces the circumference of the annulus, and/or reduces tension in the mitral valve leaflets, relative to a flattened mitral annulus.

For some applications, tether 30 is pulled through the anchors during a beating heart procedure, such that the degree of functional change can be controlled during the procedure, and observed under functional imaging (e.g., echocardiography). Typically, the tether is pulled and anchored in response to the real-time functional imaging, for example, such that an optimal hemodynamic response is achieved.

Figure 2A:
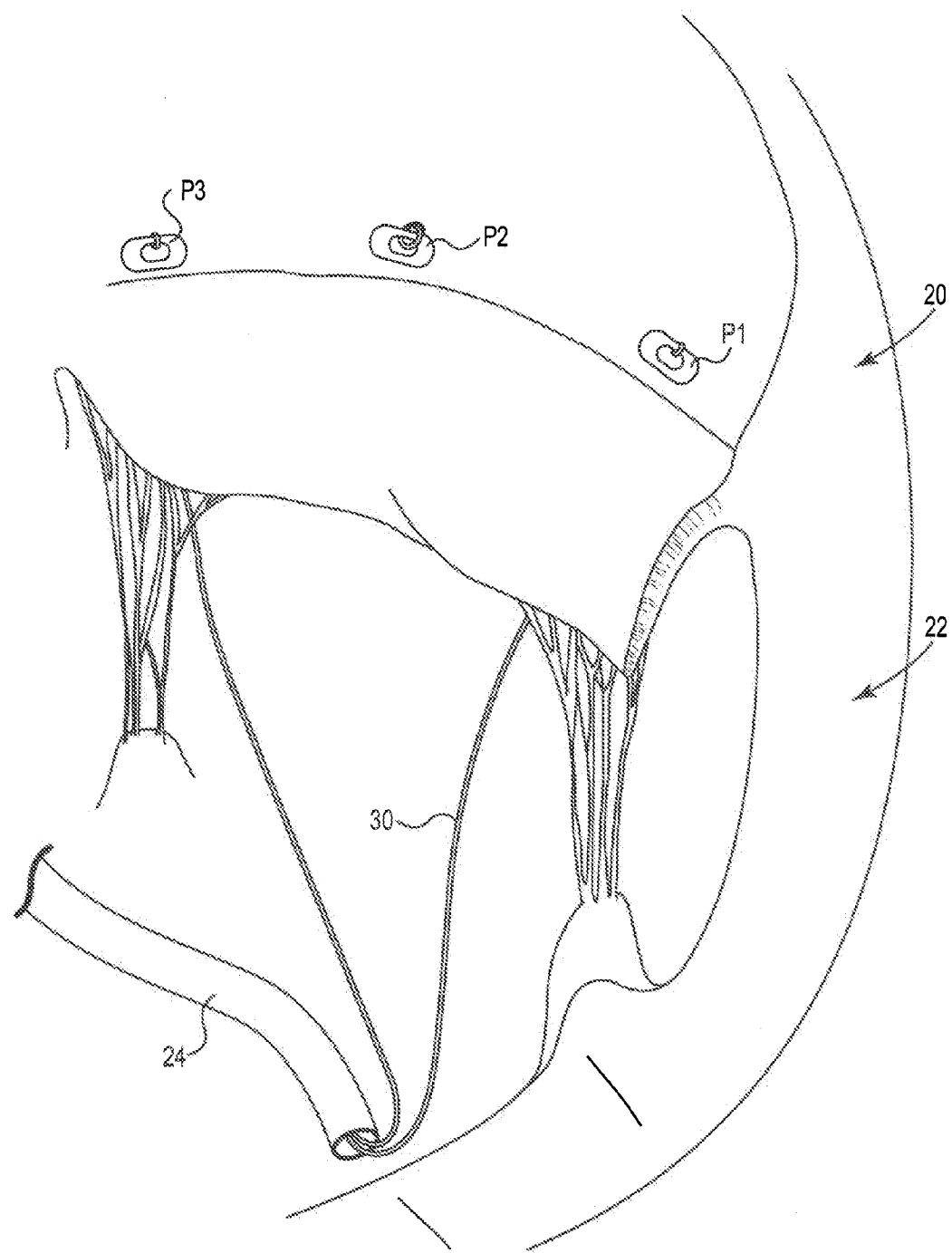
FIGS. 2A-D are schematic illustrations of a mitral valve and a left ventricle being reshaped via a transaortic retrograde approach, in accordance with some applications of the present invention.
Figure 2B:
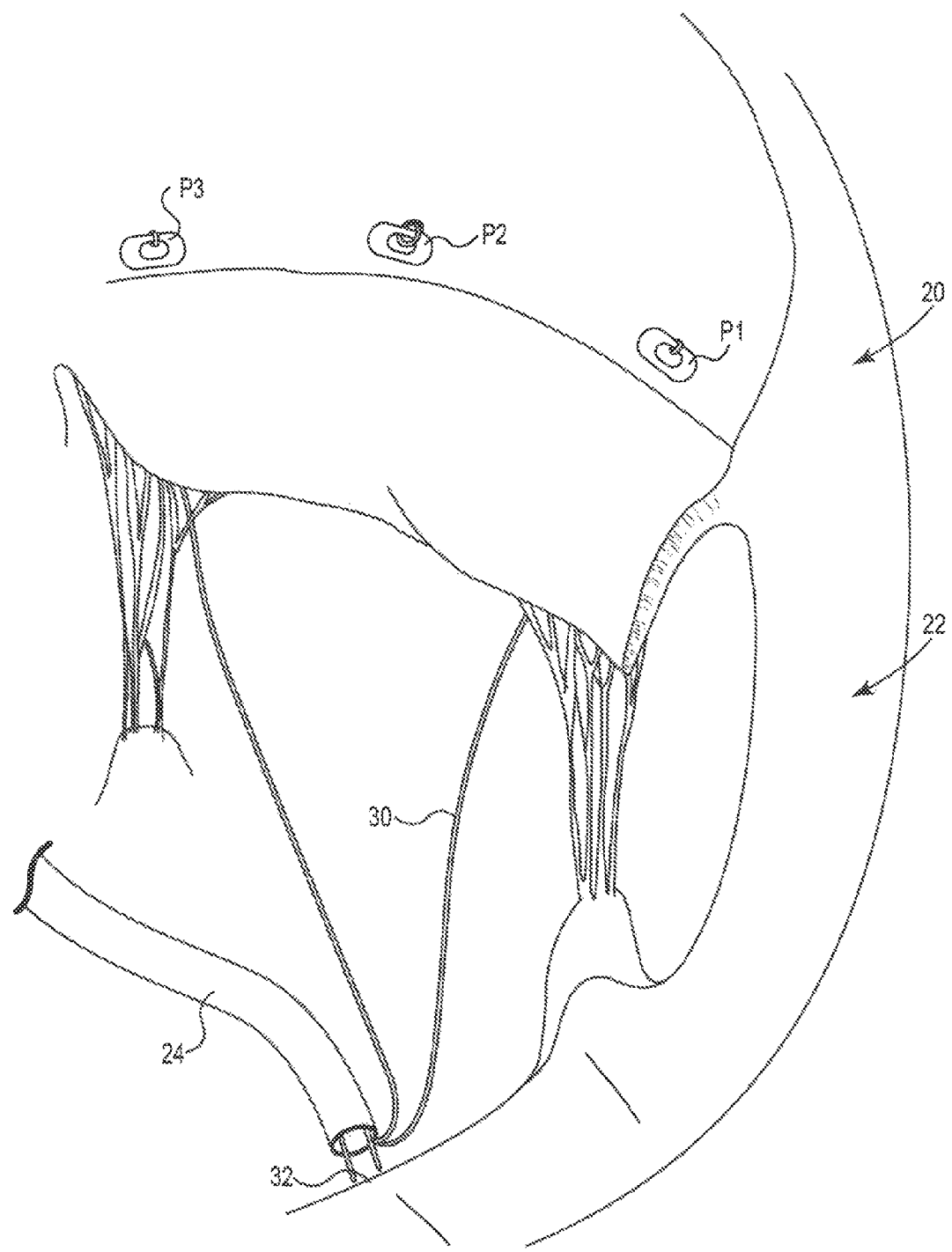
Figure 2C:
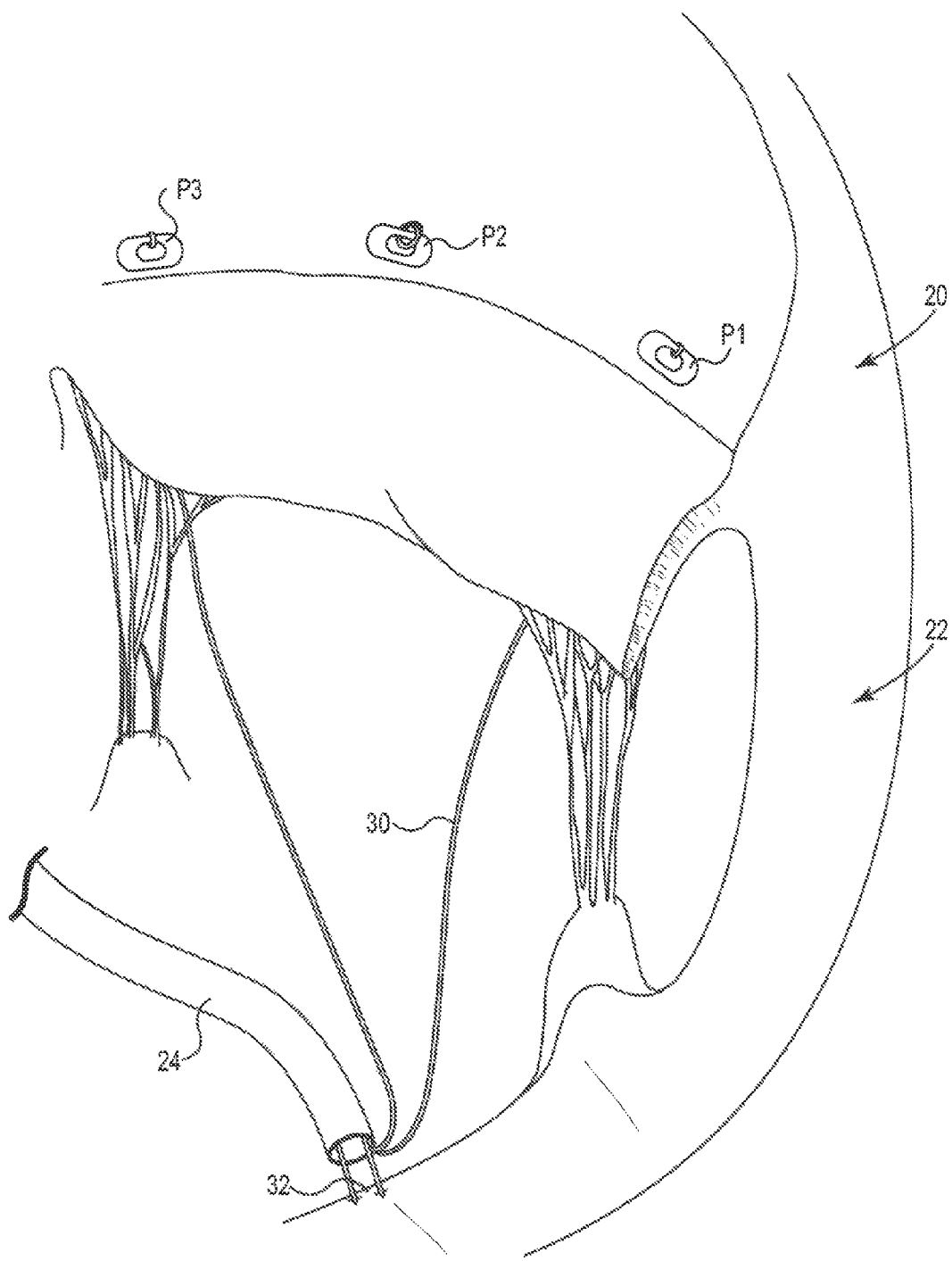
Figure 2D:
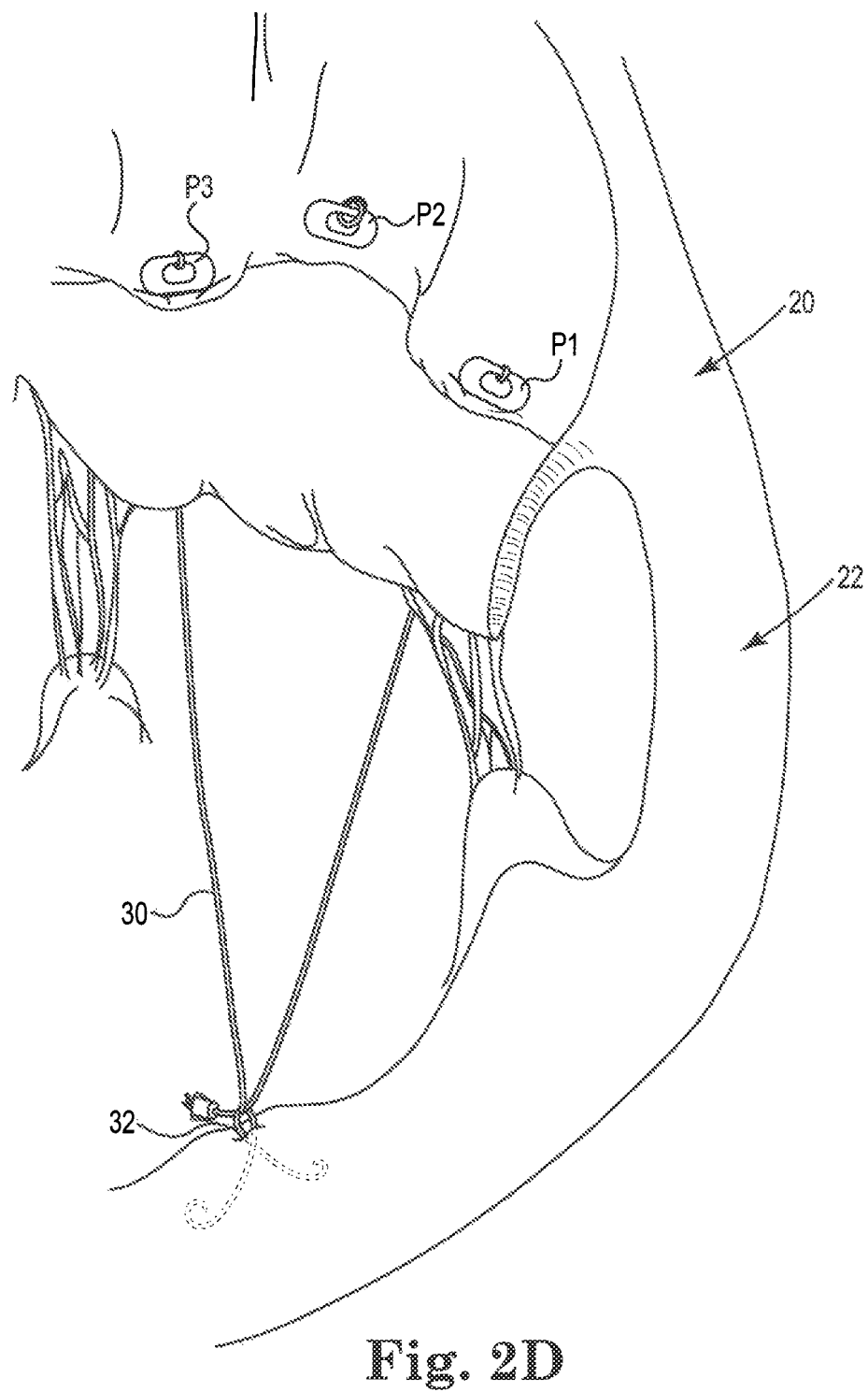

Reference is now made to FIGS. 2A-D, which are schematic illustrations of mitral valve 20 and left ventricle 22 being reshaped via a transaortic retrograde approach, in accordance with some applications of the present invention. As shown in FIG. 2A, for some applications, anchors P1, P2, and P3, and tether 30 are inserted into the subject's heart via a transaortic retrograde approach. The placement of the anchors is generally similar to that described hereinabove, with reference to FIGS. 1A-E, except that delivery catheter 24 is inserted via the aorta, rather than via the apex of the heart. Subsequent to the placement of the anchors, tether is pulled, and is anchored to anchoring location 32, which may be on the inner surface of the myocardium, for example, in the vicinity of the apex of the heart, as shown in FIGS. 2B-D.

Figure 3A:
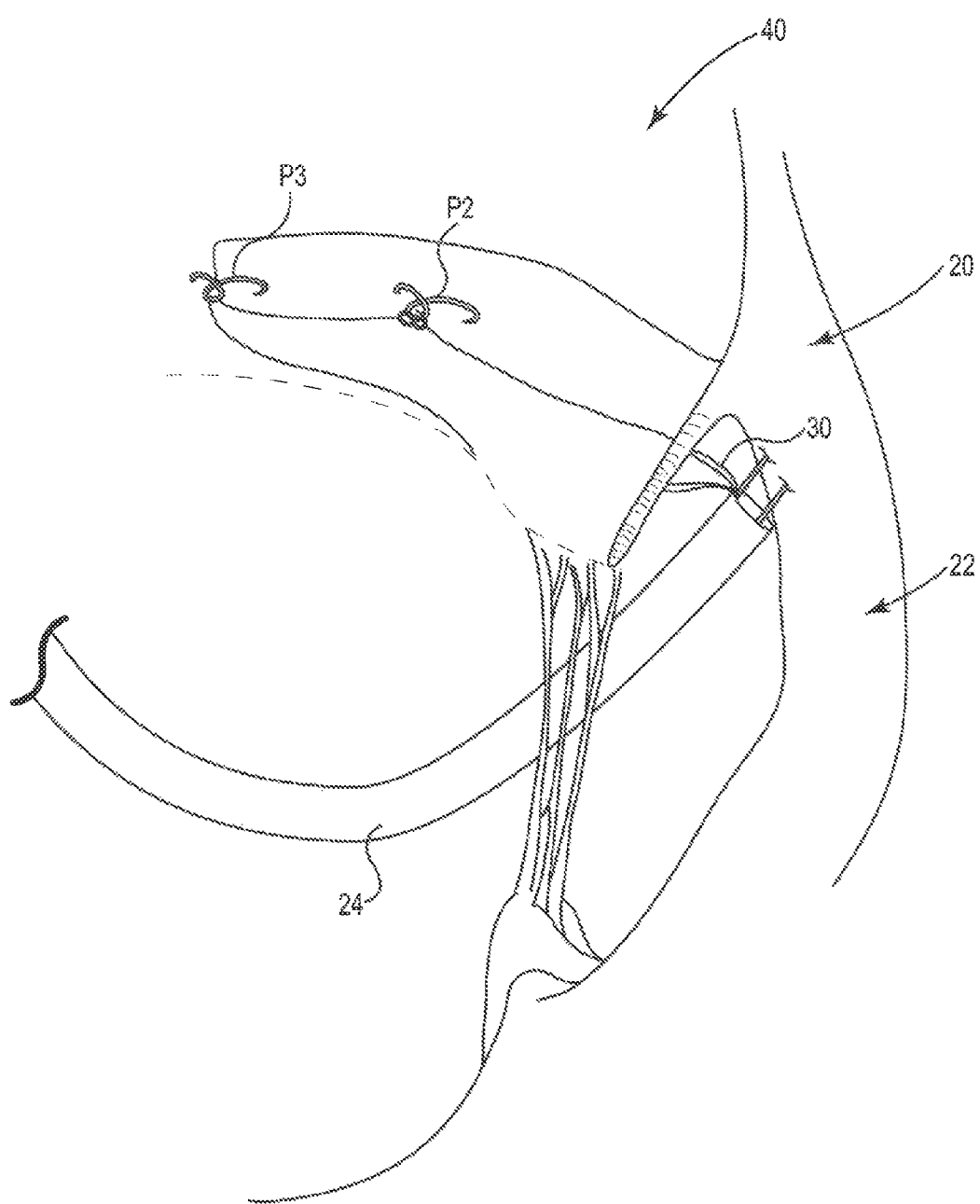
FIGS. 3A-E are schematic illustrations of a mitral valve and a left ventricle being reshaped using clips to anchor a tether to cardiac tissue, in accordance with some applications of the present invention.
Figure 3B:
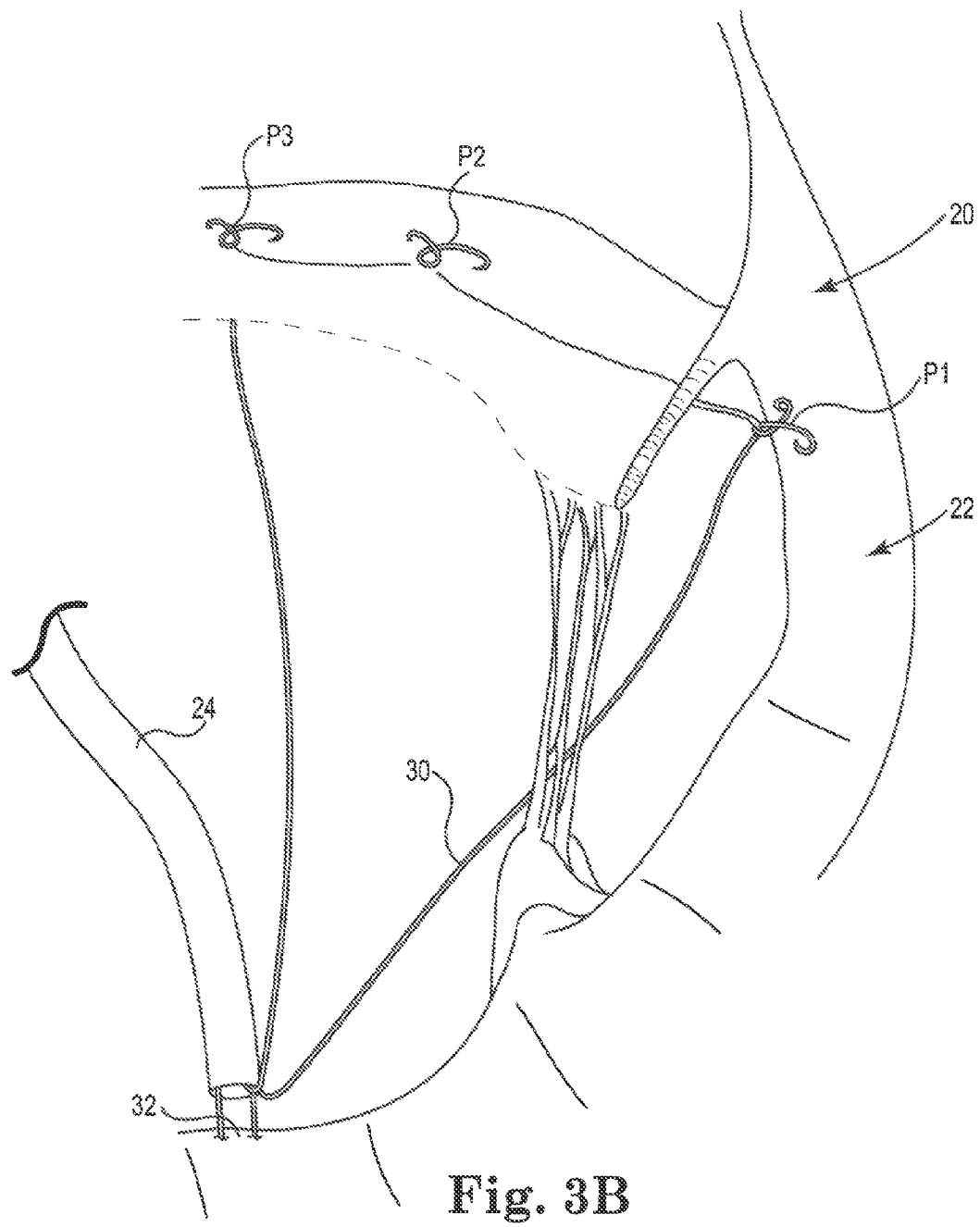
Figure 3C:
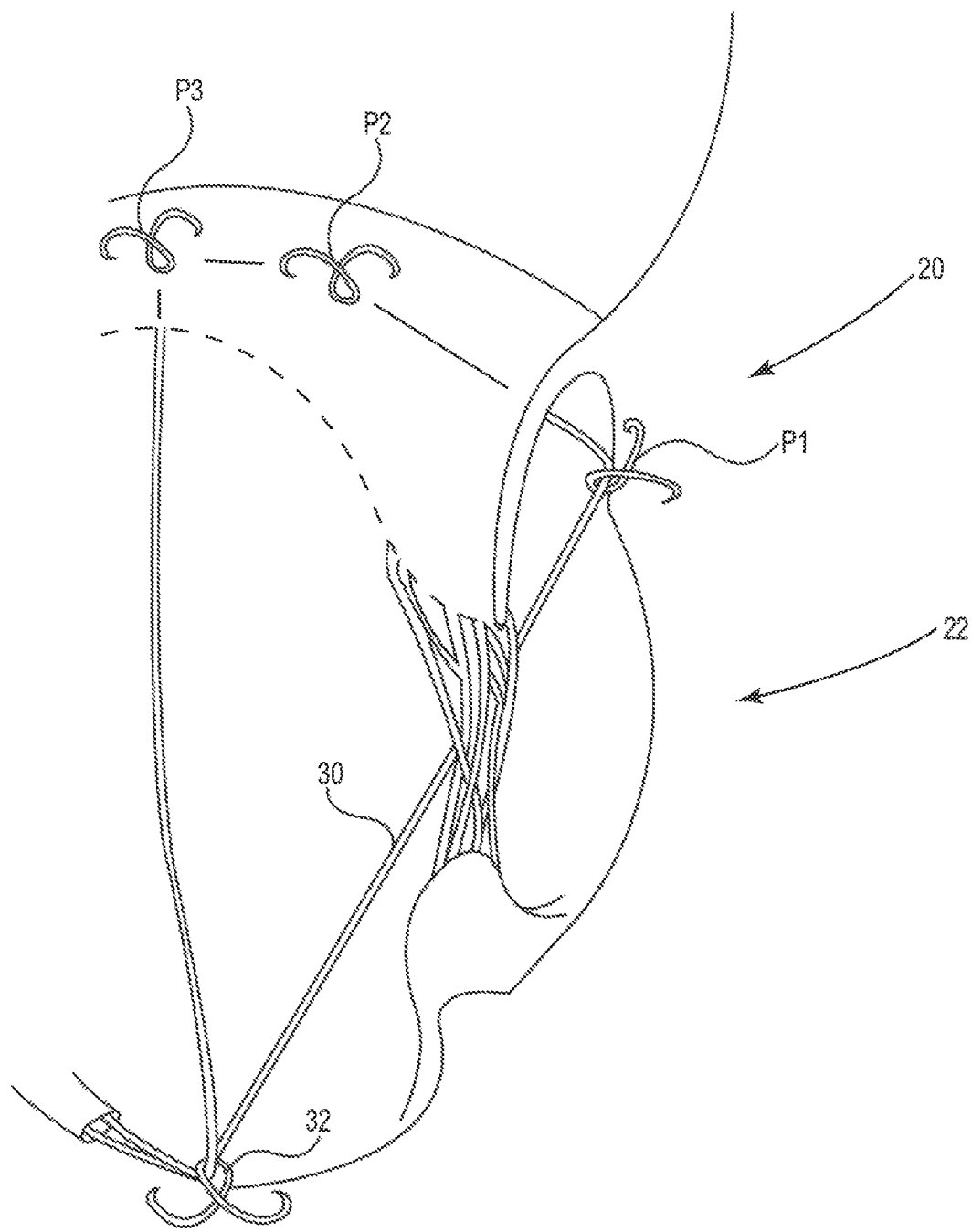
Figure 3D:
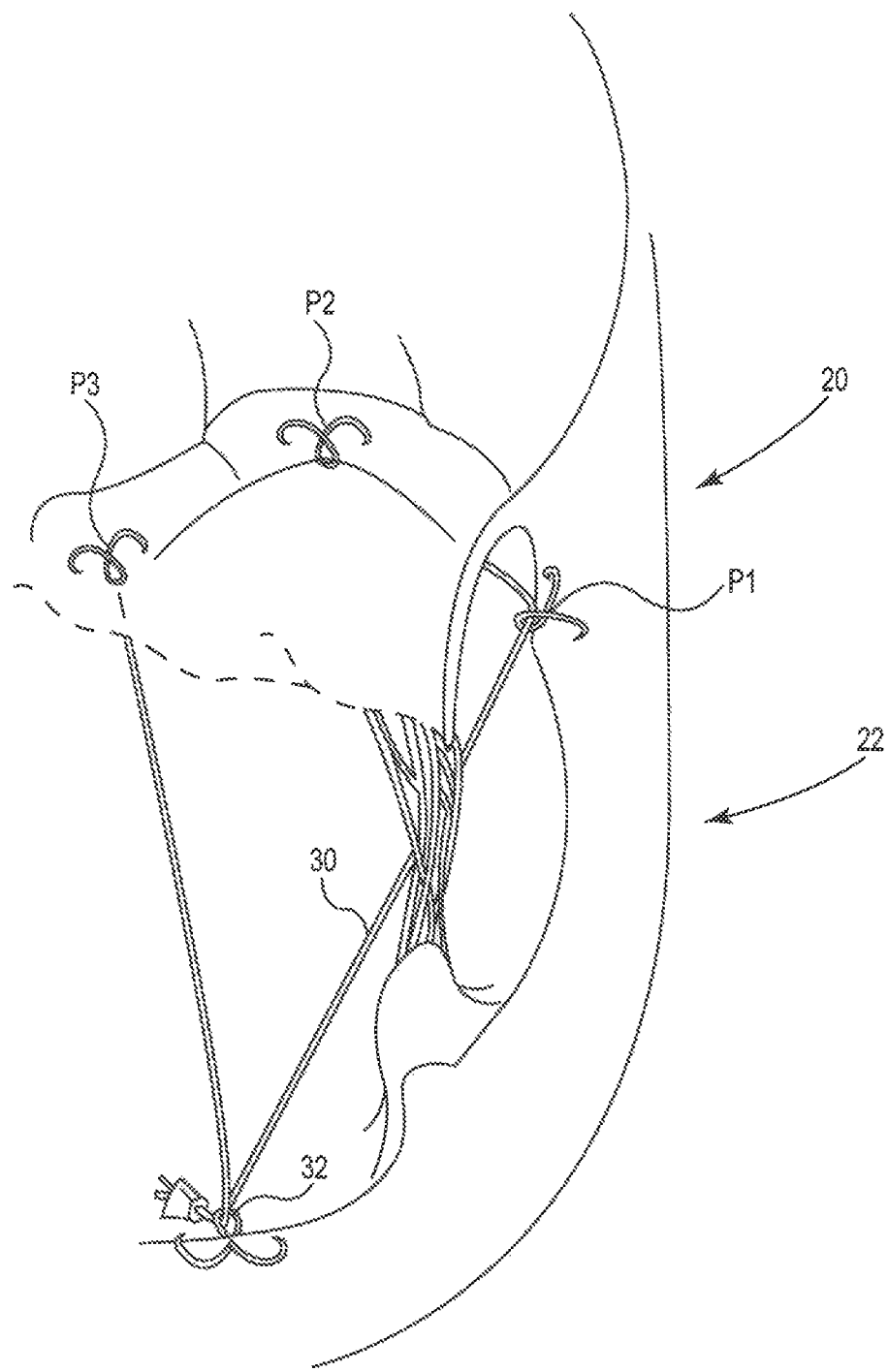

Reference is now made to FIGS. 3A-F, which are schematic illustrations of mitral valve 20 and left ventricle 22 being reshaped, using clips as the P1, P2, and P3 anchors, in accordance with some applications of the present invention. FIG. 3A-F shows the clips being used in a transaortic retrograde technique, although the clips can also be used in combination with the other techniques described herein, mutatis mutandis. Typically, delivery catheter 24 inserts the clips into tissue from a ventricular side of the valve. The clips are typically inserted such that the clips penetrate the tissue and the tips of the clips enter atrium 40. Tether 30 passes through the clips, and the ends of the tether are anchored to anchoring location, as described hereinabove, and as shown in FIGS. 3B-D.

Figure 3E:
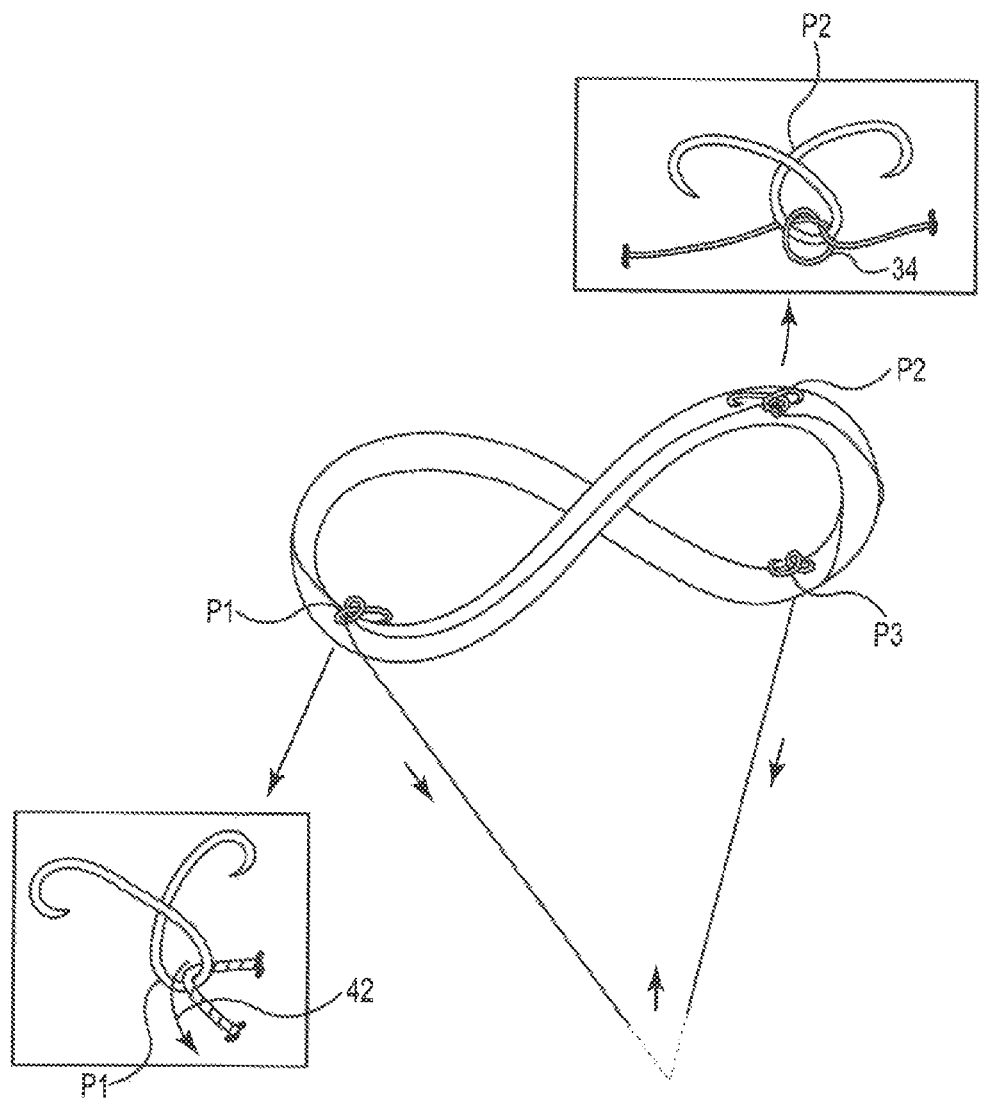

Typically, anchor P2 is fixedly coupled to tether 30, e.g., via knot 34, as shown in FIG. 3E. Further typically, the tether is slidably coupled to the P1 and P3 anchors, as indicated by arrow 42 in FIG. 3E. Thus, when the tether is pulled toward anchoring site 32, which is anterior and inferior to the posterior leaflet, anchors P1 and P3 slide toward anchor P2, and are pulled inferiorly with respect to anchor P2.

As described hereinabove, with reference to FIGS. 3A-E, for some applications, clips are inserted from the ventricle into the posterior mitral valve leaflet, such that the clips penetrate the leaflet. Alternatively, anchors are placed on the atrial side of the posterior mitral valve leaflet. For some applications, the anchors are placed on the atrial side of the posterior valve leaflet via a transmyocardial approach, in accordance with the techniques described with reference to FIGS. 4-7.

Figure 4A:
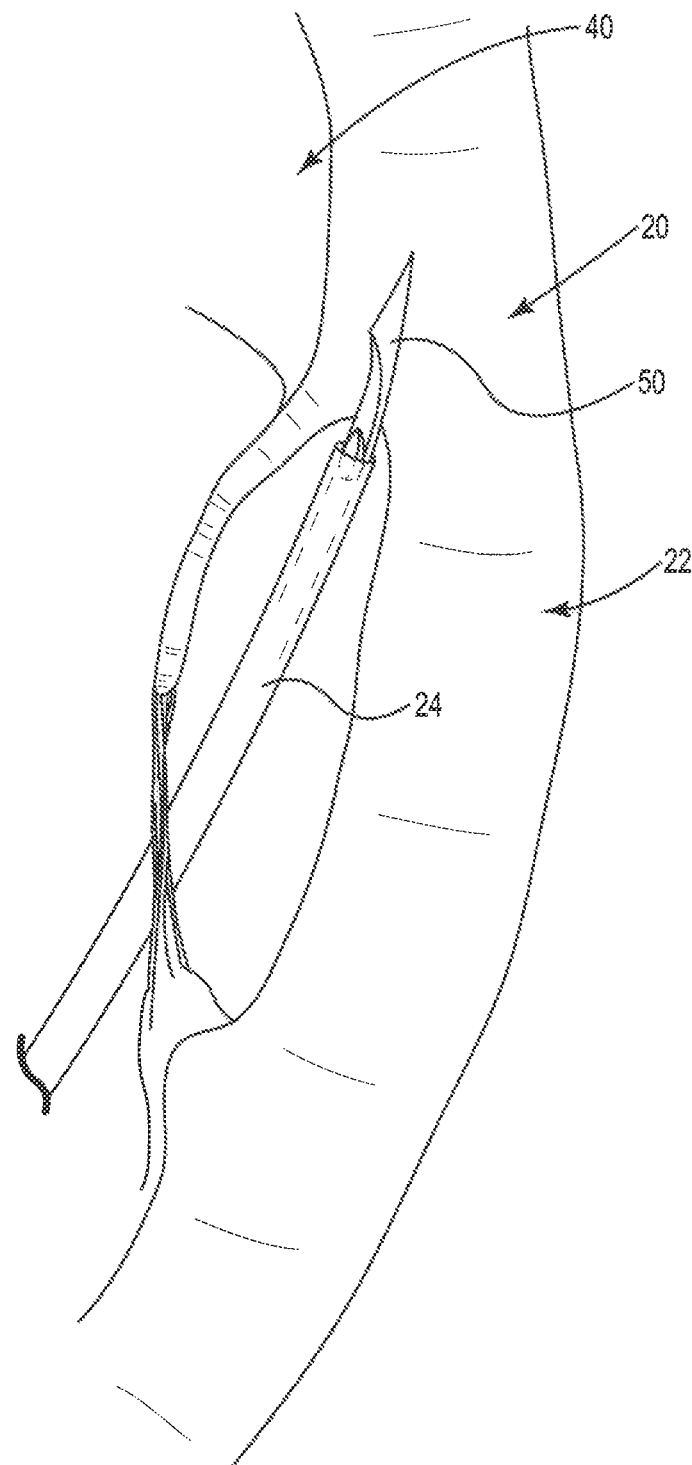
FIGS. 4A-C are schematic illustrations of anchors being applied to a vicinity of the posterior mitral valve leaflet via a transmyocardial approach, in accordance with some applications of the present invention.
Figure 4B:
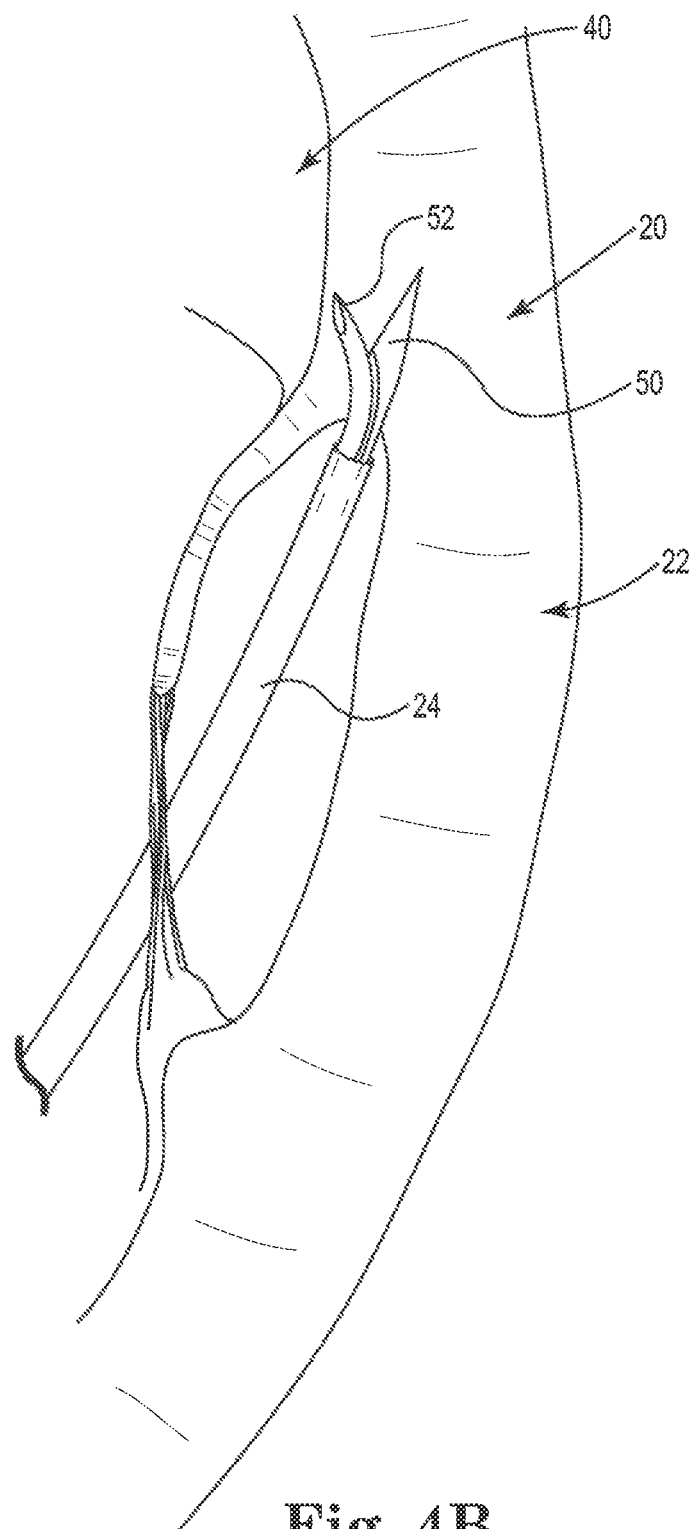
Figure 4C:
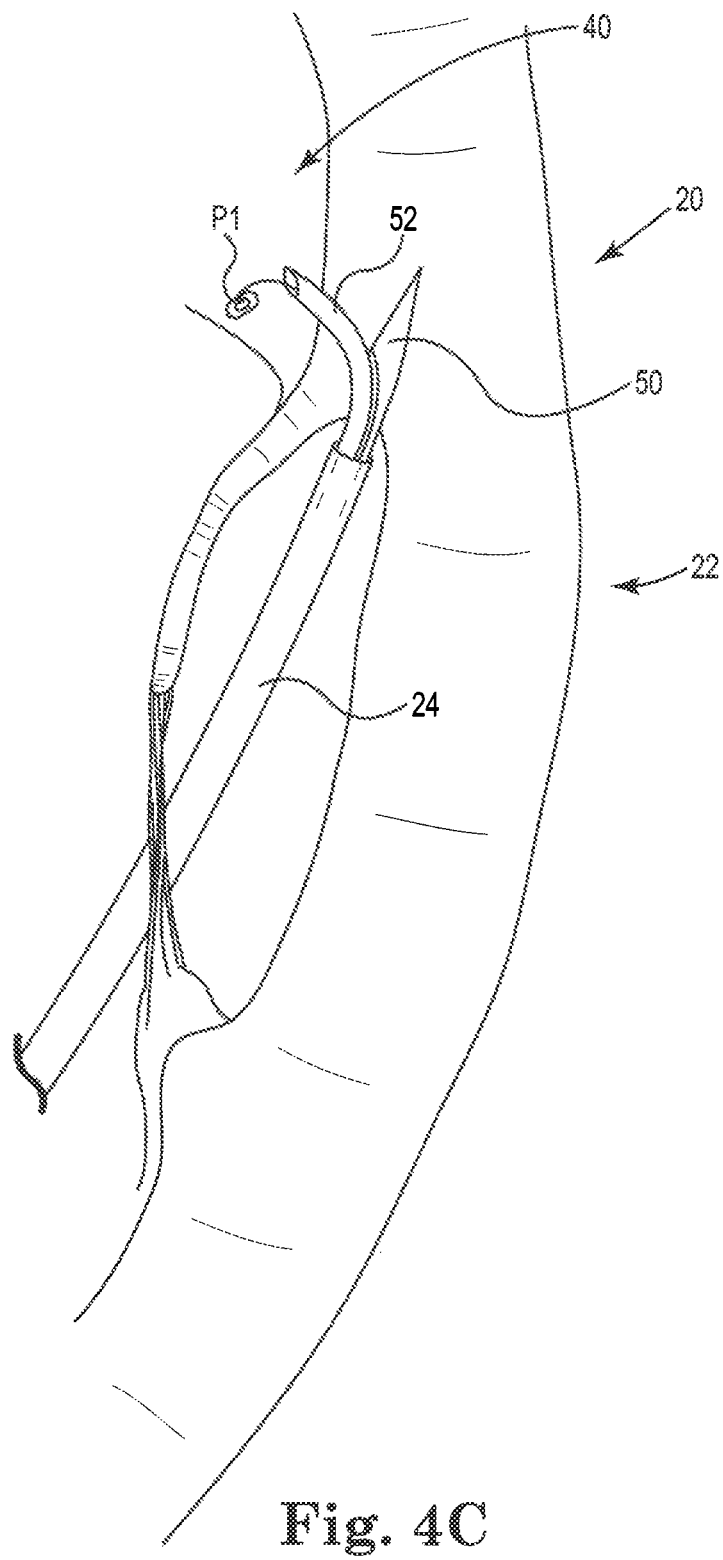

Reference is now made to FIGS. 4A-C, which are schematic illustrations of anchors P1, P2, and P3 being applied to tissue in the vicinity of the posterior mitral valve leaflet via a transmyocardial approach, in accordance with some applications of the present invention. A penetrating sheath 50 is inserted into the left ventricle, via delivery catheter 24. The penetrating sheath is advanced such that the sheath penetrates the myocardium, and the distal tip of the sheath is disposed in atrium 40, as shown in FIG. 4A. Subsequently, an anchor-delivery sheath 52 is advanced out of the distal end of penetrating sheath 50. The P1, P2 and P3 anchors are delivered and anchored to atrial tissue that is in the vicinity of (e.g., on or posterior to) the posterior leaflet of the mitral valve, via the anchor-delivery sheath. FIG. 4C illustrates the delivery and placement of the P1 anchor via anchor-delivery sheath 52.

Figure 5A:
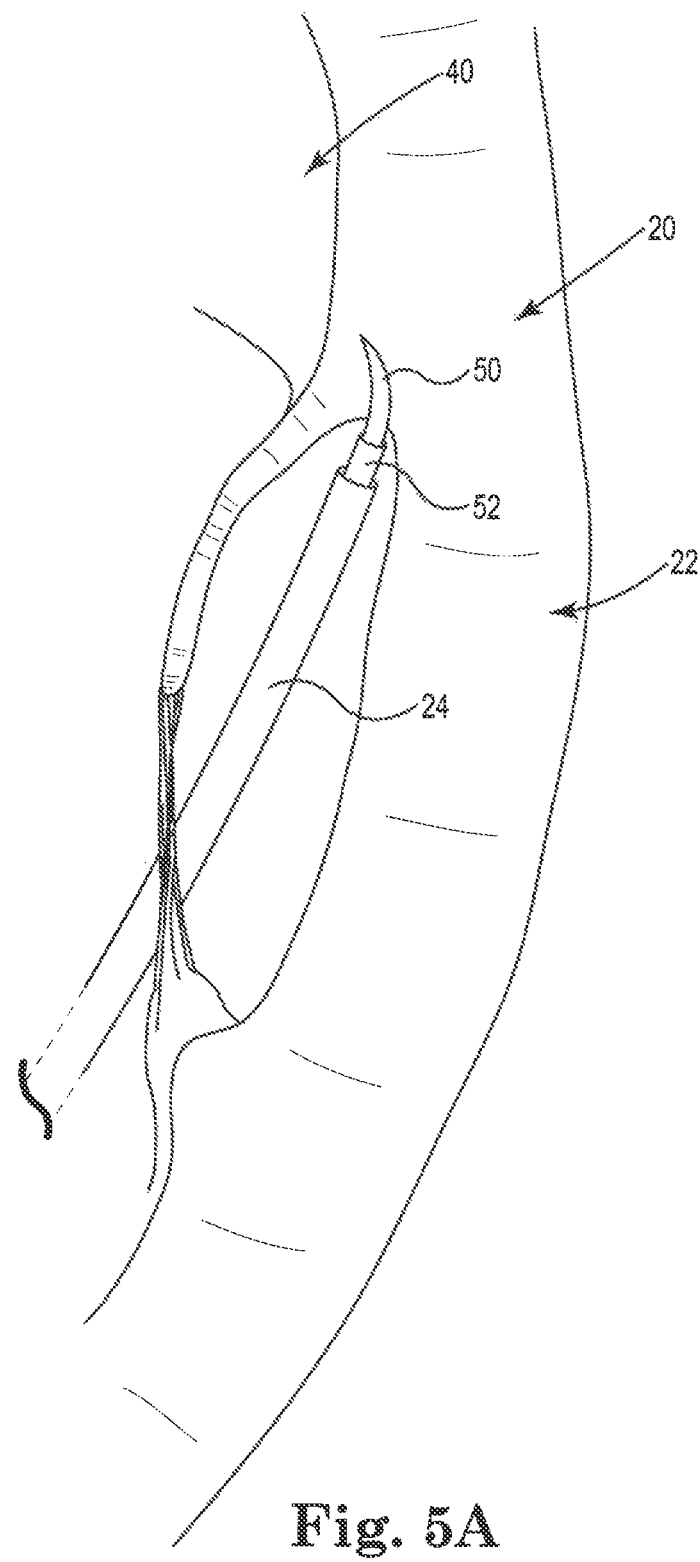
FIGS. 5A-D are schematic illustrations of anchors being applied to a vicinity of the posterior mitral valve leaflet via a transmyocardial approach, in accordance with alternative applications of the present invention.
Figure 5B:
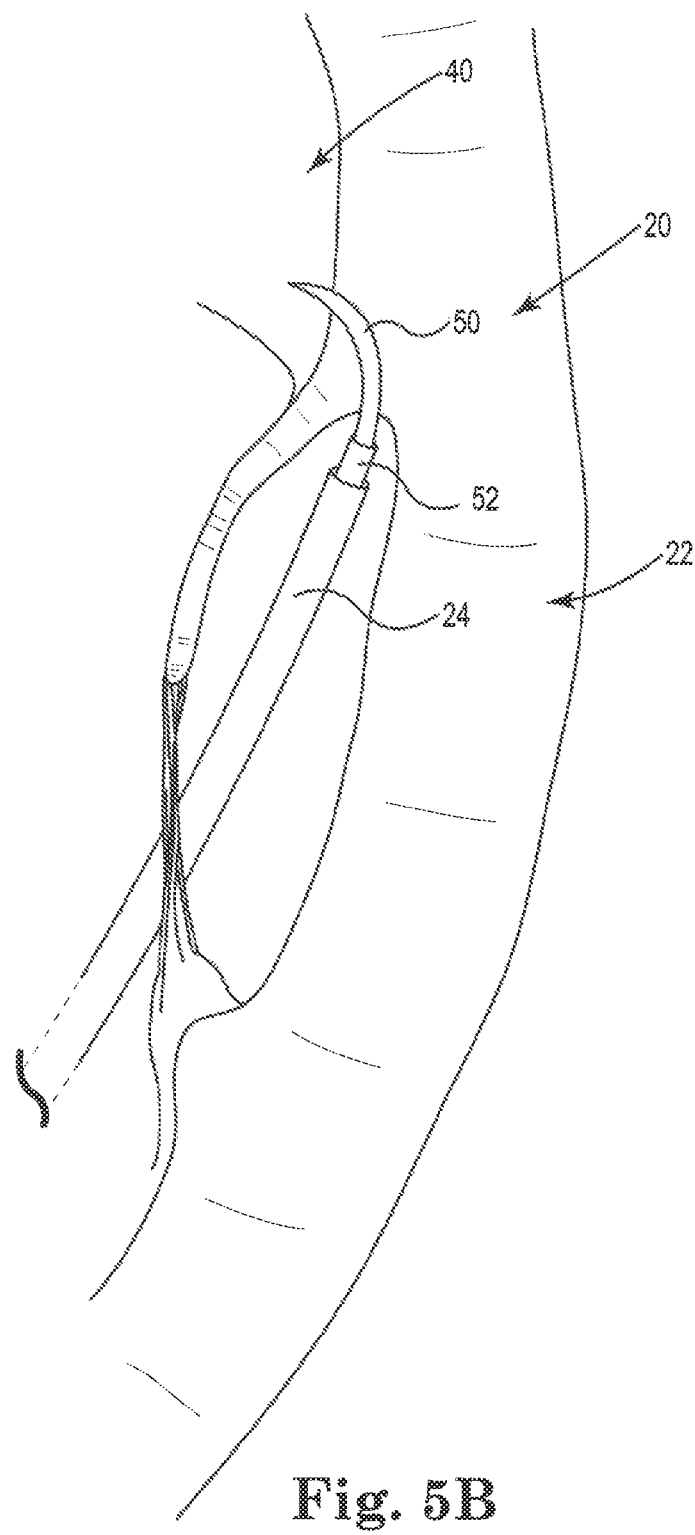
Figure 5C:
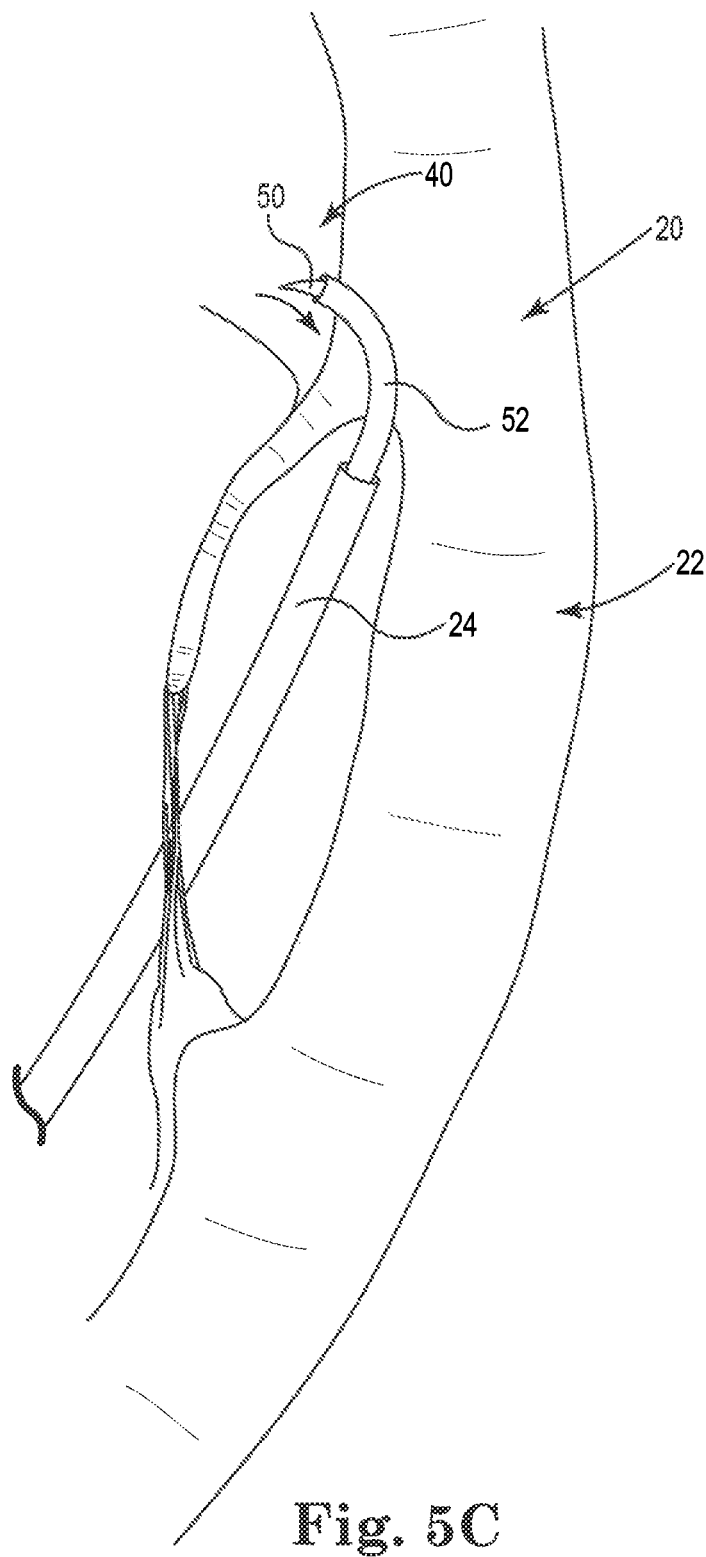
Figure 5D:
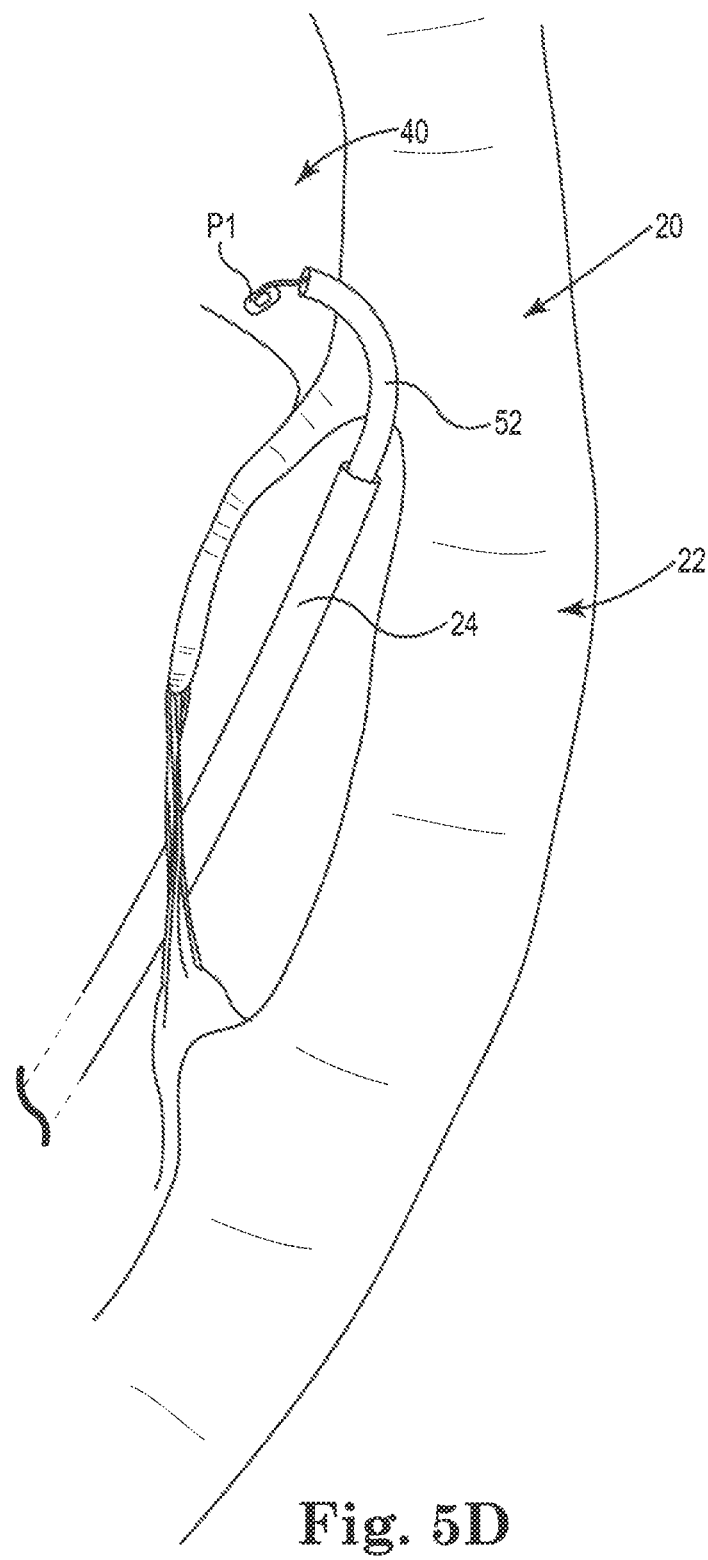

Reference is now made to FIGS. 5A-D, which are schematic illustrations of anchors P1, P2, and P3 being applied to tissue in the vicinity of the posterior mitral valve leaflet via a transmyocardial approach, in accordance with alternative applications of the present invention. For some applications, penetrating sheath 50 is inserted into left ventricle 22 via anchor-delivery sheath 52, which, in turn, is inserted via delivery catheter 24, as shown in FIG. 5A. The penetrating sheath is advanced such that the sheath penetrates the myocardium, and the distal tip of the sheath is disposed in atrium 40, as shown in FIG. 5B. Subsequently, penetrating sheath is withdrawn from anchor-delivery sheath 52 (shown in FIG. 5C), and the anchors are delivered to the left atrium via the anchor-delivery sheath. FIG. 5D illustrates the delivery and placement of the P1 anchor via anchor-delivery sheath 52.

Figure 6A:
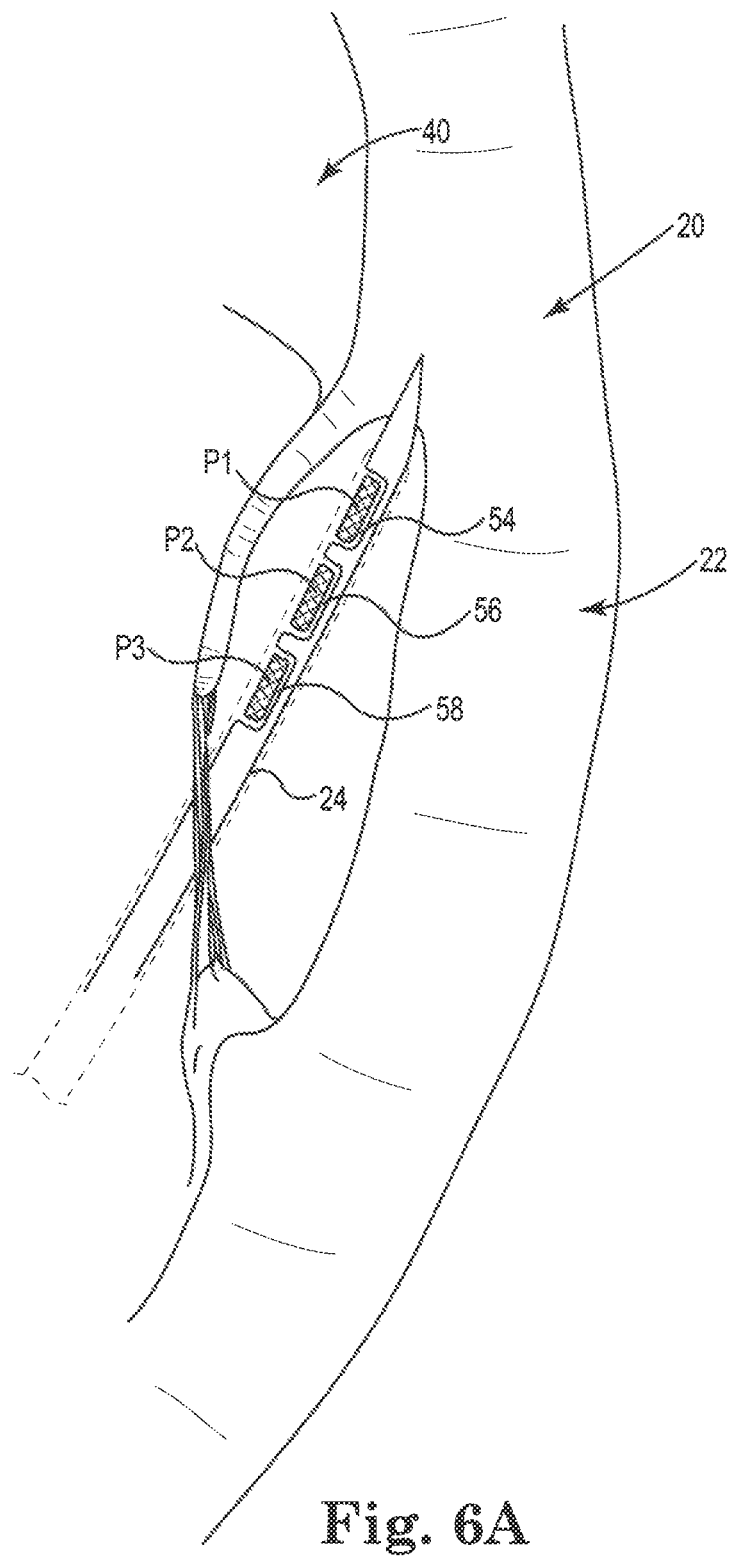
FIGS. 6A-C are schematic illustrations of anchors being applied to a vicinity of the posterior mitral valve leaflet via a transmyocardial approach, in accordance with further alternative applications of the present invention.
Figure 6B:
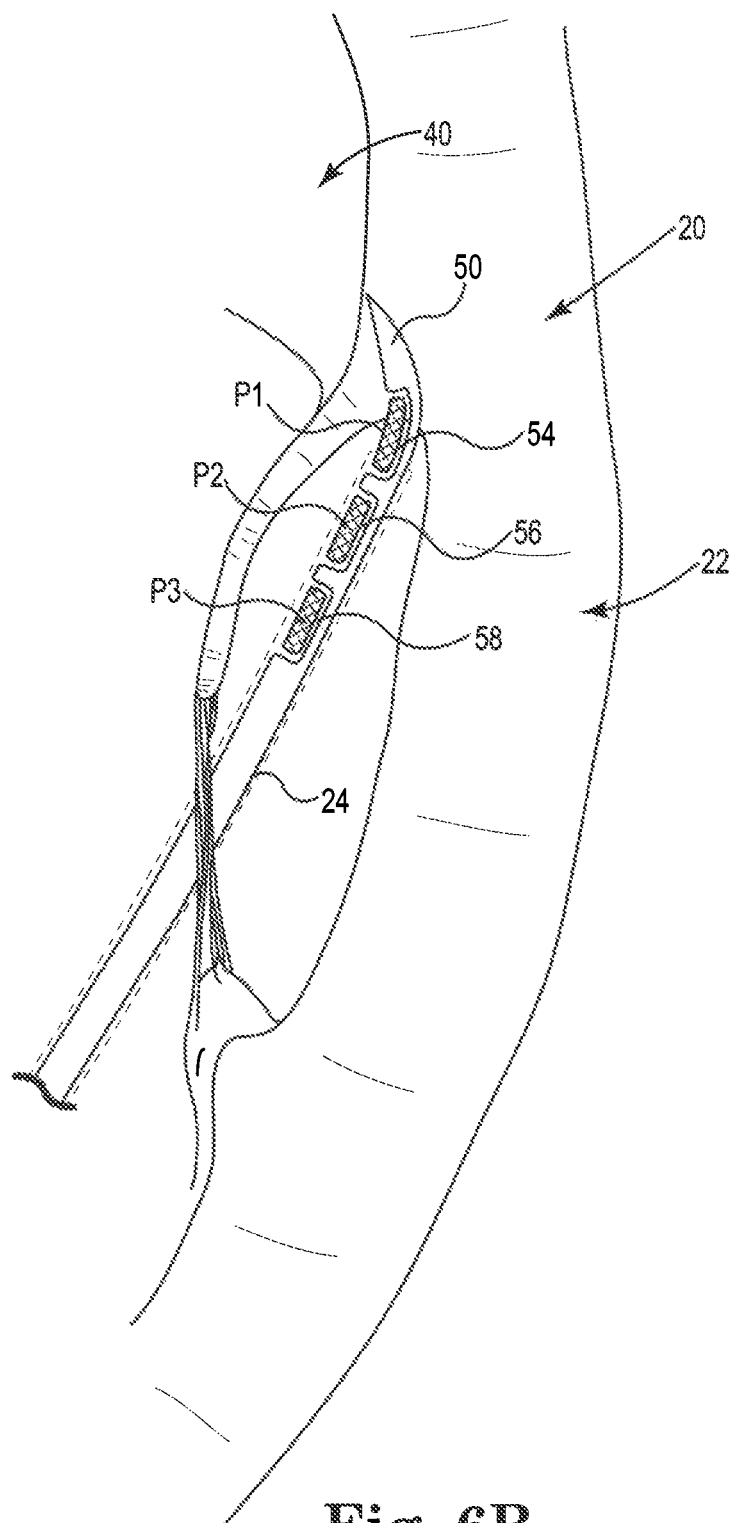
Figure 6C:
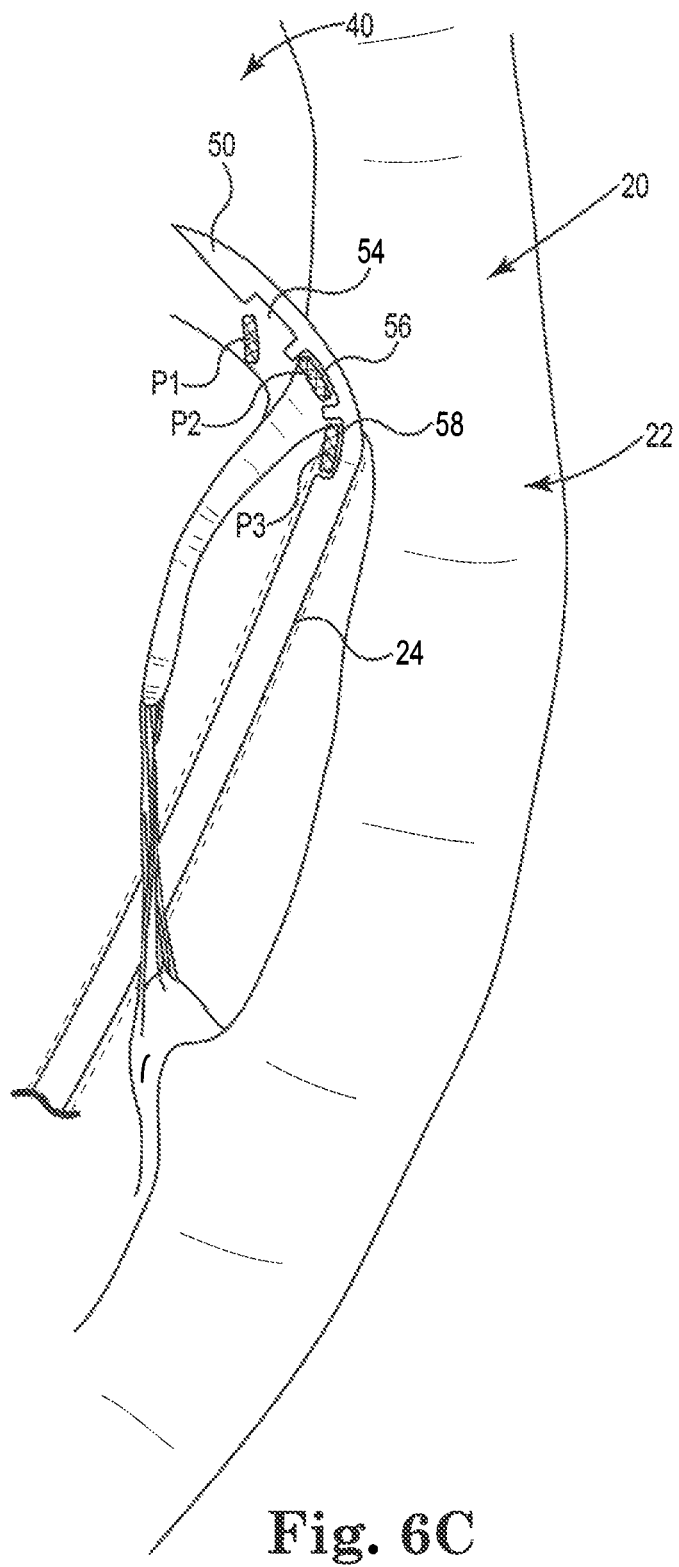

Reference is now made to FIGS. 6A-C, which are schematic illustrations of anchors P1, P2, and P3 being applied to the posterior mitral valve leaflet via a transmyocardial approach, in accordance with further alternative applications of the present invention. For some applications, a single sheath 50 penetrates the myocardium, and delivers the anchors to the tissue of the left atrium. As shown in FIGS. 6A-C, for some applications, penetrating sheath 50 defines openings 54, 56, and 58, via which, respectively, P1, P2, and P3 anchors are delivered. The distal tip of the penetrating sheath is advanced from the distal end of delivery catheter 24, such that the penetrating sheath penetrates the myocardium, as shown in the transition from FIG. 6A-6B. Subsequently, the penetrating sheath is advanced, such that opening 54 is facing tissue in the vicinity of the P1 segment of the posterior leaflet of mitral valve 20. Anchor P1 is anchored to the aforementioned tissue, via opening 54, as shown in FIG. 6C. Subsequently, P2 and P3 anchors are anchored to tissue in the vicinity of, respectively, the P2 and P3 segments of the posterior leaflet of mitral valve 20, via openings 56 and 58 (not shown).

Figure 7:
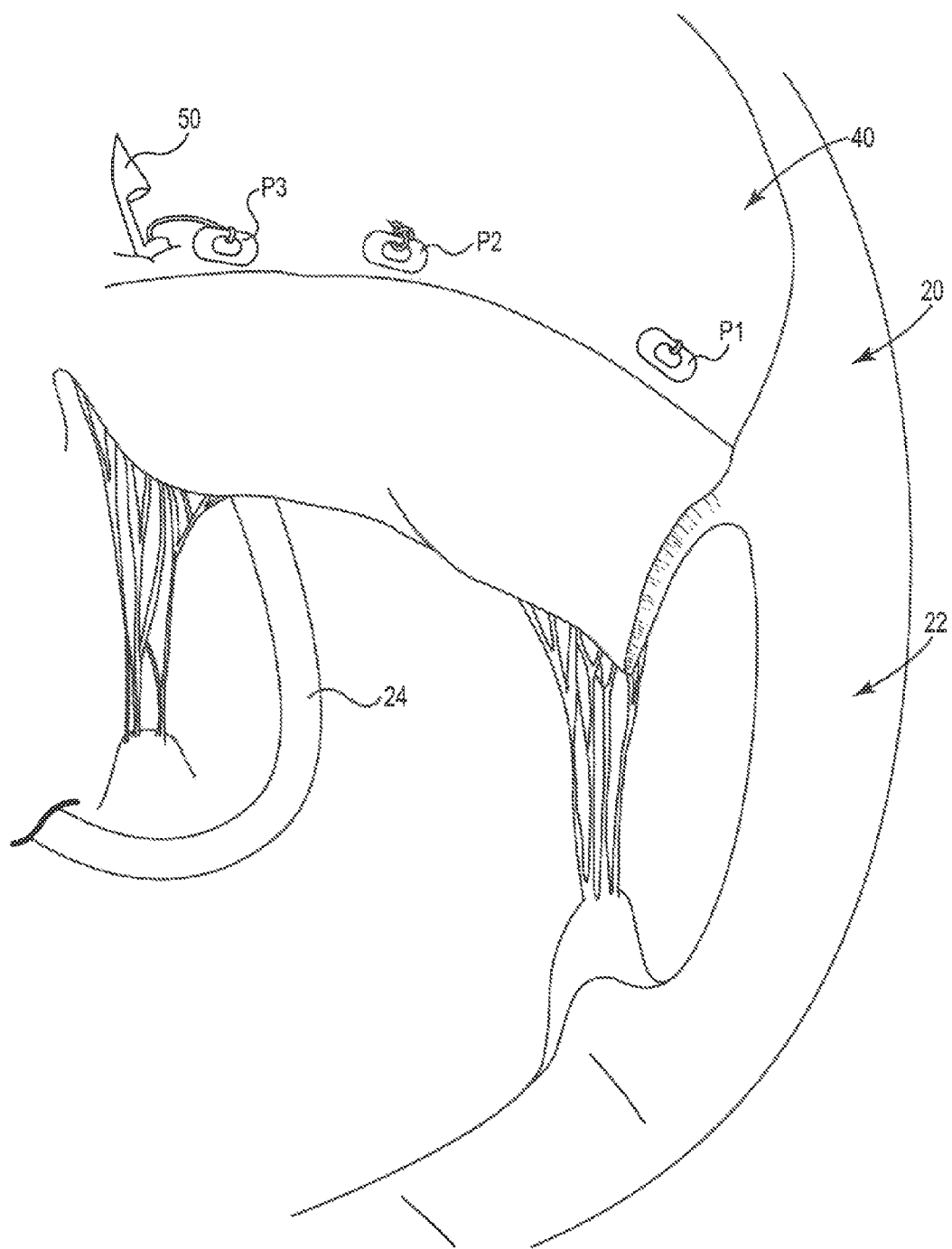
FIG. 7 is a schematic illustration of anchors being applied to a vicinity of the posterior mitral valve leaflet via a transaortic retrograde transmyocardial approach, in accordance with some applications of the present invention.

Reference is now made to FIG. 7, which is a schematic illustration of anchors P1, P2, and P3 being applied to tissue in the vicinity of the posterior mitral valve leaflet via a transaortic retrograde transmyocardial approach, in accordance with some applications of the present invention. It is noted that in the techniques described hereinabove, with reference to FIGS. 4-6, penetrating sheath is inserted into the atrium via a penetration site that is in the vicinity of the anterior commissure of the mitral valve. Anchor-delivery sheath 52 or penetrating sheath 50 is then advanced from the aforementioned penetration site to the P1, P2 and P3 segments of the posterior mitral valve. For alternative applications, penetrating sheath 50 penetrates the myocardium at a penetrating site that is in the vicinity of the posterior commissure of the mitral valve, as shown in FIG. 7. In all other respects delivery of the anchors via the penetrating sheath (and, optionally, via the anchor-delivery sheath) is generally in accordance with the techniques described with reference to FIGS. 4-6.

Figure 8A:
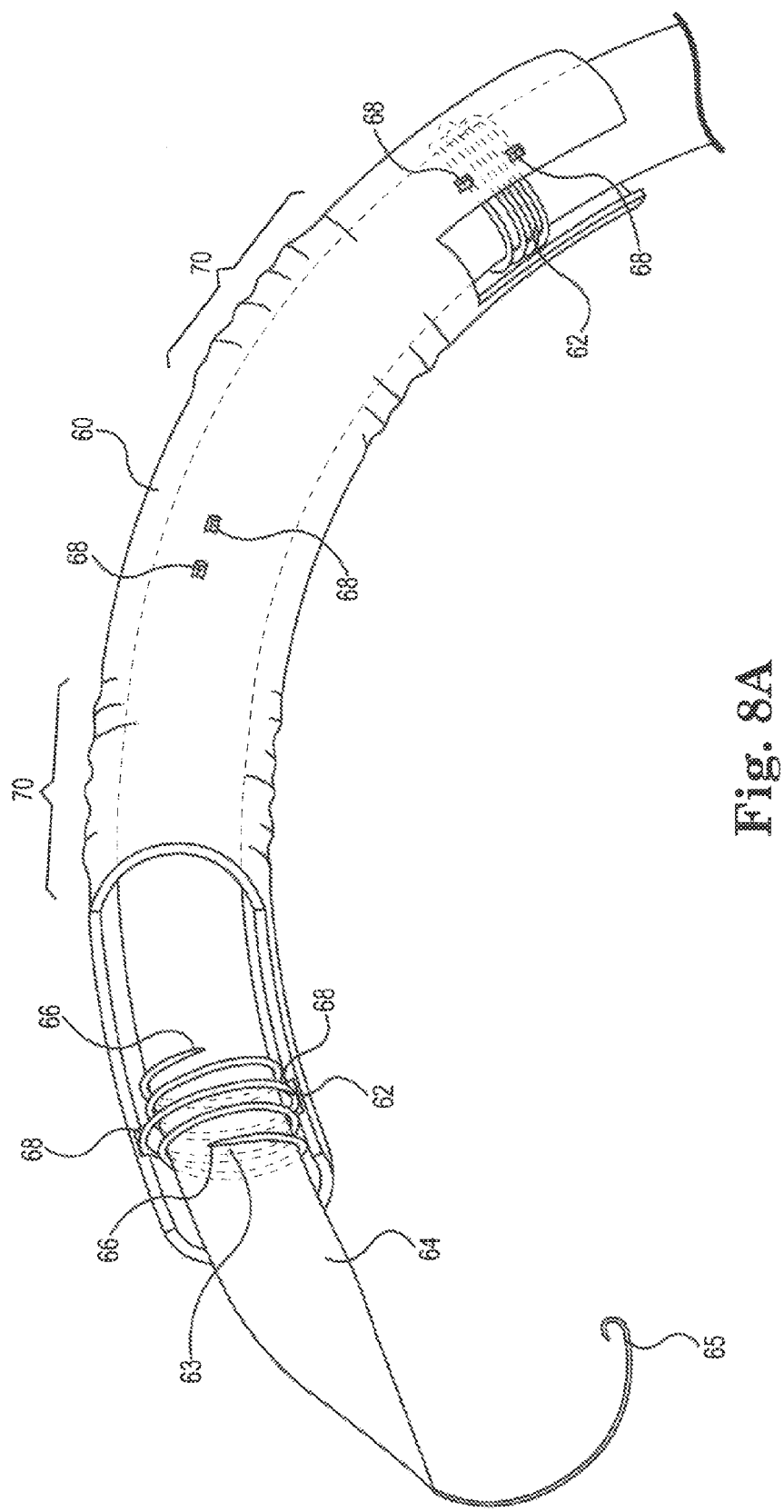

Reference is now made to FIGS. 8A-H, which are schematic illustrations of a mitral ring 60, self-suturing anchors 62 being disposed inside the mitral ring, in accordance with some applications of the present invention. Mitral ring 60 is typically made of a polymer, a plastic, titanium, stainless steel, and/or other similar materials. Anchors 62 are elongate elements that are shaped to define openings 63. A mandrel 64 is reversibly disposed through the openings, as shown in FIGS. 8A-B. In response to the mandrel being withdrawn from the openings, ends 66 of the anchors automatically move outwardly, via openings 68 in the mitral ring (typically, due to the anchors being elastically loaded), as shown in FIG. 8C.

Typically, while mandrel 64 is disposed inside openings 63 defined by anchors 62, the anchors are placed adjacent to tissue that is in the vicinity of the mitral valve (or other tissue as described hereinbelow). In response to the mandrel being withdrawn from the openings, ends 66 of the anchors move outwardly, thereby entering the tissue. Ends 66 are typically sharp, so as to facilitate penetration of the tissue. For some applications, in response to mandrel being reinserted via the openings that are defined by the anchors, the anchors exit the tissue via exit routes that are the reverse of the entry routes of the anchors. Thus, if the anchors have been inaccurately placed, the anchors may be removed from the tissue without causing an additional wound to the tissue, during the removal of the anchors. Typically, a guidewire 65 passes through openings 63, and the mandrel is advanced and withdrawn over the guidewire. Thus, the guidewire facilitate reinsertion if the mandrel via the openings, if necessary. Typically, a tether (e.g., tether 30 described hereinabove) passes through the anchors, and is used to tether the anchors to each other.

It is noted that for some applications, mitral ring 60 includes flexible regions 70 between adjacent anchors. The function of the flexible regions is described in further detail hereinbelow.

Figure 8E:
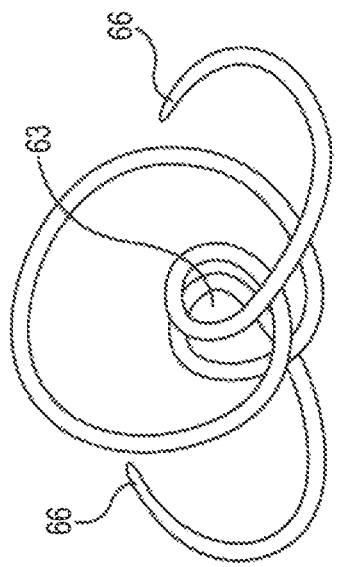
Figure 8D:
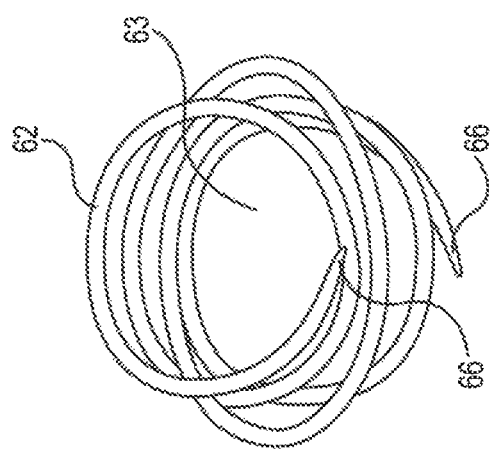
Figure 8F:
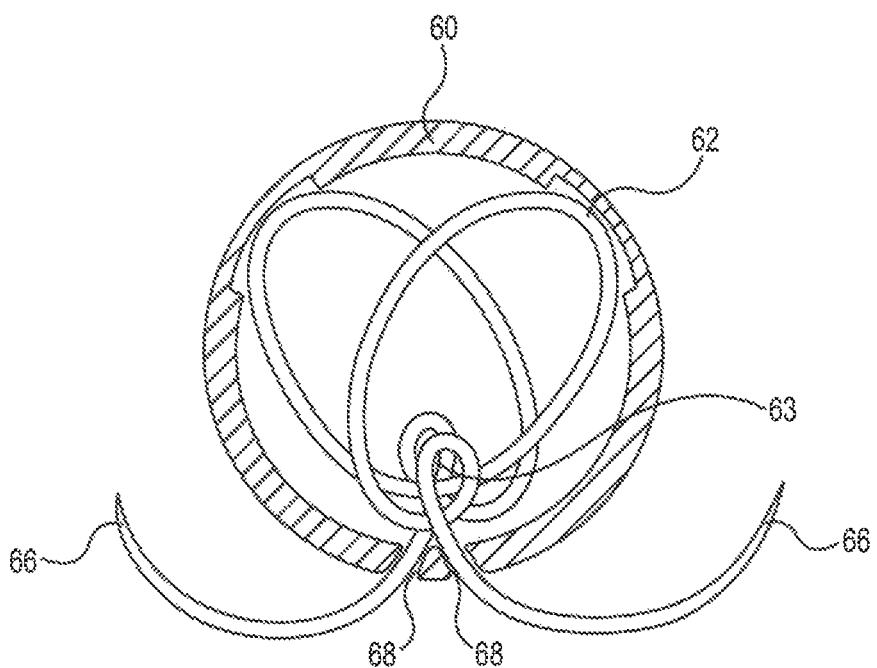

FIGS. 8D, 8E, and 8F show a single anchor, respectively, configured as when the mandrel is inserted through opening 63 (FIG. 8D, mandrel not shown), configured as when the mandrel is removed from opening 63 (FIG. 8E), and disposed inside mitral ring 60 (FIG. 8F). It is noted that even in the configuration shown in FIG. 8E (i.e., as when mandrel 64 has been withdrawn), the anchor defines an opening 63, via which the mandrel can be reinserted.

Figure 8G:
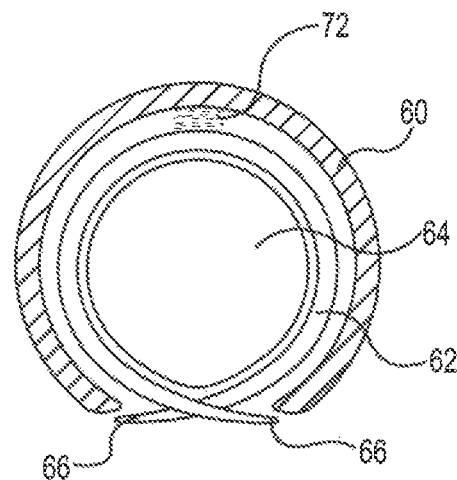
Figure 8H:
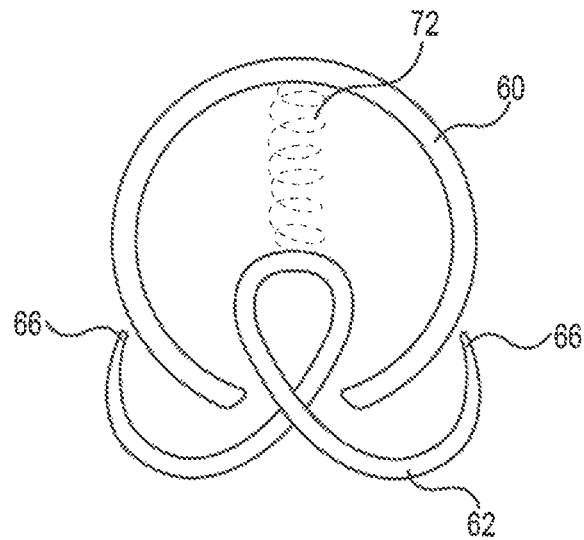

FIGS. 8G-H are schematic illustrations that demonstrate the principle by which self-suturing anchors operate. Each anchor is configured such that when mandrel 64 is inserted via opening 63, the anchor is elastically loaded, i.e., it is as if there was a loaded spring 72 (shown in dashed lines in FIGS. 8G-H) disposed above the anchor. The spring is prevented from expanding by the mandrel. Upon removal of the mandrel from opening, the spring is released, thereby causing the diameter of opening 63 to decrease, and pushing ends 66 outward.

For some applications, the anchors comprise a shape-memory alloy, such as nitinol. Each anchor is shaped in the closed configuration of the anchor. The mandrel is inserted through the opening in the anchor, such that the shape-memory alloy is biased open. Thus, insertion of the mandrel through the opening causes the anchor to become elastically loaded. Upon removal of the mandrel from the opening of the anchor, the anchor reverts to the closed shape thereof.

For some applications, the anchors comprise a metal, such as stainless steel. Each anchor is shaped into the closed configuration of the anchor and becomes elastically loaded due to the insertion of the mandrel through the opening in the anchor, as described hereinabove.

Figure 9A:
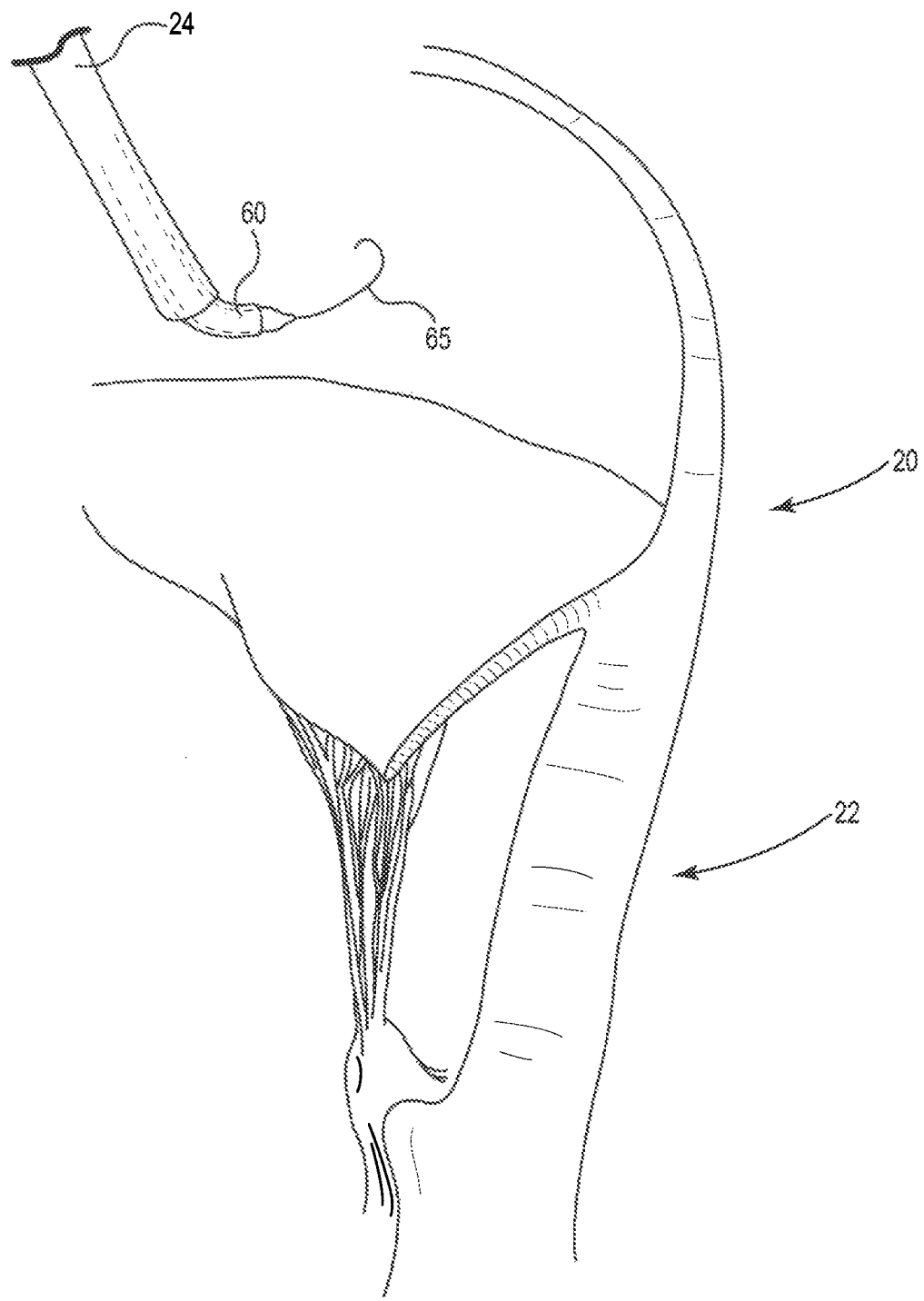
FIGS. 9A-I are schematic illustrations of the mitral ring being implanted on the atrial side of the posterior mitral valve, in accordance with some applications of the present invention.
Figure 9B:
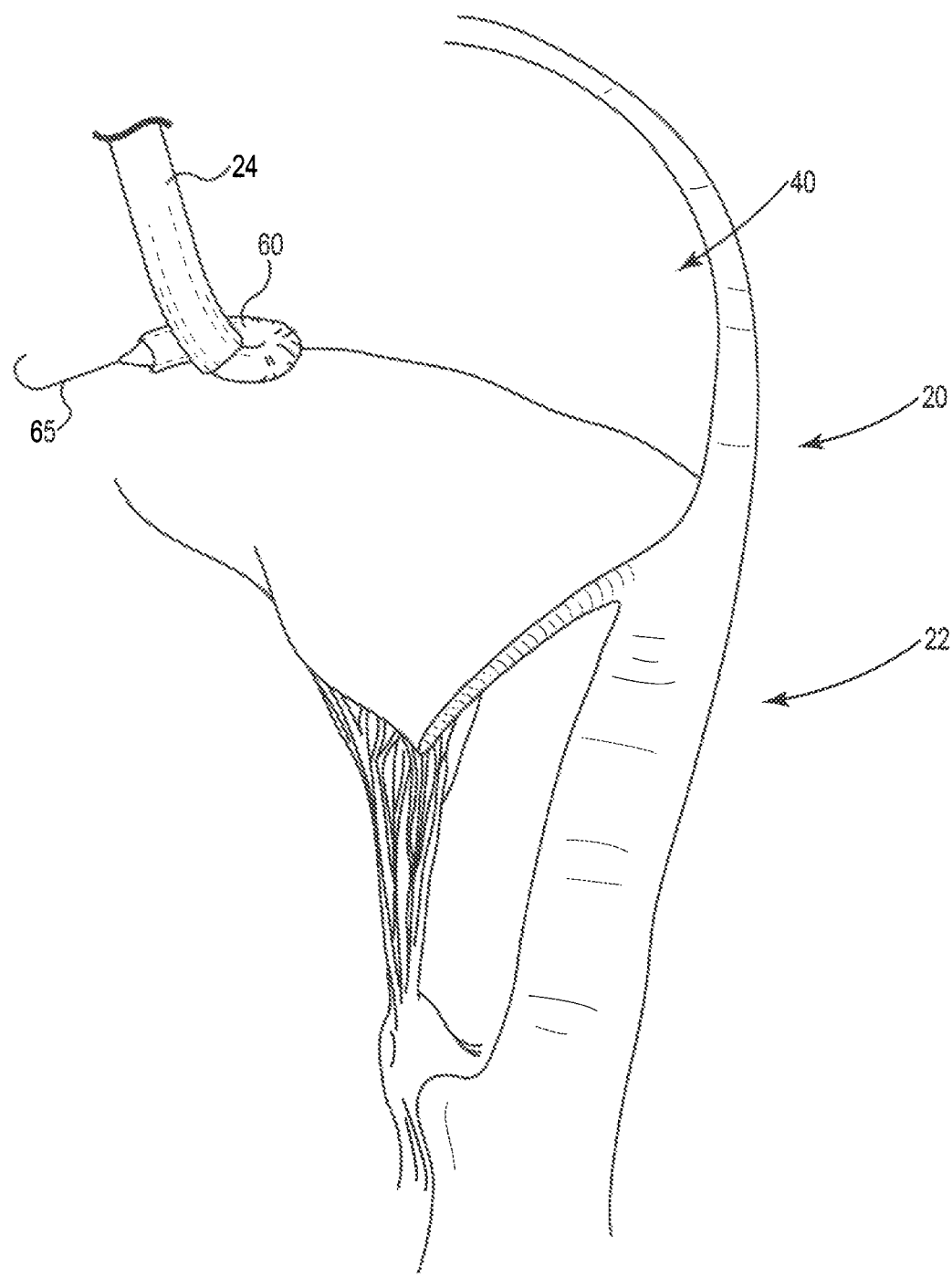
Figure 9C:
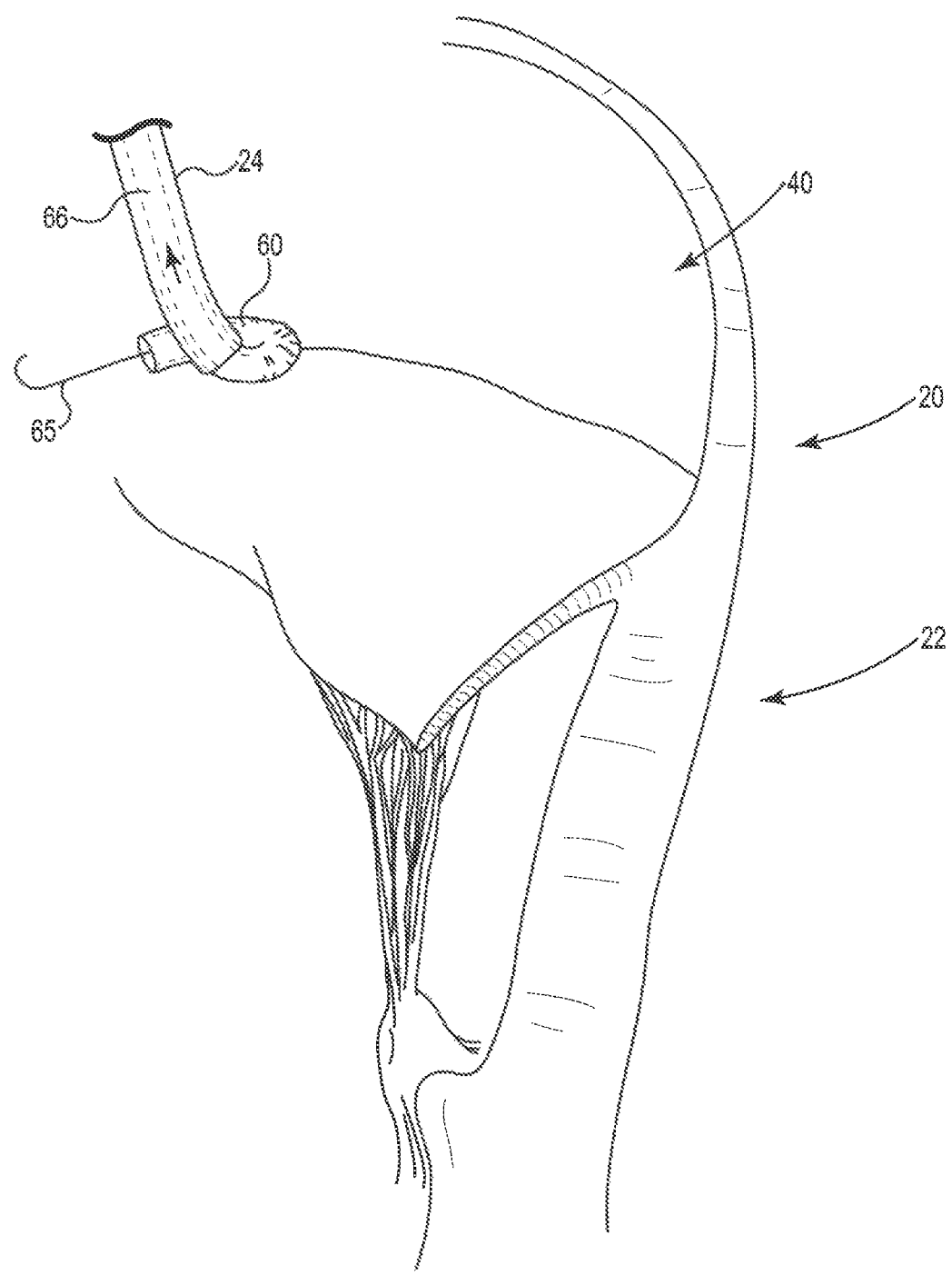

Reference is now made to FIGS. 9A-I, which are schematic illustrations of mitral ring 60 being implanted on the atrial side of the posterior mitral valve, in accordance with some applications of the present invention. For some applications, mitral ring is inserted into left atrium 40 via delivery catheter 24 (FIG. 9A), via the inter-atrial septum, as shown. Alternatively, the mitral ring is inserted directly into the atrium (e.g., via a minimally invasive surgical approach). The most distal of self suturing anchors 62 of ring 60 is placed adjacent to tissue in the vicinity of (e.g., on or posterior to) the P3 segment of the posterior mitral valve leaflet (FIG. 9B). Mandrel 64 is withdrawn from opening 63 defined by the distal self-suturing anchor, such that the anchor automatically becomes anchored to the tissue, due the ends of the anchors penetrating the tissue, as described hereinabove (FIG. 9C).

Figure 9D:
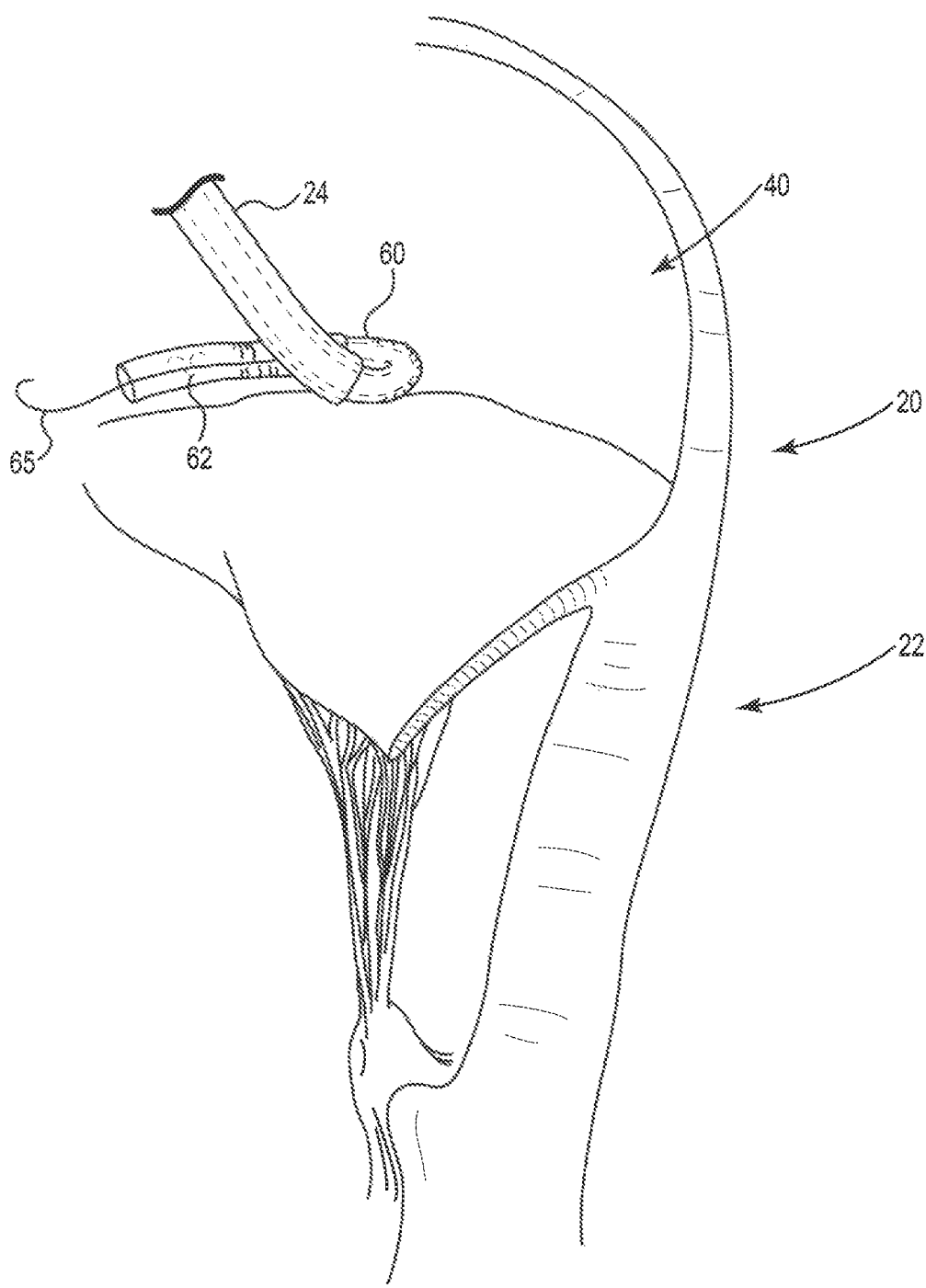
Figure 9E:
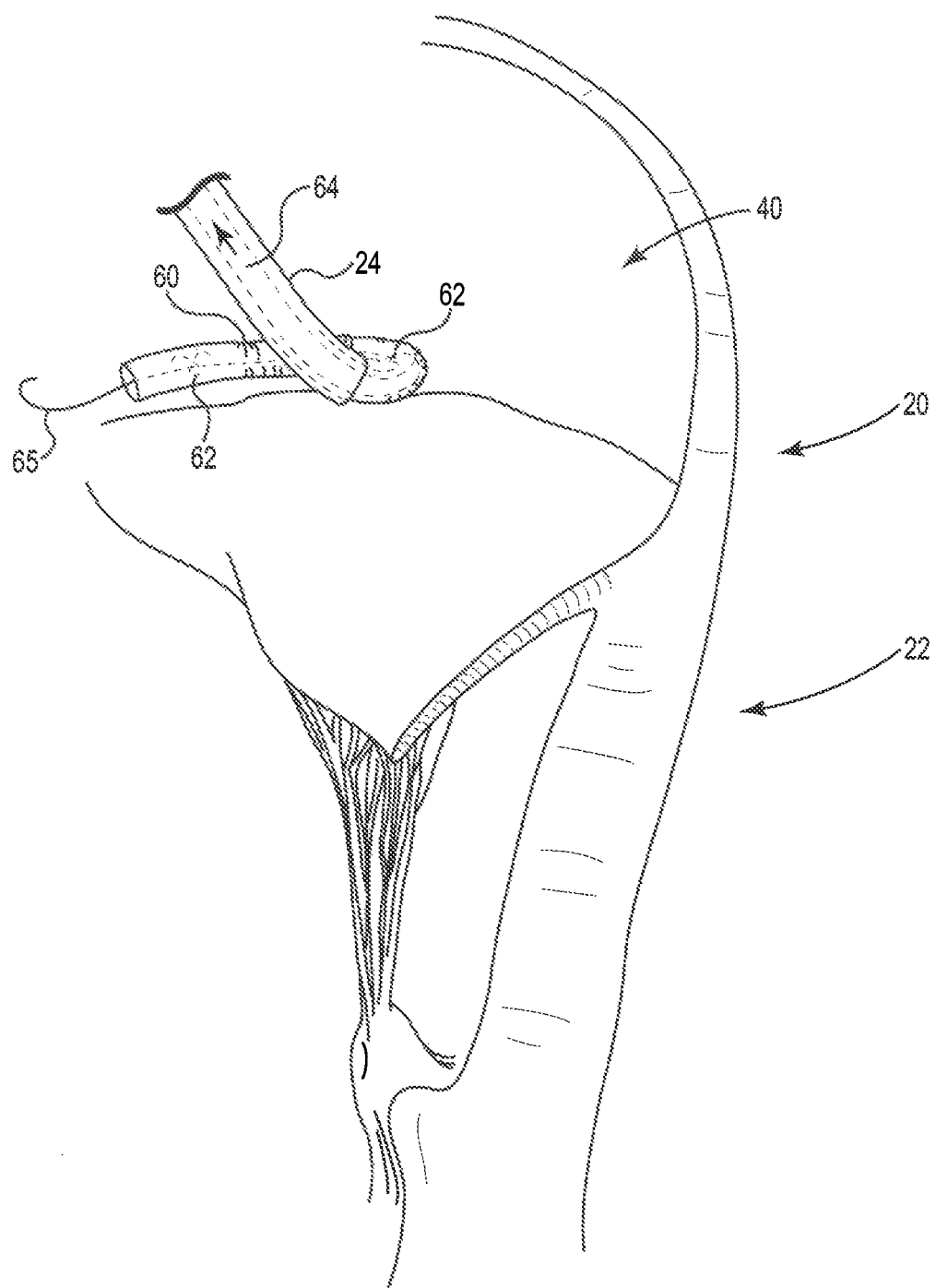

Subsequently, a second one of self suturing anchors 62 of ring 60 is placed adjacent to tissue in the vicinity of (e.g., on or posterior to) the P2 segment of the posterior mitral valve leaflet (FIG. 9D). Mandrel 64 is withdrawn from opening 63 defined by the self-suturing anchor, such that the anchor automatically becomes anchored to the tissue, due the ends of the anchors penetrating the tissue, as described hereinabove (FIG. 9E).

Figure 9F:
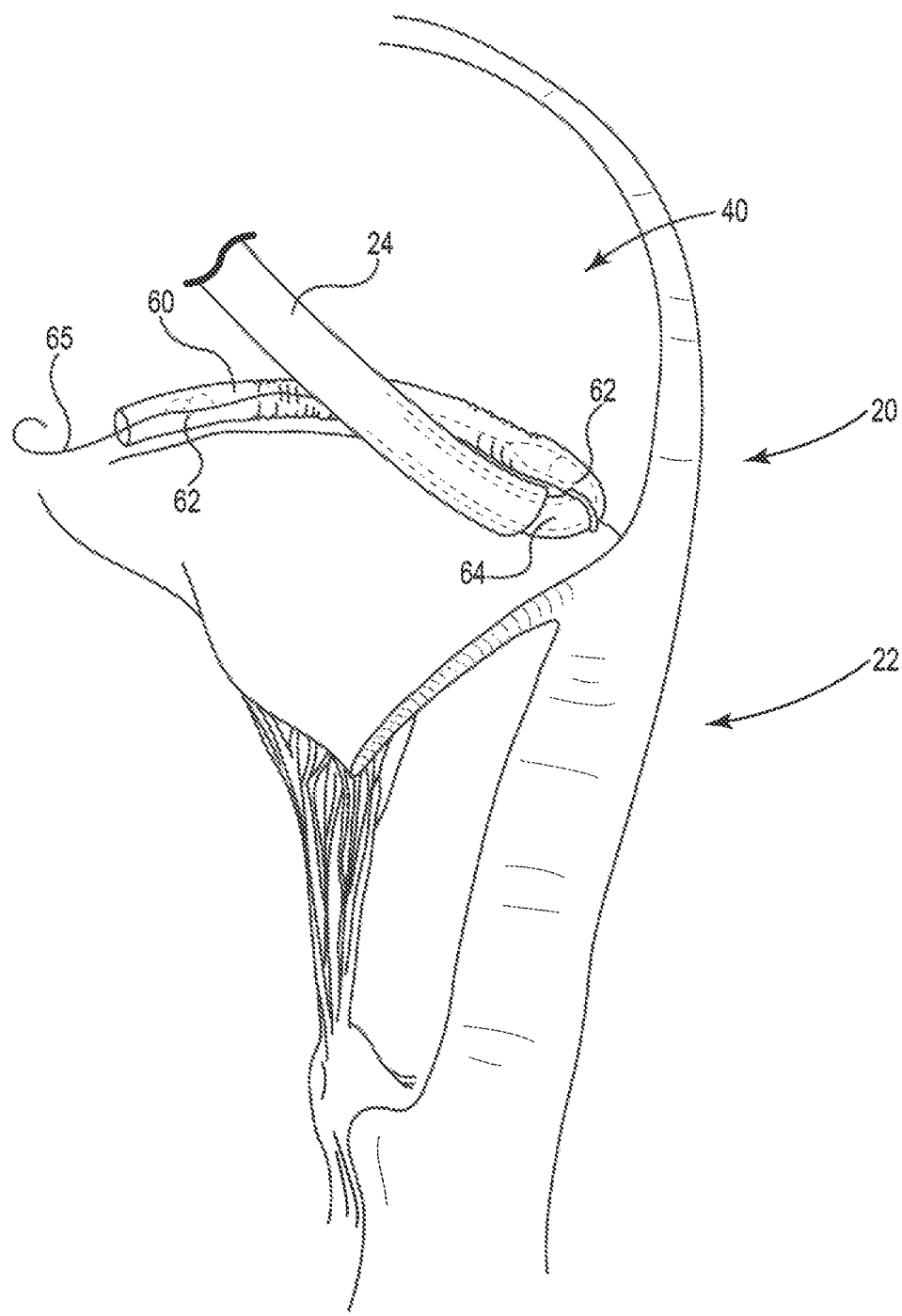
Figure 9G:
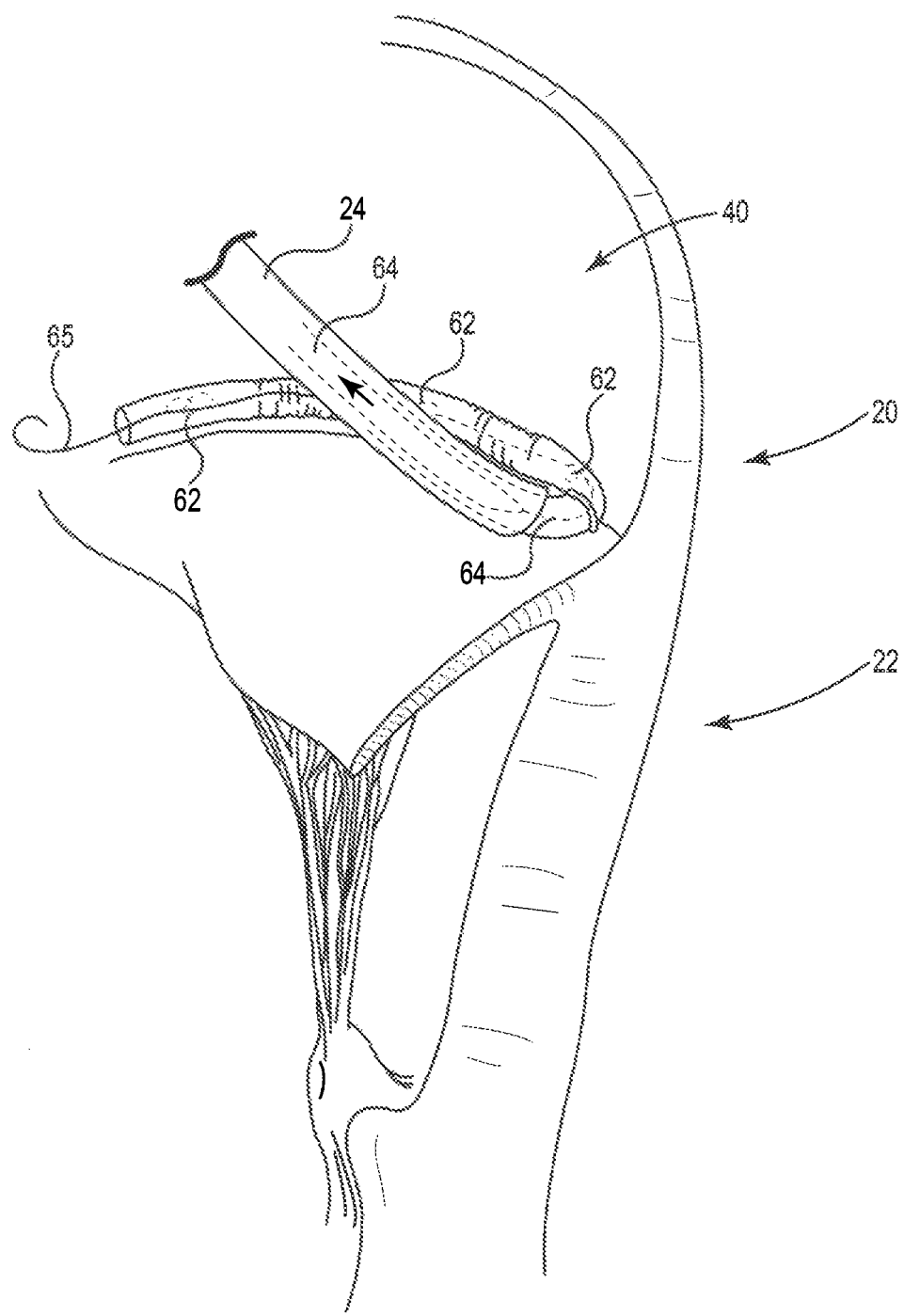

Further subsequently, a third one of self suturing anchors 62 of ring 60 is placed adjacent to tissue in the vicinity of (e.g., on or posterior to) the P1 segment of the posterior mitral valve leaflet (FIG. 9F). Mandrel 64 is withdrawn from opening 63 defined by the self-suturing anchor, such that the anchor automatically becomes anchored to the tissue, due the ends of the anchors penetrating the tissue, as described hereinabove (FIG. 9G).

Figure 9H:
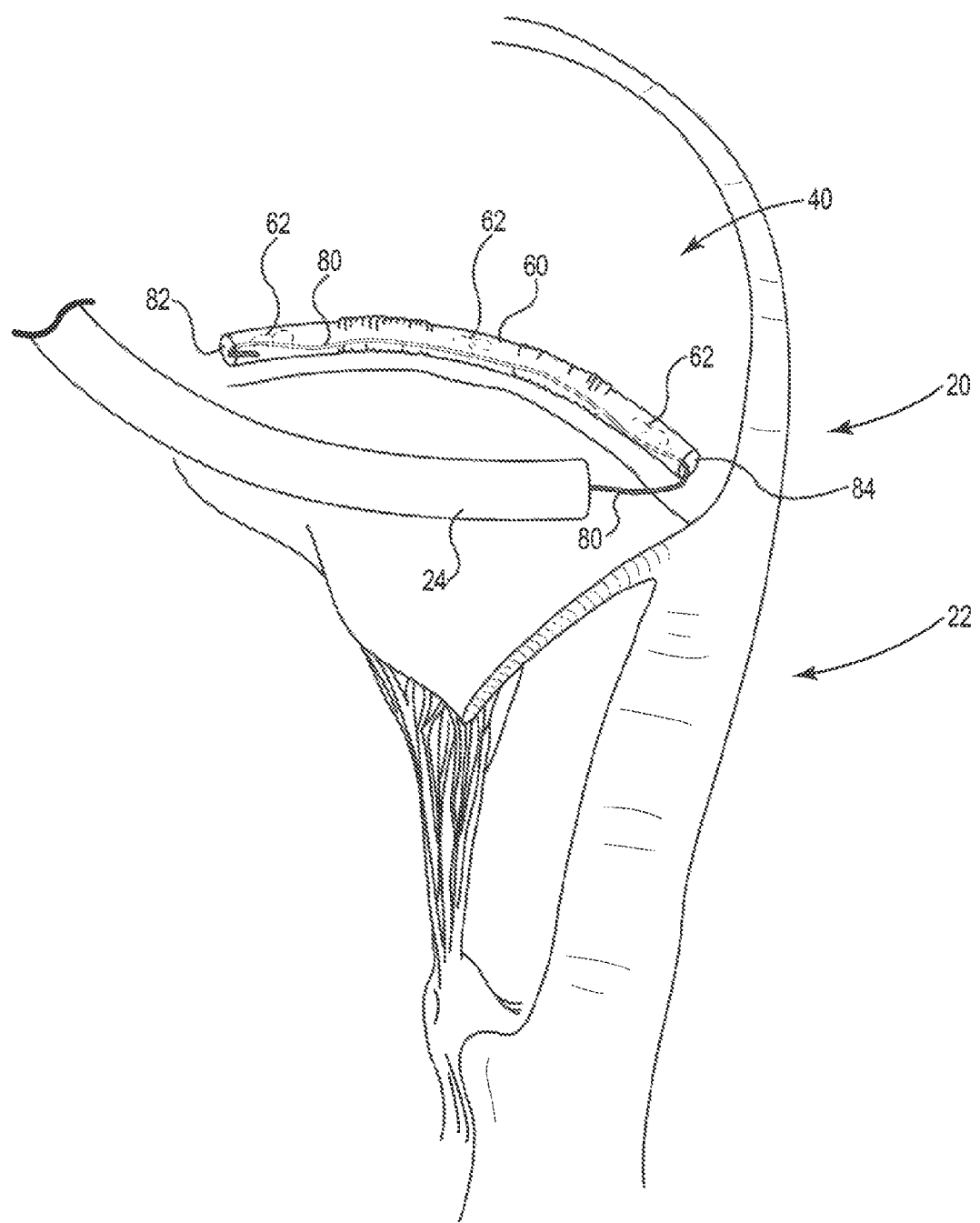
Figure 9I:
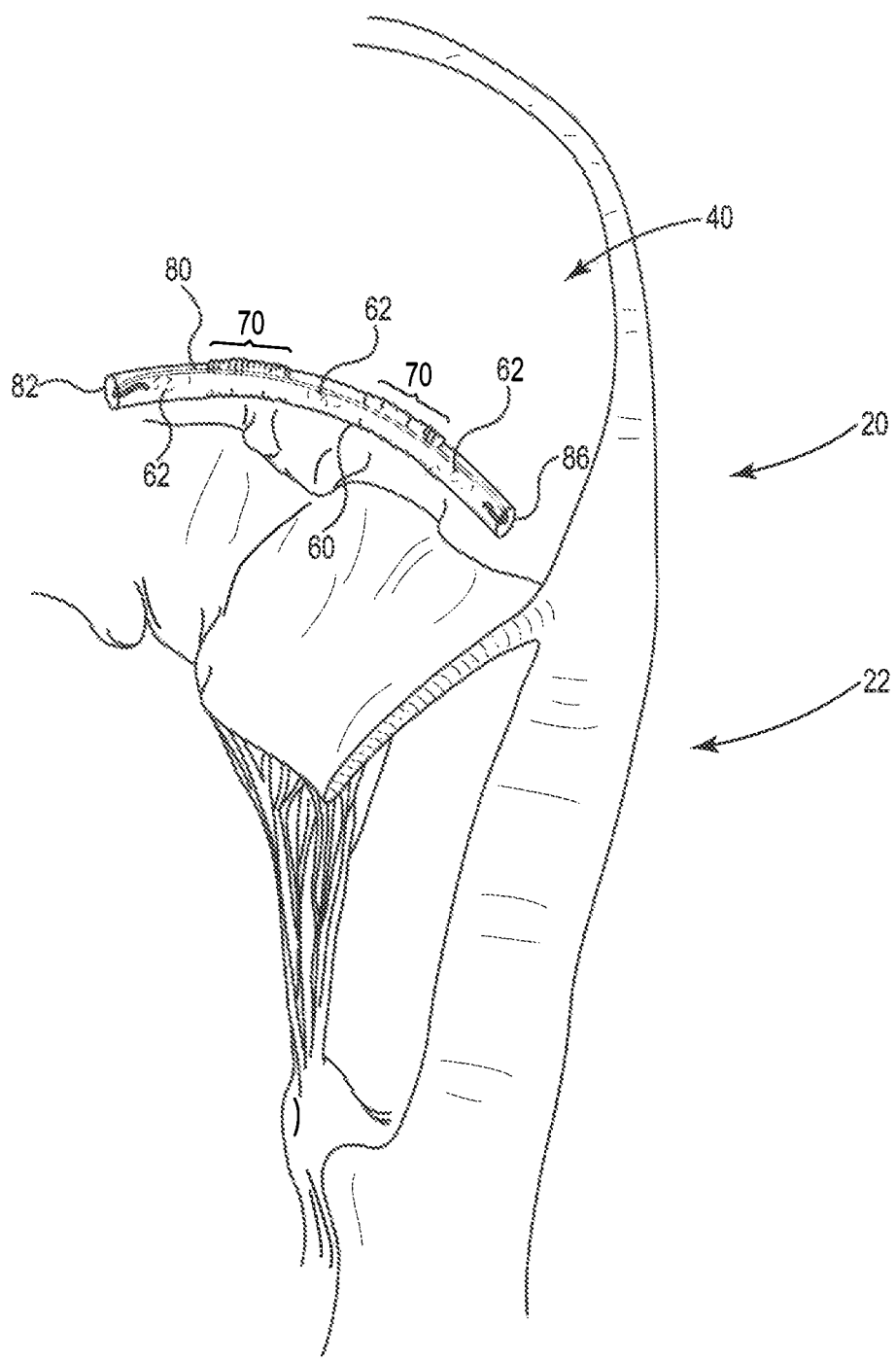

A tether 80 passes through the anchors, and is tied to mitral ring 60 in a vicinity of a first end 82 of the ring that is closest to the posterior commissure. The tether is tightened, so as to pull the anchors toward each other (FIG. 9H). The tether is then anchored in its tightened configuration, for example, by tying the tether to a second end 84 of the mitral ring that is closest to the anterior commissure (FIG. 9I). Flexible regions 70 of the mitral ring facilitate the movement of the anchors toward each other, in response to the tightening of tether 80, by flexing, and/or by becoming compressed. The tightening of the tether causes a decrease in the circumference of the mitral annulus.

It is noted that, although not shown, for some applications, mitral ring 60 is placed on the atrial aspect of the posterior mitral valve, as described with reference to FIGS. 9A-I, and is combined with the techniques described hereinabove, with reference to FIGS. 1-7, for tethering the posterior leaflet to anchoring location 32, which is at a cardiac site that is anterior and inferior to the posterior leaflet.

Reference is now made to FIGS. 10A-J, which are schematic illustrations of mitral ring 60 being implanted on the ventricular side of the posterior mitral valve via a transaortic retrograde approach, in accordance with some applications of the present invention. It is noted that although the mitral ring is shown as being delivered via a transaortic retrograde approach (via delivery catheter 24), for some applications, the mitral ring is delivered to the ventricular side of the posterior mitral valve via a transapical approach.

Figure 10A:
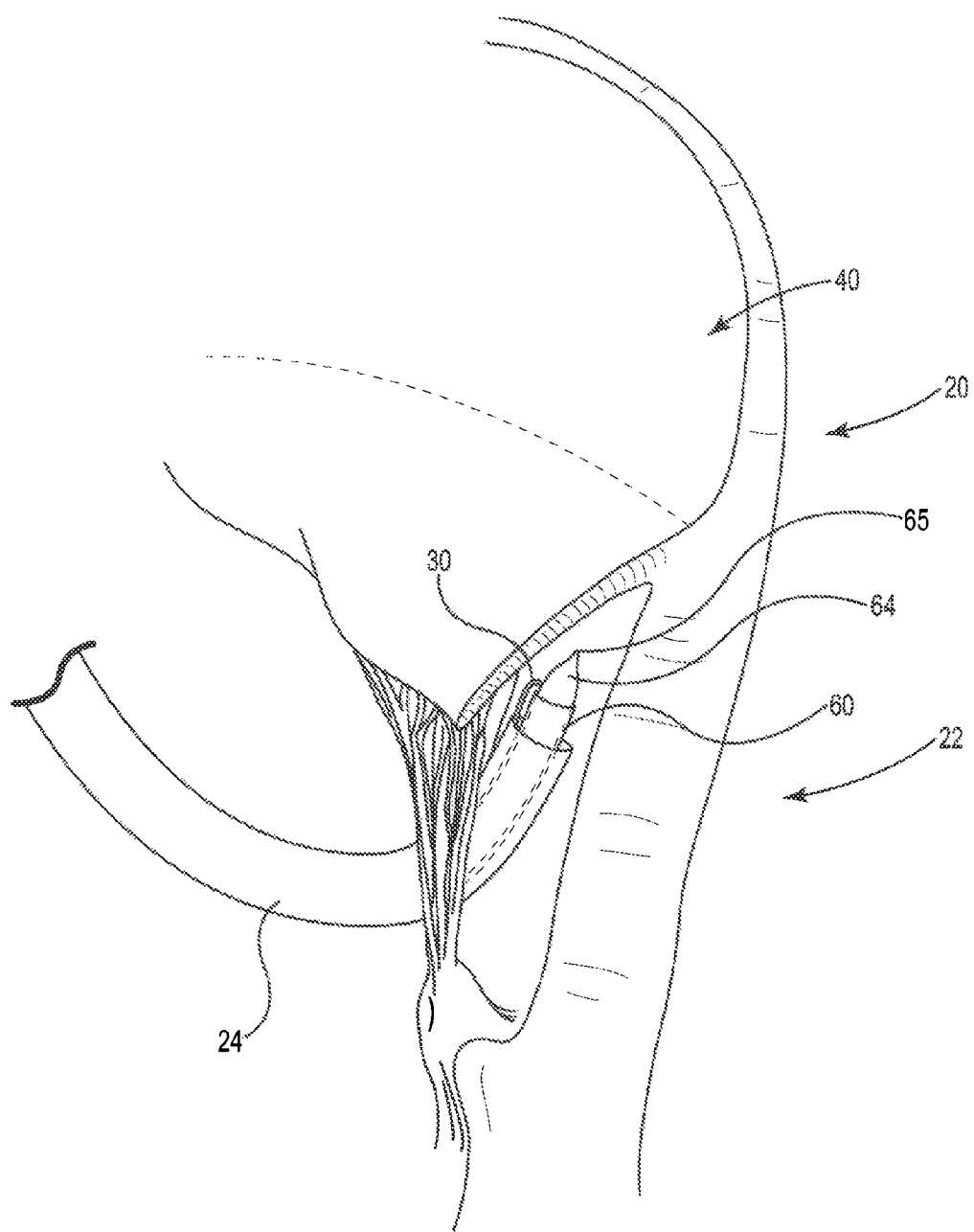
FIGS. 10A-J are schematic illustrations of the mitral ring being implanted on the ventricular side of the posterior mitral valve via a transaortic retrograde approach, in accordance with some applications of the present invention.
Figure 10B:
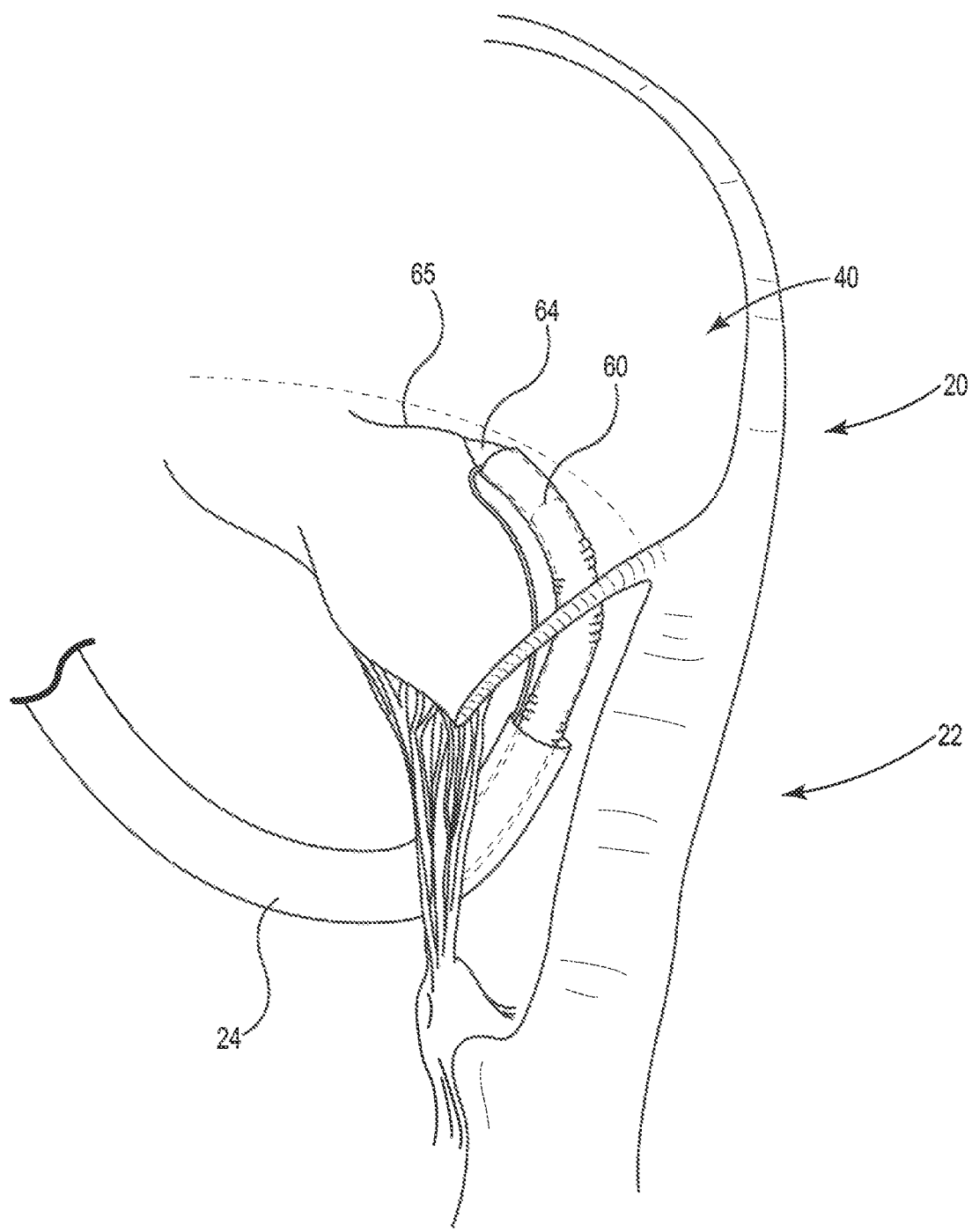
Figure 10C:
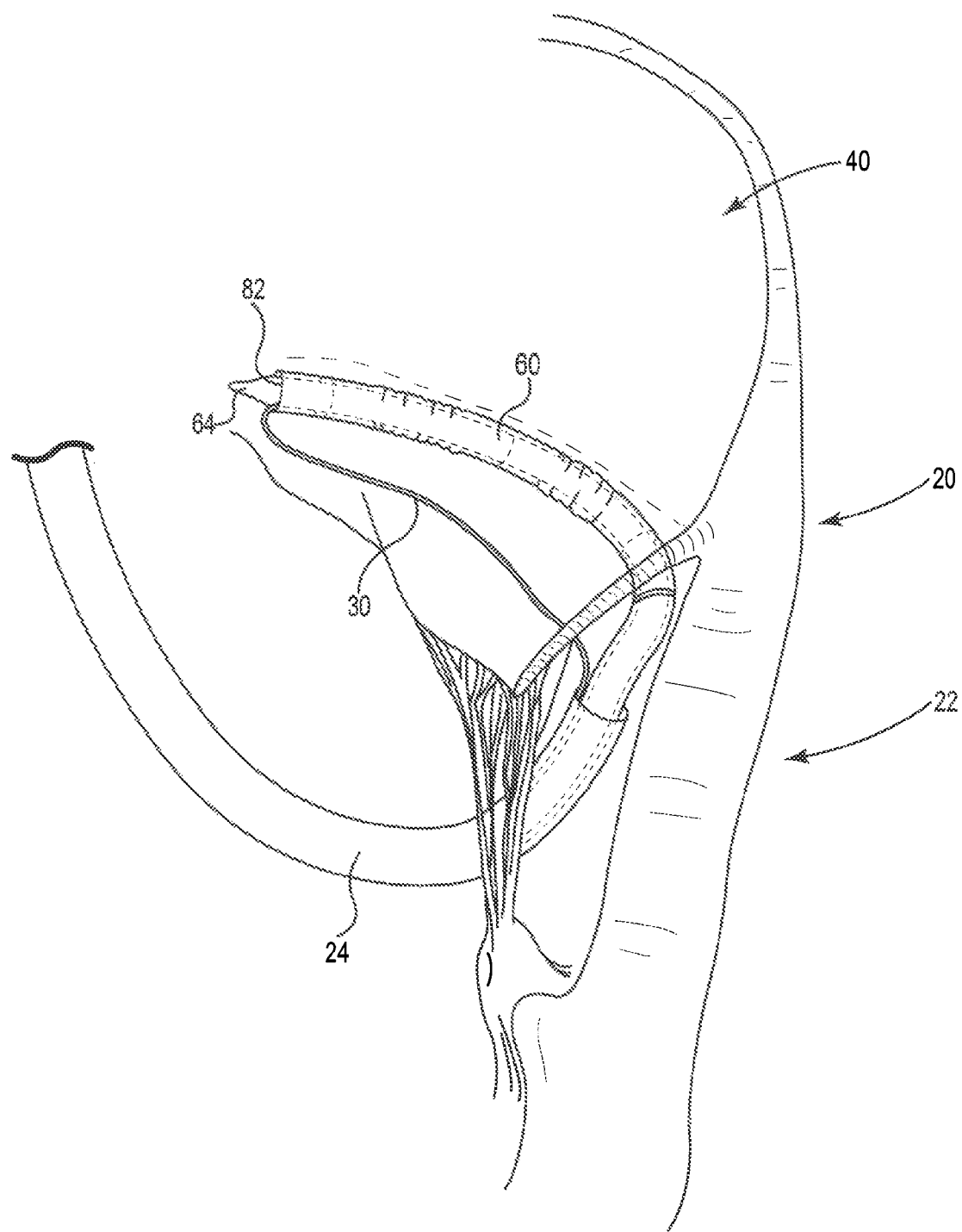
Figure 10D:
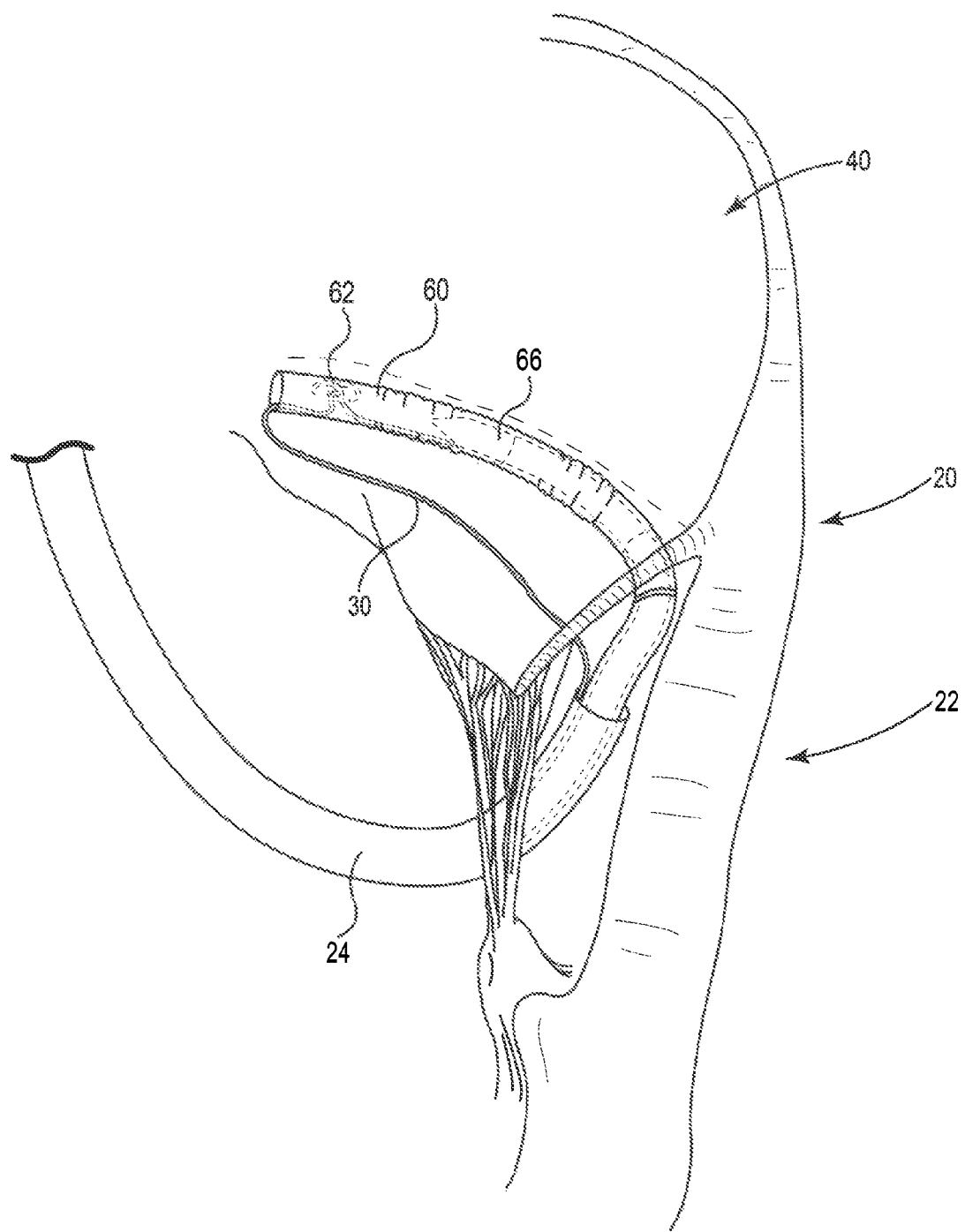
Figure 10E:
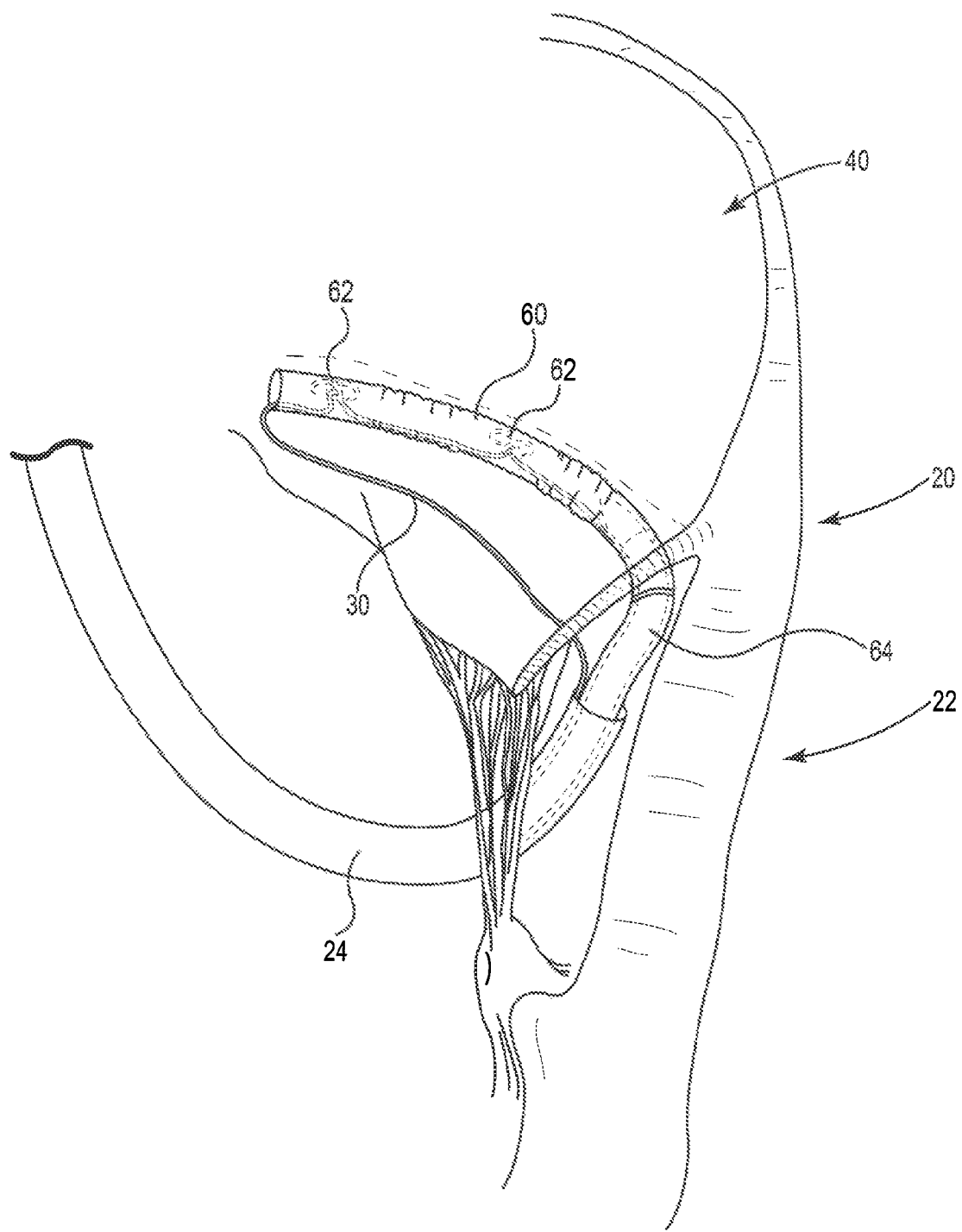
Figure 10F:
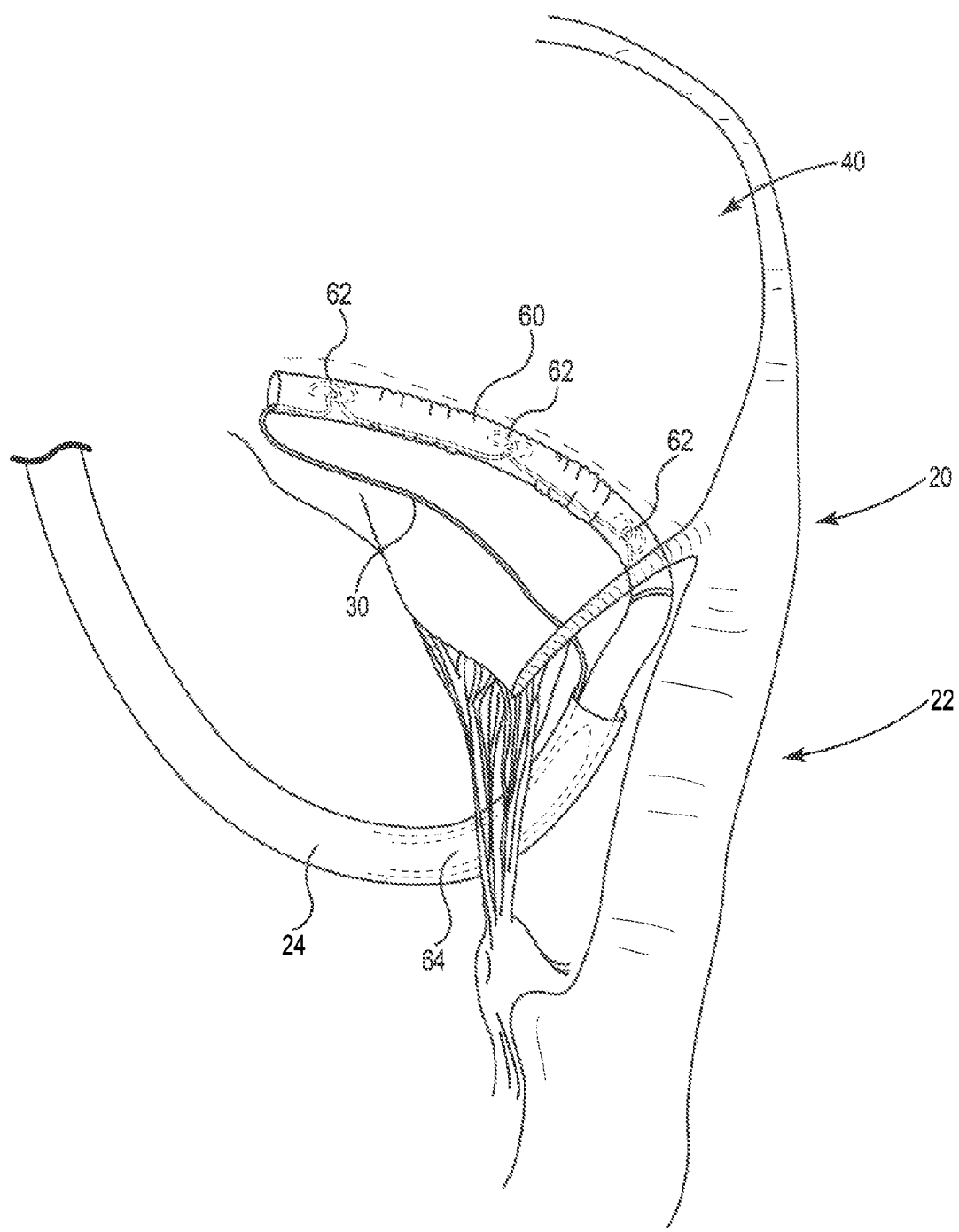
Figure 10G:
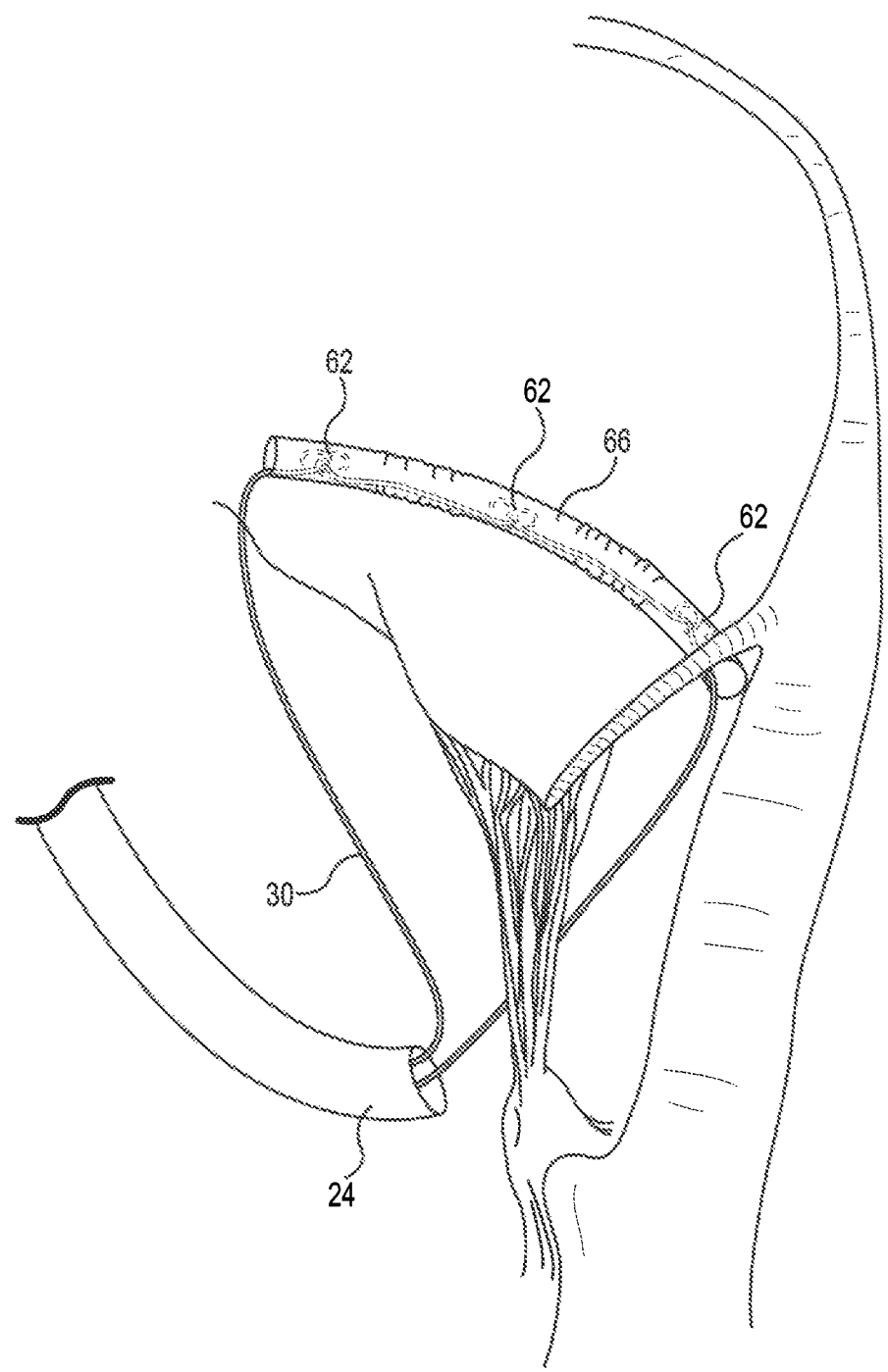

The mitral ring is passed along the groove between the posterior mitral valve leaflet and the left ventricular wall, such that first end 82 of the mitral ring is in the vicinity of the posterior commissure of the mitral valve, as shown in FIG. 10A-C. It is noted, for some applications, as shown, a first end of tether 30 passes out of the first end of the mitral ring. Typically, the mitral ring is placed such that first, second, and third self-suturing anchors 62 are adjacent to tissue in the vicinity of (e.g., on or posterior to) the P3, P2, and P1 segments of the posterior mitral valve leaflet. Mandrel 64 is withdrawn from the openings defined by self-suturing anchors, such that the anchors become anchored to the tissue and act as P1, P2, and P3 anchors, in accordance with the techniques described hereinabove, and as shown in FIGS. 10D-F.

Figure 10H:
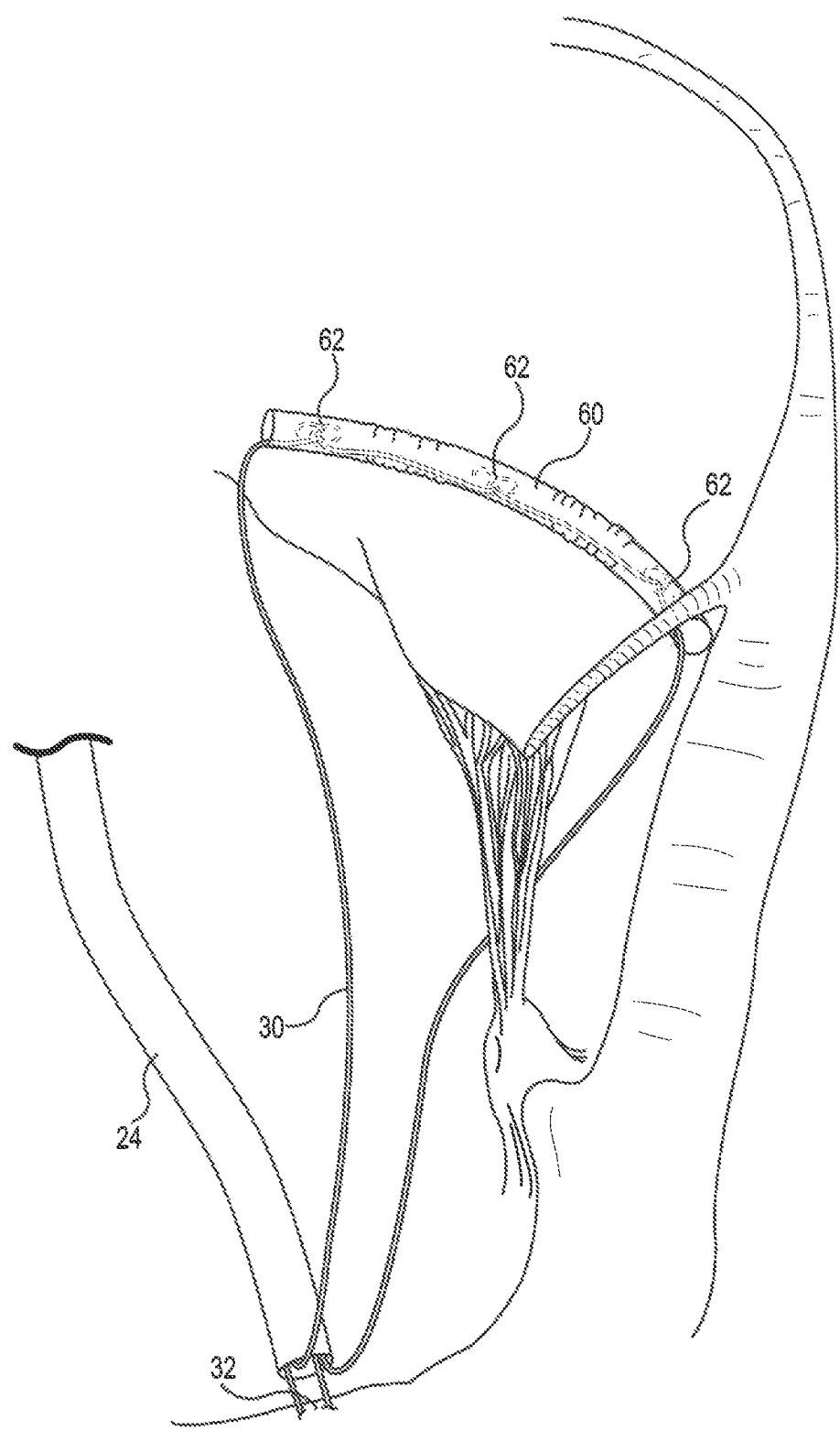
Figure 10I:
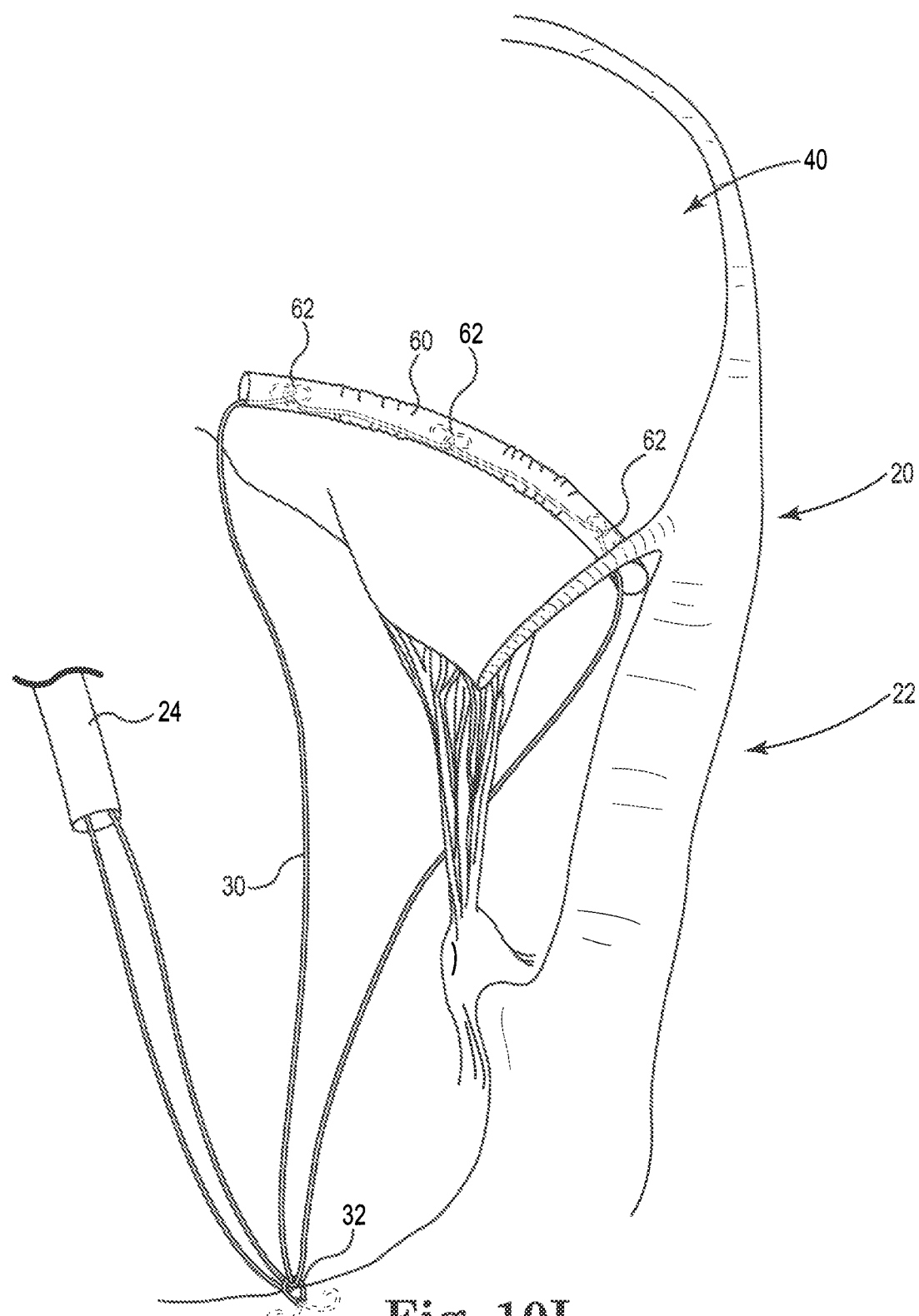
Figure 10J:
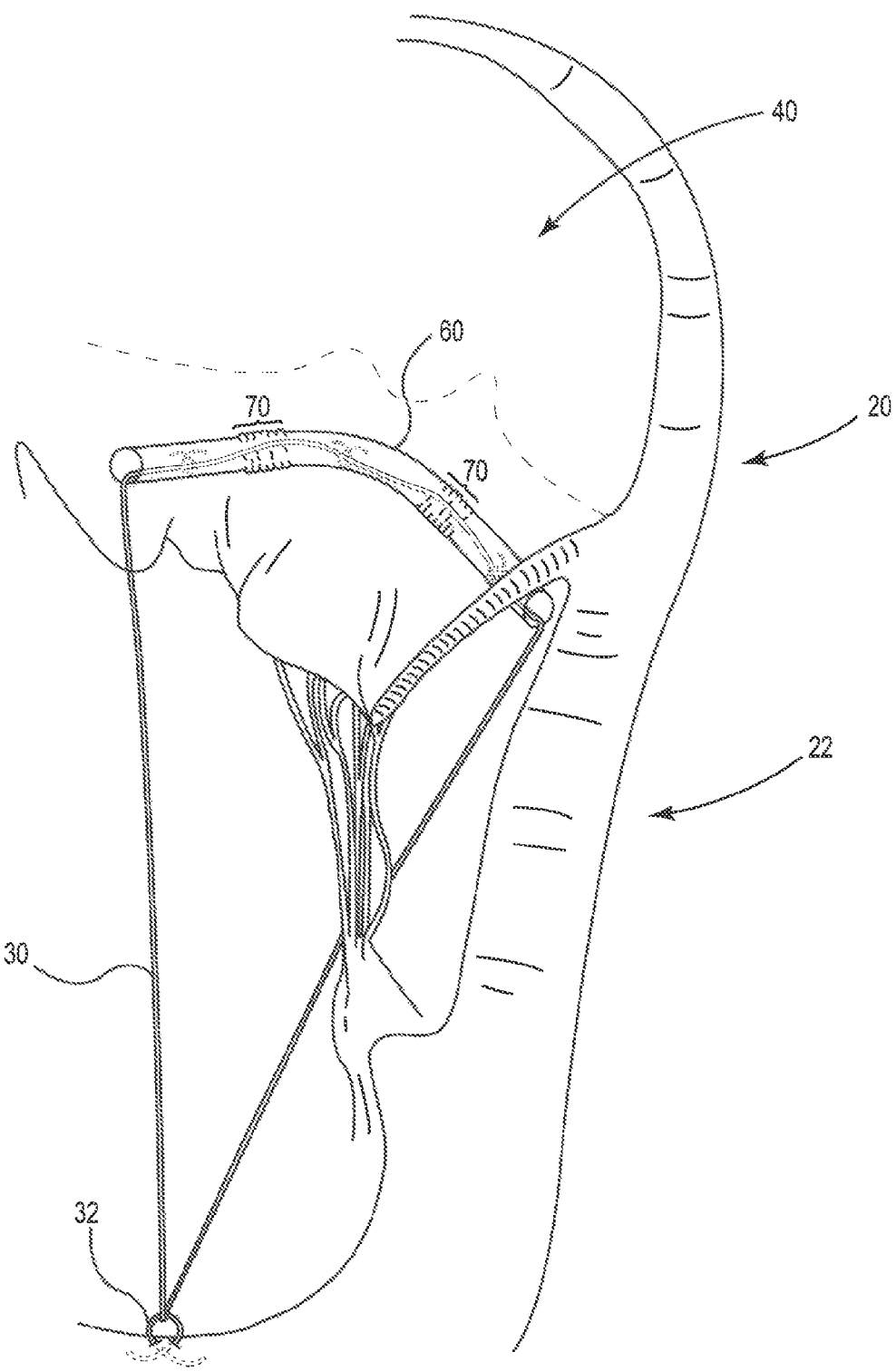

Subsequently, the distal tip of delivery catheter is moved toward anchoring location 32 (FIG. 10G), which, as described hereinabove, is at a cardiac site that is anterior and inferior to the posterior mitral valve leaflet. Tether 30 is tightened and anchored to anchoring location 32, in accordance with the techniques described hereinabove, as shown in FIGS. 10H-J. As shown in FIG. 10J, flexible regions 70 of the mitral ring facilitate flexing and compression of the mitral ring, such that the anchors are able to move toward each other, and such that the P1 and P3 anchors are able to move inferiorly, relative to the P2 anchor.

It is noted that although self-suturing anchors 62 and ring 60 are described hereinabove as being anchored to tissue associated with the mitral valve, the scope of the present invention includes anchoring self-suturing anchors (and, optionally, a housing) to natural or prosthetic tissue of other portions of a subject's body, mutatis mutandis.

For example, the anchors may anchor a ring to tissue of a subject's gastrointestinal tract. For some applications, the anchors and the ring are anchored to tissue in the vicinity of the sphincter muscles that are at the junction between the esophagus and the stomach and the ring is tightened in accordance with the techniques described hereinabove, e.g., in order to treat gastroesophageal reflux disease (GERD). Alternatively, the anchors anchor a ring to the inside of a subject's stomach, and the ring is tightened in accordance with the techniques described hereinabove, in order to treat obesity. Further alternatively, the anchors may be used to treat an atrial or a ventricular septal defect, to close a patent foramen ovale, and/or to treat an abdominal aortic aneurysm.

It will be appreciated by persons skilled in the art that the present invention is not limited to what has been particularly shown and described hereinabove. Rather, the scope of the present invention includes both combinations and sub combinations of the various features described hereinabove, as well as variations and modifications thereof that are not in the prior art, which would occur to persons skilled in the art upon reading the foregoing description.

The invention claimed is:

1. Apparatus for use with a mitral valve of a heart of a subject, the apparatus comprising:
   a P1-anchor, a P2-anchor, and a P3-anchor, configured to be anchored to tissue in a vicinity of, respectively, P1, P2 and P3 segments of a posterior leaflet of the mitral valve;
   a tether being fixedly coupled to the P2-anchor and slidably coupled to the P1 and P3 anchors, wherein a first segment of the tether extends from the P2-anchor and slidably extends through the P1-anchor and a second segment of the tether extends from the P2-anchor in an opposite direction from the first segment and slidably extends through the P3-anchor, wherein the first and second segments are of a length to inferiorly extend from the P1-anchor and the P3-anchor, respectively, to an anchoring location at a cardiac site anterior and inferior to the posterior leaflet; and
   a cardiac-site anchor having the first and second segments of the tether slidably extending therethrough, the cardiac-site anchor being configured to anchor the first and second segments of the tether to the anchoring location at the cardiac site,
   wherein the first and second segments of the tether are configured to be tensioned toward the cardiac-site anchor and to be secured in a tensioned state to the cardiac-site anchor such that the P1-anchor and the P3-anchor are pulled in an inferior direction by the respective first segment or second segment to thereby restore a saddle-shape to an annulus of the mitral valve when implanted.

2. The apparatus according to claim 1, wherein the cardiac-site anchor comprises a clip.

3. The apparatus according to claim 1, wherein the P1-anchor, the P2-anchor, and the P3-anchor each comprise a clip.

4. The apparatus according to claim 3, wherein the clips are shaped to define openings therethrough, wherein the apparatus further comprises a mandrel configured to be reversibly disposed through the openings, and wherein, in response to removing the mandrel from the openings, the clips are configured to automatically become anchored to the tissue.

5. The apparatus according to claim 1, wherein the apparatus further comprises a mitral ring configured to become coupled to the tissue by at least some of the anchors.

6. The apparatus according to claim 5, wherein the mitral ring comprises compressible portions thereof, the compressible portions being disposed between adjacent the anchors.

7. A method of treating a mitral valve of a heart of a subject, the method comprising:
   reducing a circumference of a mitral annulus and restoring a saddle-shape of the mitral annulus, by:
   anchoring a P1-anchor, a P2-anchor, and a P3-anchor to tissue in a vicinity of, respectively, P1, P2 and P3 segments of a posterior leaflet of the mitral valve, a tether being fixedly coupled to the P2-anchor, and slidably coupled to the P1 and P3 anchors, wherein a first segment of the tether extends from the P2-anchor and slidably extends through the P1-anchor and a second segment of the tether extends from the P2-anchor and slidably extends through the P3-anchor, wherein the first and second segments are of a length to inferiorly extend from the P1-anchor and the P3-anchor, respectively, to a cardiac-site anchor that is anchored at a cardiac site that is anterior and inferior to the posterior leaflet;
   subsequently, tensioning the first and second segments of the tether inferiorly toward the cardiac-site anchor; and
   anchoring the first and second segments of the tether to the cardiac-site anchor by securing the first and second segments in a tensioned state to the cardiac-site anchor such that the P1-anchor and the P3-anchor are pulled in an inferior direction by the respective first segment or second segment to thereby restore the saddle-shape of the mitral valve annulus.

8. The method according to claim 7, wherein the cardiac site of the cardiac-site anchor is an inner surface of the heart at a vicinity of an apex of the heart.

9. The method according to claim 7, wherein the cardiac site of the cardiac-site anchor is an outer surface of the heart at a vicinity of an apex of the heart.

10. The method according to claim 7, wherein anchoring the P1-anchor, the P2-anchor, and the P3-anchor comprises inserting the anchors transmyocardially into a left atrium of the subject, and anchoring the P1-anchor, the P2-anchor, and the P3-anchor to a left atrial side of the posterior leaflet of the mitral valve.

11. The method according to claim 7, wherein the P1-anchor, the P2-anchor, and the P3-anchor include a P1-clip, a P2-clip, and a P3-clip, and wherein anchoring the P1-anchor, the P2-anchor, and the P3-anchor comprises inserting the clips into a left ventricle of the subject and clipping the clips to a left ventricular side of the posterior leaflet of the mitral valve, such that the clips penetrate tissue of the posterior leaflet.

12. The method according to claim 7, wherein anchoring the first and second segments of the tether to the cardiac-site anchor comprises decreasing a ratio of an anteroposterior diameter of the mitral annulus to a lateral diameter of the mitral annulus.

13. The method according to claim 7, wherein anchoring the first and second segments of the tether to the cardiac-site anchor comprises reshaping a left ventricle of the subject.

14. The method according to claim 7, wherein the P1-anchor, the P2-anchor, and the P3-anchor are shaped to define openings therethrough, and wherein anchoring the P1-anchor, the P2-anchor, and the P3-anchor comprises causing the P1-anchor, the P2-anchor, and the P3-anchor to become anchored automatically, by removing a mandrel from inside the openings defined by the P1-anchor, the P2-anchor, and the P3-anchor.

15. The method according to claim 14, wherein the P1-anchor, the P2-anchor, and the P3-anchor are coupled to a ring, and wherein anchoring the P1-anchor, the P2-anchor, and the P3-anchor to the tissue comprises coupling the ring to the tissue.

* * * * *